US008629241B2

(12) United States Patent
Fairlie et al.

(10) Patent No.: US 8,629,241 B2
(45) Date of Patent: Jan. 14, 2014

(54) ALPHA HELICAL MIMICS, THEIR USES AND METHODS FOR THEIR PRODUCTION

(75) Inventors: David P. Fairlie, Springwood (AU); Nicholas E. Shepherd, St. Lucia (AU)

(73) Assignee: The University of Queensland, St. Lucia (AU)

( * ) Notice: Subject to any disclaimer, the term of this patent is extended or adjusted under 35 U.S.C. 154(b) by 0 days.

(21) Appl. No.: 13/483,926

(22) Filed: May 30, 2012

(65) Prior Publication Data
US 2012/0238507 A1    Sep. 20, 2012

Related U.S. Application Data

(62) Division of application No. 10/593,407, filed as application No. PCT/AU2005/000400 on Mar. 21, 2005, now Pat. No. 8,193,310.

(30) Foreign Application Priority Data

Mar. 19, 2004    (AU) ................ 2004901447

(51) Int. Cl.
    C07K 5/12     (2006.01)
    C07K 7/00     (2006.01)
    C07K 7/06     (2006.01)
    C07K 7/56     (2006.01)

(52) U.S. Cl.
    USPC ......................................... 530/317; 530/330

(58) Field of Classification Search
    None
    See application file for complete search history.

(56) References Cited

U.S. PATENT DOCUMENTS

| 5,149,779 A | 9/1992 | Chorev et al. |
| 5,364,851 A | 11/1994 | Joran |
| 6,169,071 B1 | 1/2001 | Blaschuk et al. |
| 2002/0169106 A1* | 11/2002 | Blaschuk et al. .................. 514/2 |

FOREIGN PATENT DOCUMENTS

| WO | WO 95/31480 | 11/1995 |
| WO | WO 97/42223 | 11/1997 |
| WO | WO 00/01730 | 1/2000 |
| WO | WO 2004/067021 | 8/2004 |

OTHER PUBLICATIONS

Definition of residue from http://dictionary.reference.com/browse/residue, pp. 1-4. Accessed Jul. 13, 2009.*
Bouvier M et al., (1992, J. Med. Chem., 35(6): 1145-1155).
Kapurniotu Afrodite et al., (1995, J. Med. Chem. 38(5): 836-847).
Sanchez J et al., (1988 Febs Lett. 241: 110-114).
Barlow, D.J.: Thornton. J. M. *J. Mol. Biol.* 1988, 201,601.
Fairlie, D.; West, M.; Wong, A. *Curr. Med. Chem.* 1998, 5, 29.
Andrews, M. J. I.; Tabor, A. B. *Tetrahedron* 1999, 55, 11711.
Kussie, P. H.; Gorina, S.; Marechal, V.: Elenbaas, B.; Moreau, J.;*Science* 1996, 274, 948-953.
Burley, S. K.; Roeder, R.G. *Ann. Rev. Biochem.* 1996. 65, 769.
Uesugi, M.; Nyaguile, O.; Lu, H.; Levine, A. J.; Verdine, G. L. *Science* 1997, 277, 1310.
Sattler, M.; Liang, H.; Nettesheim, D.; Meadows, R. P.; Harlan, J. E.; Eberstadt, M.; Yoon, H. S.; Shuker, S. B.; Chang, B. S.; Minn, A. J.; Thompson, C. B.; Fesik, S. W. *Science* 1997, 275, 983-986.
Tan, R.; Chen, L.; Buettner, J.A.; Hudson, D.; Frankel, A.D. *Cell* 1993, 73, 1031.
Pabo, C. O.; Peisach, E.; Grant, R. A. *Annual Review of Biochemistry* 2001, 70, 313-340.
Weiss, M. A.; Narayana, N. *Biopolymers* 1998, 48, 167-180.
Botuyan, M. V.; Mer, G.; Yi, G.; Koth, C. M.; Case, D. A.; Edwards, A. M.; Chazin, W. J.; Arrowsmith, C. H. *J. Mol. Biol.* 2001, 312, 177-186.
Uesugi, M.; Nyanguile, O.; Lu, H.; Levine, A. J.; Verdine, G. L. *Science* 1997, 277, 1310-1313.
Jin, L.; Briggs, S. L.; Chandrasekhar, S.; Chirgadze, N. Y.; Clawson, D. K.; Scheivitz, R. W.; Smiley, D. L.; Tashjian, A. H.; Zhang, F. *Journal of Biological Chemistry* 2000, 275, 27238-27244.
Schwyzer, R. *Biochemistry* 1986, 25, 4281-4286.
Bennett, M. A.; Murray, T. F.; Aldrich, J. V. *Journal of Medicinal Chemistry* 2002, 45, 5617-5619.
Zaiou, M. Z.; Arnold, K. S.; Newhouse, Y. M.; Innerarity, T. L.; Weisgraber, K. H.; Segall, M. L.; Phillips, M. C.; Lund-Katz, S. *Journal of Lipid Reseach* 2000, 41, 1087-1095.
Kirby, D. A.; Koerber, S. C.; Craig, A. G.; Feinstein, R. D.; Delmas, L.; Brown, M. R.; Rivier, J. E. *Journal of Medicinal Chemistry* 1993, 36, 385-393.
Carpenter, K. A.; Schmidt, R.; Yue, S. Y.; Hodzic, L.; Pou, C.; Payza, K.; Godbout, C.; Brown, W.; Roberts, E. *Biochemistry* 1999, 38, 15295-15304.
Miranda, A.; Lahrichi, S. L.; Gulyas, J.; Koerber, S. C.; Craig, A. G.; Corrigan, A.; Rivier, C.; Vale, W.; Rivier, J. *Journal of Medicinal Chemistry* 1997, 40, 3651-3658.
McInerney, E. M.; Rose, D. W.; Flynn, S. E.; Westin, S.; Mullen, T. M.; Krons, A.; Inostroza, J.; Torchia, J.; Nolte, R. T.; Assa-Mont, N.; Milburn, M. V.; Glass, C. K.; Rosenfeld, M. G. *Genes Dev* 1998, 12, 3357-3368.
Chang, C.; Norris, J. D.; Gron, H.; Paige, L. A.; Hamilton, P. T.; Kenan, D. J.; Fowlkes, D.; McDonnell, D. P. *Mol Cell Biol* 1999, 19, 8226-8239.
Zimm, B.; Bragg, J. J. *Chem. Phys.* 1959, 31, 526.
Scholtz, A.; Baldwin, R. L. *Annu. Rev. Biophys. Biomol. Struct.* 1992, 21, 95.
Kemp, D.; Curran, T.; Boyd, J.; Allen, T. *J. Org. Chem.* 1991, 56, 6683.
Muller, K.; Obrecht, D.; Knierzinger, A.; Stankovic, C.; Spiegler, C.; Bannwarth, W.; Trzeciak, A.; Englert, G.; Labhardt, A. M.; Schoenholzer, P. *Perspect. Med. Chem.* 1993, 513.

(Continued)

*Primary Examiner* — Julie Ha
(74) *Attorney, Agent, or Firm* — Casimir Jones, S.C.

(57) ABSTRACT

Disclosed are short chain peptides that are constrained to adopt an alpha helicial conformation and their use as alpha helical scaffolds for directing amino acid side chains into positions analogous to those found in longer chain alpha helical peptides. Also disclosed is the use of these peptides for attaching peptidic or non-peptidic appendages in order to mimic side chains of longer alpha helical peptides. The peptides find use in mimicking naturally occurring peptides or proteins or in preparing new materials.

22 Claims, 12 Drawing Sheets

(56) References Cited

OTHER PUBLICATIONS

Austin, R.; Maplestone, R. A.; Sefler, A. M.; Liu, K.; Hruzewicz, W. N.; Liu, C.; Cho, H. S.; Wemmer, D. E.; Bartlett, P. A. *J. Am. Chem. Soc.* 1997, 119, 6461.
Aurora, R.; Rose, G. D. *Protein Science* 1998, 7, 21.
Ghadiri, M. R.; Choi, C. *J. Am. Chem. Soc.* 1990, 112, 1630.
Ruan, F.; Chen, Y.; Hopkins, P. B. *J. Am. Chem. Soc.* 1990, 112, 9403.
Ghadiri, M. R.; Fernholz, H. J. *Am. Chem. Soc.* 1990, 112, 9633.
Kohn, W. D.; Kay, C. M.; Sykes, B. D.; Hodges, R. S. *J. Am. Chem. Soc.* 1998, 120, 1124.
Kelso, M. J.; Hoang, H.; Appleton, T. G.; Fairlie, D. P. *J. Am. Chem. Soc.* 2000, 122, 10488.
Kelso, M. J.; Hoang, H. N.; Oliver, W. N.; Sokolenko, N.; Mar., D. R.; Appleton, T. G.; Fairlie, D. P. *Angew Chem, Int. Edit.* 2003, 42, 421-424.
Rajashankar, K. R.; Ramakumar, S.; Jain, R. M.; Chauhan, V. S. *J. Am. Chem, Soc.* 1995, 117, 10129.
Karle, I. L.; Balaram, P. *Biochem.* 1990, 29, 6747.
Mayne, L.; Englander, S. W.; Qiu, R.; Yang, J.; Gong, Y.; Spek, E. J.; Kallenbach, N. R. *J. Am. Chem. Soc.* 1998, 120, 10643.
Albert, J. S.; Hamilton, A. *Biochem.* 1995, 34, 984.
Pellegrini, M.; Royo, M.; Chorev, M.; Mierke, D. F. *J. Pep. Res.* 1997, 49, 404.
Jackson, D. Y.; King, D. S.; Chmielewski, J.; Singh, S.; Schultz, P. G. *J. Am. Chem. Soc.* 1991, 113, 9391.
Cabezas, E.; Satterthwait, A. C. *J. Am. Chem. Soc.* 1999, 121, 3862.
Taylor, J. W. *Biopolymers* 2002, 66, 49.
Schievano, E.; Mammi, S.; Bisello, A.; Rosenblatt, M.; Chorev, M.; Peggion, E. *J. Pept. Sci.* 1999, 5, 330.
Bracken, C.; Gulyas, J.; Taylor, J. W.; Baum, J. *J. Am. Chem. Soc.* 1994, 116, 6431.
Phelan, J. C.; Skelton, N. J.; Braisted, A. C.; McDowell, R. S. *J. Am. Chem. Soc.* 1997, 119, 455. (e) Taylor, J. W.; Yu, C. *Bioorg. Med. Chem.* 1999, 7, 161.
Chen, S.-T.; Chen, H.-J.; Yu, H.-M.; Wang, K.-T. *J. Chem. Res. (S)* 1993, 228.
Osapay, G.; Taylor, J. W. *J. Am. Chem. Soc.* 1992, 114, 6966.
Yu, C,; Taylor, J. W. *Tet Lett.* 1996, 37, 1731.
Geistlinger T. R.; Guy, R. K. *J. Am. Chem. Soc.* 2001, 123, 1525.
Schafmeister, C. E.; Po, J.; Verdine, G. L. *J. Am. Chem. Soc.* 2000, 122, 5891.
Blackwell, H. E.; Sadowsky, J. D.; Howard, R. J.; Sampson, J. N.; Chao, J. A.; Steinmetz, W. E.; O'Leary, D. J.; Grubbs, R. H. *J. Org. Chem.* 2001, 66, 5291.
Judice, J. K.; Torn, J. Y. K.; Huang, W.; Wrin, T.; Vennari, J.; Petropoulos, C. J.; McDowell, R. S. *Proc. Natl. Acad. Sci.* 1997, 94, 13426.
Orner, B. P.; Ernst, J. T.; Hamilton, A. D. *J. Am. Chem. Soc.* 2001, 123, 5382.
Kutzki, O.; Park, H. S.; Ernst, J. T.; Orner, B. P.; Yin, H.; Hamilton, A. D. *J. Am. Chem. Soc.* 2002, 124, 11838.
Ernst, J. T.; Becerril, J.; Park, H. S.; Yin, H.; Hamilton, A. D. *Angew Chem. Int. Edit.* 2003, 42, 535.
Kemp, D. S.; Curran, T. P.; Davis, W. M.; Boyd, J. G.; Muendel, C. *Journal of Organic Chemistry* 1991, 56, 6672-6682.
Kemp, D. S.; Rothman, J. H. *Tetrahedron Letters* 1995, 36, 4019-4022.
Kemp, D. S.; Rothman, J. H. *Tetrahedron Letters* 1995, 36, 4023-4026.
Kemp, D. S.; Rothman, J. H.; Curran, T. C.; Blanchard, D. E. *Tetrahedron Letters* 1995, 36, 3809-3812.
Kemp, D. S.; Rothman, J. H. *Tetrahedron Letters* 1995, 36, 3813-3816.
Kahn, M.; Kim, H.-O.; Urban, J.; Molecumetics Ltd.: United States, 1999; vol. 5859184.
Cabezas, E.; Satterthwait, A. C. *J. Am. Chem. Soc.* 1999, 121, 3862-3875. (hard copy supplied).
Lyu, P. C.; Sherman, J. C.; Chen, A.; Kallenbach, N. R. *Proc. Natl. Acad. Sci. U. S. A.* 1991, 88, 5317-5320.
Zhang, C.; Miller, W.; Valenzano, K. J.; Kyle, D. J. *Journal of Medicinal Chemistry* 2002, 45, 5280-5286.
Garcia-Echeverria, C.; Chene, P.; Blommers, M. J. J.; Furet, P. *Journal of Medicinal Chemistry* 2000, 43, 3205-3208.
Bryant, S. D.; Guerrini, R.; Salvadori, S.; Bianchi, C.; Tomatis, R.; Attila, M.; Lazarus, L. H. *Journal of Medicinal Chemistry* 1997, 40, 2579-2587.
Leduc, A.; Trent, J. O.; Wittliff, J. L.; Bramlett, K. S.; Briggs, S. L.; Chirgadze, N. Y.; Wang, Y.; Burris, T. P.; Spatola, A. F. *Proc. Natl. Acad. Sci. U. S. A.* 2003, 100, 11273-11278.
Houston, M. E.; Gannon, C. L.; Kay, C. M.; Hodges, R. S. *Journal of Peptide Science* 1995, 1, 274-282.
Tian, Y.; Ramesh, C. V.; Ma, X.; Naqvi, S.; Patel, T.; Cenizal, T.; Tiscione, M.; Diaz, K.; Crea, T.; Arnold, E.; Arnold, G. F.; Taylor, J. W. *Journal of Peptide Research* 2002, 59, 264-276.
Fairlie DP, Abbenante G, Mar. DR: Macrocyclic peptidomimetics—forcing peptides into bioactive conformations. *Curr. Med. Chem.* 1995, 2: 654-686.
Stradley, S.; Rizo, J.; Bruch, M.; Stroup, A.; Gierasch, L. *Biopolymers*, 1990, 29, 263.
Toniolo, C. *Int. J. Peptide Protein Res.* 1990, 35, 287.
Schiller, P. W. In Medicinal Chemistry for the 21st Century, Wermuth, C. G. (ed.) IUPAC/Blackwell, London, 1992, pp. 215-232.
Kemp, D. S. In Medicinal Chemistry for the 21st Century, Wermuth, C. G. (ed.) IUPAC/Blackwell, London, 1992, pp. 259-277.
Kessler, H.; Diefenbach, B.; Finsinger, D.; Geyer, A.; Gurrath, M.; Goodman, S. L.; Hoelzemann, G.; Haubner, R.; Jonczyk, A.Lett. Pept. Sci. 1995, 2, 155.
Marraud, M.; Aubry, A. *Biopolymers* 1996, 40, 45.
X.-M.Cheng, S, S. Nikam, Doherty, A. M. *Curr. Med. Chem.* 1994, 1, 271.
Holzemann, G. *Kontakte* (Darmstadt) 1991, 1, 3-12; 2, 55.
Zhang LH, Pesti JA, Costello TD, Sheeran PJ, Uyeda R, Ma P, Kauffman GS, Ward R, McMillan JL: An efficient synthesis of cyclic RGD peptides as antithrombotic agents. *J. Org. Chem.* 1996, 61:5180-5185.
Haubner R, Finsinger D, Kessler H: Stereisomeric peptide libraries and peptidomimetics for designing selective inhibitors of the D v03 integrin for a new cancer therapy. *Angew. Chem., Int. Ed. Engl.* 1997, 36:1374-1389.
White HD: Unmet therapeutic needs in the management of acute ischemia. *Am. J. Cardiology* 1997, 80:B2-B10.
Finch, A. M.; Wong, A. K.; Wadi, S. K.; Paczkowski, N. J.; Fairlie, D. P.; Taylor, S. M. Low Molecular Weight Peptidic and Cyclic Antagonists of the Receptor for the Complement Factor C5a, *J. Med. Chem.* 1999, 42, 1965-1974.
McDonnel PA, Caldwell GW, Leo GC, Podlogar BL, Maryanoff BE: NMR three dimensional solution structure of the serine protease inhibitor cyclotheonamide A. *Biopolymers* 1997, 41: 349-358.
Osapay, G., Taylor, J.W., J. Am. Chem. Soc., 1990, 112, 6046-6051.
Condon, S.M. et. al., *J. Am. Chem. Soc.*, 2000, 112, 3007-3014.
Calo, G., Guerrini, R.; Salvadori, S.; Regoli, D. *Brit. J. Pharmacol.* 2000, 129:1261-83.
Reinscheid, R.K.; Ardati, A.; Monsma Jr, F.J.; Civelli, O. *J. Biol. Chem.* 1996, 24(14): 14163-68.
Salvadori, S.; Picone, D.; Tancredi, T.; Guerrini, R.; Spadaccini, R.; Lazarus, L.H.; Regoli, D.; Temussi, P.A. *Biochem. Biophys. Res. Comm.* 1997, 233:640-643.
Marqusee, S.; Baldwin, R.L., *Proc. Natl. Acad. Sci. USA.*, 1987, 84, 8898-8902.

\* cited by examiner

SEQUENCE LISTING

<160> NUMBER OF SEQ ID NOS: 81

<210> SEQ ID NO 1
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = any amino acid

<400> SEQUENCE: 1

Lys Xaa Xaa Xaa Asp
1               5

<210> SEQ ID NO 2
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = any amino acid

<400> SEQUENCE: 2

Asp Xaa Xaa Xaa Lys
1               5

<210> SEQ ID NO 3
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = any amino acid

<400> SEQUENCE: 3

Lys Xaa Xaa Xaa Glu
1               5

<210> SEQ ID NO 4
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = any amino acid

<400> SEQUENCE: 4

Glu Xaa Xaa Xaa Lys
1               5

<210> SEQ ID NO 5
<211> LENGTH: 5
<212> TYPE: PRT
<213> ORGANISM: Artificial
<220> FEATURE:
<223> OTHER INFORMATION: Synthetic
<220> FEATURE:

```
<221> NAME/KEY: MISC_FEATURE
<222> LOCATION: (1)..(1)
<223> OTHER INFORMATION: Xaa = Ornithine
<220> FEATURE:
<221> NAME/KEY: MISC_FEATURE
<222> LOCATION: (2)..(4)
<223> OTHER INFORMATION: Xaa = any amino acid

<400> SEQUENCE: 5

Xaa Xaa Xaa Xaa Asp
1               5

<210> SEQ ID NO 6
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Ornithine

<400> SEQUENCE: 6

Asp Xaa Xaa Xaa Xaa
1               5

<210> SEQ ID NO 7
<211> LENGTH: 6
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = any amino acid
<220> FEATURE:
<221> NAME/KEY: MISC_FEATURE
<222> LOCATION: (3)..(5)
<223> OTHER INFORMATION: Xaa = any amino acid

<400> SEQUENCE: 7

Xaa Lys Xaa Xaa Xaa Asp
1               5

<210> SEQ ID NO 8
<211> LENGTH: 5
<212> TYPE: PRT
<213> ORGANISM: Artificial
<220> FEATURE:
<223> OTHER INFORMATION: Synthetic

<400> SEQUENCE: 8

Lys Ala Arg Ala Asp
1               5

<210> SEQ ID NO 9
<211> LENGTH: 5
<212> TYPE: PRT
<213> ORGANISM: Artificial
<220> FEATURE:
<223> OTHER INFORMATION: Synthetic

<400> SEQUENCE: 9

Asp Ala Arg Ala Lys
1               5
```

```
<210> SEQ ID NO 10
<211> LENGTH: 5
<212> TYPE: PRT
<213> ORGANISM: Artificial
<220> FEATURE:
<223> OTHER INFORMATION: Synthetic

<400> SEQUENCE: 10

Lys Ala Arg Ala Glu
1               5

<210> SEQ ID NO 11
<211> LENGTH: 5
<212> TYPE: PRT
<213> ORGANISM: Artificial
<220> FEATURE:
<223> OTHER INFORMATION: Synthetic

<400> SEQUENCE: 11

Glu Ala Arg Ala Lys
1               5

<210> SEQ ID NO 12
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ornithine

<400> SEQUENCE: 12

Xaa Ala Arg Ala Asp
1               5

<210> SEQ ID NO 13
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa = Ornithine

<400> SEQUENCE: 13

Asp Ala Arg Ala Xaa
1               5

<210> SEQ ID NO 14
<211> LENGTH: 5
<212> TYPE: PRT
<213> ORGANISM: Artificial
<220> FEATURE:
<223> OTHER INFORMATION: Synthetic

<400> SEQUENCE: 14

Lys Ala Arg Ala Asp
1               5

<210> SEQ ID NO 15
<211> LENGTH: 5
<212> TYPE: PRT
<213> ORGANISM: Artificial
<220> FEATURE:
```

```
<223> OTHER INFORMATION: Synthetic

<400> SEQUENCE: 15

Lys Leu Leu Leu Asp
1               5

<210> SEQ ID NO 16
<211> LENGTH: 5
<212> TYPE: PRT
<213> ORGANISM: Artificial
<220> FEATURE:
<223> OTHER INFORMATION: Synthetic

<400> SEQUENCE: 16

Lys Leu Ala Leu Asp
1               5

<210> SEQ ID NO 17
<211> LENGTH: 5
<212> TYPE: PRT
<213> ORGANISM: Artificial
<220> FEATURE:
<223> OTHER INFORMATION: Synthetic

<400> SEQUENCE: 17

Lys Leu Phe Ala Asp
1               5

<210> SEQ ID NO 18
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ornithine

<400> SEQUENCE: 18

Xaa Ala Arg Ala Glu
1               5

<210> SEQ ID NO 19
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa = Ornithine

<400> SEQUENCE: 19

Glu Ala Arg Ala Xaa
1               5

<210> SEQ ID NO 20
<211> LENGTH: 5
<212> TYPE: PRT
<213> ORGANISM: Artificial
<220> FEATURE:
<223> OTHER INFORMATION: Synthetic

<400> SEQUENCE: 20

Lys Ala Arg Ala Asp
1               5
```

```
<210> SEQ ID NO 21
<211> LENGTH: 5
<212> TYPE: PRT
<213> ORGANISM: Artificial
<220> FEATURE:
<223> OTHER INFORMATION: Synthetic

<400> SEQUENCE: 21

Lys Ala Arg Ala Asp
1               5

<210> SEQ ID NO 22
<211> LENGTH: 5
<212> TYPE: PRT
<213> ORGANISM: Artificial
<220> FEATURE:
<223> OTHER INFORMATION: Synthetic

<400> SEQUENCE: 22

Lys Ala Arg Ala Asp
1               5

<210> SEQ ID NO 23
<211> LENGTH: 5
<212> TYPE: PRT
<213> ORGANISM: Artificial
<220> FEATURE:
<223> OTHER INFORMATION: Synthetic

<400> SEQUENCE: 23

Lys Ala Ala Ala Asp
1               5

<210> SEQ ID NO 24
<211> LENGTH: 5
<212> TYPE: PRT
<213> ORGANISM: Artificial
<220> FEATURE:
<223> OTHER INFORMATION: Synthetic

<400> SEQUENCE: 24

Lys Ala Leu Ala Asp
1               5

<210> SEQ ID NO 25
<211> LENGTH: 5
<212> TYPE: PRT
<213> ORGANISM: Artificial
<220> FEATURE:
<223> OTHER INFORMATION: Synthetic

<400> SEQUENCE: 25

Lys Ala Met Ala Asp
1               5

<210> SEQ ID NO 26
<211> LENGTH: 5
<212> TYPE: PRT
<213> ORGANISM: Artificial
<220> FEATURE:
<223> OTHER INFORMATION: Synthetic

<400> SEQUENCE: 26

Lys Ala Gln Ala Asp
1               5

<210> SEQ ID NO 27
```

```
<211> LENGTH: 5
<212> TYPE: PRT
<213> ORGANISM: Artificial
<220> FEATURE:
<223> OTHER INFORMATION: Synthetic

<400> SEQUENCE: 27

Lys Ala Phe Ala Asp
1               5

<210> SEQ ID NO 28
<211> LENGTH: 5
<212> TYPE: PRT
<213> ORGANISM: Artificial
<220> FEATURE:
<223> OTHER INFORMATION: Synthetic

<400> SEQUENCE: 28

Lys Ala Gly Ala Asp
1               5

<210> SEQ ID NO 29
<211> LENGTH: 5
<212> TYPE: PRT
<213> ORGANISM: Artificial
<220> FEATURE:
<223> OTHER INFORMATION: Synthetic

<400> SEQUENCE: 29

Lys Gly Ser Ala Asp
1               5

<210> SEQ ID NO 30
<211> LENGTH: 5
<212> TYPE: PRT
<213> ORGANISM: Artificial
<220> FEATURE:
<223> OTHER INFORMATION: Synthetic

<400> SEQUENCE: 30

Lys Ser Ser Ser Asp
1               5

<210> SEQ ID NO 31
<211> LENGTH: 5
<212> TYPE: PRT
<213> ORGANISM: Artificial
<220> FEATURE:
<223> OTHER INFORMATION: Synthetic

<400> SEQUENCE: 31

Lys Gly Gly Gly Asp
1               5

<210> SEQ ID NO 32
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = any amino acid

<400> SEQUENCE: 32

Lys Xaa Xaa Xaa Asp
1               5
```

```
<210> SEQ ID NO 33
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = any amino acid

<400> SEQUENCE: 33

Asp Xaa Xaa Xaa Lys
1               5

<210> SEQ ID NO 34
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = any amino acid

<400> SEQUENCE: 34

Lys Xaa Xaa Xaa Glu
1               5

<210> SEQ ID NO 35
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(4)
<223> OTHER INFORMATION: Xaa = any amino acid

<400> SEQUENCE: 35

Glu Xaa Xaa Xaa Lys
1               5

<210> SEQ ID NO 36
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ornithine
<220> FEATURE:
<221> NAME/KEY: MISC_FEATURE
<222> LOCATION: (2)..(4)
<223> OTHER INFORMATION: Xaa = any amino acid

<400> SEQUENCE: 36

Xaa Xaa Xaa Xaa Asp
1               5

<210> SEQ ID NO 37
<211> LENGTH: 5
<212> TYPE: PRT
<213> ORGANISM: Artificial
<220> FEATURE:
<223> OTHER INFORMATION: Synthetic
<220> FEATURE:
```

```
<221> NAME/KEY: MISC_FEATURE
<222> LOCATION: (2)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = Ornithine

<400> SEQUENCE: 37

Asp Xaa Xaa Xaa Xaa
1               5

<210> SEQ ID NO 38
<211> LENGTH: 5
<212> TYPE: PRT
<213> ORGANISM: Artificial
<220> FEATURE:
<223> OTHER INFORMATION: Synthetic

<400> SEQUENCE: 38

Lys Ala Arg Ala Asp
1               5

<210> SEQ ID NO 39
<211> LENGTH: 5
<212> TYPE: PRT
<213> ORGANISM: Artificial
<220> FEATURE:
<223> OTHER INFORMATION: Synthetic

<400> SEQUENCE: 39

Asp Ala Arg Ala Lys
1               5

<210> SEQ ID NO 40
<211> LENGTH: 5
<212> TYPE: PRT
<213> ORGANISM: Artificial
<220> FEATURE:
<223> OTHER INFORMATION: Synthetic

<400> SEQUENCE: 40

Lys Ala Arg Ala Glu
1               5

<210> SEQ ID NO 41
<211> LENGTH: 5
<212> TYPE: PRT
<213> ORGANISM: Artificial
<220> FEATURE:
<223> OTHER INFORMATION: Synthetic

<400> SEQUENCE: 41

Glu Ala Arg Ala Lys
1               5

<210> SEQ ID NO 42
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Ornithine

<400> SEQUENCE: 42

Xaa Ala Arg Ala Asp
```

```
<210> SEQ ID NO 43
<211> LENGTH: 5
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (5)..(5)
<223> OTHER INFORMATION: Xaa = Ornithine

<400> SEQUENCE: 43

Asp Ala Arg Ala Xaa
1               5

<210> SEQ ID NO 44
<211> LENGTH: 5
<212> TYPE: PRT
<213> ORGANISM: Artificial
<220> FEATURE:
<223> OTHER INFORMATION: Synthetic

<400> SEQUENCE: 44

Lys Ala Ala Ala Asp
1               5

<210> SEQ ID NO 45
<211> LENGTH: 5
<212> TYPE: PRT
<213> ORGANISM: Artificial
<220> FEATURE:
<223> OTHER INFORMATION: Synthetic

<400> SEQUENCE: 45

Lys Gly Ser Ala Asp
1               5

<210> SEQ ID NO 46
<211> LENGTH: 10
<212> TYPE: PRT
<213> ORGANISM: Artificial
<220> FEATURE:
<223> OTHER INFORMATION: Synthetic

<400> SEQUENCE: 46

Lys Ala Arg Ala Asp Lys Ala Arg Ala Asp
1               5                   10

<210> SEQ ID NO 47
<211> LENGTH: 15
<212> TYPE: PRT
<213> ORGANISM: Artificial
<220> FEATURE:
<223> OTHER INFORMATION: Synthetic

<400> SEQUENCE: 47

Lys Ala Arg Ala Asp Lys Ala Arg Ala Asp Lys Ala Arg Ala Asp
1               5                   10                  15

<210> SEQ ID NO 48
<211> LENGTH: 17
<212> TYPE: PRT
<213> ORGANISM: Artificial
<220> FEATURE:
<223> OTHER INFORMATION: Synthetic

<400> SEQUENCE: 48
```

```
Phe Gly Gly Phe Thr Gly Ala Arg Lys Ser Ala Arg Lys Leu Ala Asn
1               5                   10                  15

Gln

<210> SEQ ID NO 49
<211> LENGTH: 14
<212> TYPE: PRT
<213> ORGANISM: Artificial
<220> FEATURE:
<223> OTHER INFORMATION: Synthetic

<400> SEQUENCE: 49

Phe Gly Phe Thr Lys Ala Arg Lys Asp Lys Arg Lys Leu Asp
1               5                   10

<210> SEQ ID NO 50
<211> LENGTH: 15
<212> TYPE: PRT
<213> ORGANISM: Artificial
<220> FEATURE:
<223> OTHER INFORMATION: Synthetic

<400> SEQUENCE: 50

Gly Gly Gly Phe Thr Lys Ala Arg Lys Asp Lys Arg Lys Leu Asp
1               5                   10                  15

<210> SEQ ID NO 51
<211> LENGTH: 10
<212> TYPE: PRT
<213> ORGANISM: Artificial
<220> FEATURE:
<223> OTHER INFORMATION: Synthetic

<400> SEQUENCE: 51

Lys Ala Arg Lys Asp Lys Arg Lys Leu Asp
1               5                   10

<210> SEQ ID NO 52
<211> LENGTH: 5
<212> TYPE: PRT
<213> ORGANISM: Artificial
<220> FEATURE:
<223> OTHER INFORMATION: Synthetic

<400> SEQUENCE: 52

Lys Ala Arg Ala Asp
1               5

<210> SEQ ID NO 53
<211> LENGTH: 5
<212> TYPE: PRT
<213> ORGANISM: Artificial
<220> FEATURE:
<223> OTHER INFORMATION: Synthetic

<400> SEQUENCE: 53

Lys Ala Arg Ala Asp
1               5

<210> SEQ ID NO 54
<211> LENGTH: 10
<212> TYPE: PRT
<213> ORGANISM: Artificial
<220> FEATURE:
<223> OTHER INFORMATION: Synthetic

<400> SEQUENCE: 54
```

Lys Ala Arg Ala Asp Lys Ala Arg Ala Asp
1               5                   10

<210> SEQ ID NO 55
<211> LENGTH: 15
<212> TYPE: PRT
<213> ORGANISM: Artificial
<220> FEATURE:
<223> OTHER INFORMATION: Synthetic

<400> SEQUENCE: 55

Lys Ala Arg Ala Asp Lys Ala Arg Ala Asp Lys Ala Arg Ala Asp
1               5                   10                  15

<210> SEQ ID NO 56
<211> LENGTH: 12
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = hydrophobic amino acid
<220> FEATURE:
<221> NAME/KEY: MISC_FEATURE
<222> LOCATION: (2)..(4)
<223> OTHER INFORMATION: Xaa = any amino acid
<220> FEATURE:
<221> NAME/KEY: MISC_FEATURE
<222> LOCATION: (5)..(5)
<223> OTHER INFORMATION: Xaa = hydrophobic amino acid
<220> FEATURE:
<221> NAME/KEY: MISC_FEATURE
<222> LOCATION: (6)..(7)
<223> OTHER INFORMATION: Xaa = any amino acid
<220> FEATURE:
<221> NAME/KEY: MISC_FEATURE
<222> LOCATION: (8)..(8)
<223> OTHER INFORMATION: Xaa = hydrophobic amino acid
<220> FEATURE:
<221> NAME/KEY: MISC_FEATURE
<222> LOCATION: (9)..(9)
<223> OTHER INFORMATION: Xaa = any amino acid
<220> FEATURE:
<221> NAME/KEY: MISC_FEATURE
<222> LOCATION: (10)..(10)
<223> OTHER INFORMATION: Xaa = negatively charged amino acid
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (12)..(12)
<223> OTHER INFORMATION: Xaa = hydrophobic amino acid

<400> SEQUENCE: 56

Xaa Xaa Xaa Xaa Xaa Xaa Xaa Xaa Xaa Xaa Xaa Xaa
1               5                   10

<210> SEQ ID NO 57
<211> LENGTH: 12
<212> TYPE: PRT
<213> ORGANISM: Artificial
<220> FEATURE:
<223> OTHER INFORMATION: Synthetic

<400> SEQUENCE: 57

Tyr Lys Arg Glu Leu Asp Lys Met Ala Asp Asp Phe
1               5                   10

```
<210> SEQ ID NO 58
<211> LENGTH: 12
<212> TYPE: PRT
<213> ORGANISM: Artificial
<220> FEATURE:
<223> OTHER INFORMATION: Synthetic

<400> SEQUENCE: 58

Val Lys Arg Gln Leu Asp Lys Ile Ala Asp Asp Ile
1               5                   10

<210> SEQ ID NO 59
<211> LENGTH: 11
<212> TYPE: PRT
<213> ORGANISM: Artificial
<220> FEATURE:
<223> OTHER INFORMATION: Synthetic

<400> SEQUENCE: 59

Lys Ala Gln Glu Asp Lys Val Ala Asp Asp Met
1               5                   10

<210> SEQ ID NO 60
<211> LENGTH: 11
<212> TYPE: PRT
<213> ORGANISM: Artificial
<220> FEATURE:
<223> OTHER INFORMATION: Synthetic

<400> SEQUENCE: 60

Lys Ala Gln Glu Asp Lys Ile Ala Asp Asp Phe
1               5                   10

<210> SEQ ID NO 61
<211> LENGTH: 10
<212> TYPE: PRT
<213> ORGANISM: Artificial
<220> FEATURE:
<223> OTHER INFORMATION: Synthetic

<400> SEQUENCE: 61

Lys Arg Glu Leu Asp Lys Met Ala Asp Asp
1               5                   10

<210> SEQ ID NO 62
<211> LENGTH: 10
<212> TYPE: PRT
<213> ORGANISM: Artificial
<220> FEATURE:
<223> OTHER INFORMATION: Synthetic

<400> SEQUENCE: 62

Lys Arg Gln Leu Asp Lys Ile Ala Asp Asp
1               5                   10

<210> SEQ ID NO 63
<211> LENGTH: 10
<212> TYPE: PRT
<213> ORGANISM: Artificial
<220> FEATURE:
<223> OTHER INFORMATION: Synthetic

<400> SEQUENCE: 63

Lys Ala Gln Glu Asp Lys Val Ala Asp Asp
1               5                   10

<210> SEQ ID NO 64
<211> LENGTH: 10
```

```
<212> TYPE: PRT
<213> ORGANISM: Artificial
<220> FEATURE:
<223> OTHER INFORMATION: Synthetic

<400> SEQUENCE: 64

Lys Ala Gln Glu Asp Lys Ile Ala Asp Asp
1               5                   10

<210> SEQ ID NO 65
<211> LENGTH: 8
<212> TYPE: PRT
<213> ORGANISM: Artificial
<220> FEATURE:
<223> OTHER INFORMATION: Synthetic

<400> SEQUENCE: 65

Leu Arg Lys Met Ala Asp Asp Phe
1               5

<210> SEQ ID NO 66
<211> LENGTH: 8
<212> TYPE: PRT
<213> ORGANISM: Artificial
<220> FEATURE:
<223> OTHER INFORMATION: Synthetic

<400> SEQUENCE: 66

Leu Ala Lys Ile Ala Asp Asp Ile
1               5

<210> SEQ ID NO 67
<211> LENGTH: 8
<212> TYPE: PRT
<213> ORGANISM: Artificial
<220> FEATURE:
<223> OTHER INFORMATION: Synthetic

<400> SEQUENCE: 67

Leu Ala Lys Val Ala Asp Asp Ile
1               5

<210> SEQ ID NO 68
<211> LENGTH: 8
<212> TYPE: PRT
<213> ORGANISM: Artificial
<220> FEATURE:
<223> OTHER INFORMATION: Synthetic

<400> SEQUENCE: 68

Leu Ala Lys Ile Ala Asp Asp Phe
1               5

<210> SEQ ID NO 69
<211> LENGTH: 5
<212> TYPE: PRT
<213> ORGANISM: Artificial
<220> FEATURE:
<223> OTHER INFORMATION: Synthetic

<400> SEQUENCE: 69

Lys Met Ala Asp Asp
1               5

<210> SEQ ID NO 70
<211> LENGTH: 5
<212> TYPE: PRT
<213> ORGANISM: Artificial
```

```
<220> FEATURE:
<223> OTHER INFORMATION: Synthetic

<400> SEQUENCE: 70

Lys Ile Ala Asp Asp
1               5

<210> SEQ ID NO 71
<211> LENGTH: 5
<212> TYPE: PRT
<213> ORGANISM: Artificial
<220> FEATURE:
<223> OTHER INFORMATION: Synthetic

<400> SEQUENCE: 71

Lys Val Ala Asp Asp
1               5

<210> SEQ ID NO 72
<211> LENGTH: 5
<212> TYPE: PRT
<213> ORGANISM: Artificial
<220> FEATURE:
<223> OTHER INFORMATION: Synthetic

<400> SEQUENCE: 72

Lys Met Ala Asp Asp
1               5

<210> SEQ ID NO 73
<211> LENGTH: 6
<212> TYPE: PRT
<213> ORGANISM: Artificial
<220> FEATURE:
<223> OTHER INFORMATION: Synthetic

<400> SEQUENCE: 73

Phe Met Lys Glu Asp Leu
1               5

<210> SEQ ID NO 74
<211> LENGTH: 4
<212> TYPE: PRT
<213> ORGANISM: Artificial
<220> FEATURE:
<223> OTHER INFORMATION: Synthetic

<400> SEQUENCE: 74

Met Lys Glu Asp
1

<210> SEQ ID NO 75
<211> LENGTH: 3
<212> TYPE: PRT
<213> ORGANISM: Artificial
<220> FEATURE:
<223> OTHER INFORMATION: Synthetic

<400> SEQUENCE: 75

Lys Glu Asp
1

<210> SEQ ID NO 76
<211> LENGTH: 15
<212> TYPE: PRT
<213> ORGANISM: Artificial
<220> FEATURE:
<223> OTHER INFORMATION: Synthetic
```

```
<400> SEQUENCE: 76

Phe Gly Gly Phe Thr Lys Ala Arg Lys Asp Lys Arg Lys Leu Asp
1               5                   10                  15

<210> SEQ ID NO 77
<211> LENGTH: 15
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa = Nphe

<400> SEQUENCE: 77

Xaa Gly Gly Phe Thr Lys Ala Arg Lys Asp Lys Arg Lys Leu Asp
1               5                   10                  15

<210> SEQ ID NO 78
<211> LENGTH: 11
<212> TYPE: PRT
<213> ORGANISM: Artificial
<220> FEATURE:
<223> OTHER INFORMATION: Synthetic

<400> SEQUENCE: 78

Thr Lys Ala Arg Lys Asp Lys Arg Lys Leu Asp
1               5                   10

<210> SEQ ID NO 79
<211> LENGTH: 10
<212> TYPE: PRT
<213> ORGANISM: Artificial
<220> FEATURE:
<223> OTHER INFORMATION: Synthetic

<400> SEQUENCE: 79

Lys Ala Arg Lys Asp Lys Arg Lys Leu Asp
1               5                   10

<210> SEQ ID NO 80
<211> LENGTH: 13
<212> TYPE: PRT
<213> ORGANISM: Artificial
<220> FEATURE:
<223> OTHER INFORMATION: Synthetic

<400> SEQUENCE: 80

Phe Gly Gly Phe Thr Gly Ala Arg Lys Ser Ala Arg Lys
1               5                   10

<210> SEQ ID NO 81
<211> LENGTH: 9
<212> TYPE: PRT
<213> ORGANISM: Artificial
<220> FEATURE:
<223> OTHER INFORMATION: Synthetic

<400> SEQUENCE: 81

Thr Gly Ala Arg Lys Ser Ala Arg Lys
1               5
```

ALPHA HELICAL MIMICS, THEIR USES AND METHODS FOR THEIR PRODUCTION

CROSS-REFERENCE TO RELATED APPLICATIONS

This application is a divisional of co-pending U.S. patent application Ser. No. 10/593,407, filed Jan. 29, 2007, which is a §371 US National Entry of International Application No. PCT/AU2005/000400, filed Mar. 21, 2005, which claims priority to Australian Patent Application No. 2004901447, filed Mar. 19, 2004, each of which is incorporated herein by reference.

FIELD OF THE INVENTION

This invention relates generally to short chain peptides that have been constrained to adopt an alpha helical conformation and to their use as alpha helical scaffolds for directing amino acid side chains into positions analogous to those found in longer chain alpha helical peptides and for attaching peptidic or non-peptidic appendages in order to mimic side chains of longer alpha helical peptides. More particularly the invention relates to alpha helical cyclic pentapeptides and their use as alpha helical scaffolds or macrocyclic alpha helical modules, either alone, or within longer chain peptides or attached to other macrocyclic peptides or attached to non-peptidic structures, for the purpose of mimicking naturally occurring peptides or proteins, and as agonists or antagonists of the biological activity of naturally-occurring peptides or proteins or for the preparation of new materials.

Bibliographic details of the publications numerically referred to in this specification are collected at the end of the description.

BACKGROUND OF THE INVENTION

The alpha helix is a fundamental structural unit in the fabric of proteins, with 30% of all amino acids in proteins occurring in alpha helices.[1] When helical sequences of amino acids are exposed on an exterior surface of a protein, the helix frequently interacts with another protein, a segment of DNA or of RNA.[2,3] This biomolecular recognition is central to a large range of biological processes, for example those summarized in Table 1. In most cases however only a few alpha helical turns are actually involved in the molecular recognition. For example, transcriptional regulators (e.g. p53, NF-kBp65, VP16c)[4-6] apoptosis regulators (e.g. Bak)[7] and RNA-transporter proteins (e.g. Rev)[8] all contain a short alpha helical sequence of only 2-4 turns that mediates function by direct interaction with a receptor.

TABLE 1

Some Biological Processes Mediated by Interaction of Alpha-Helices with Other Biomolecules

| α-Helical Peptide | Biological target | Process Mediated | Reference |
|---|---|---|---|
| Protein-DNA interactions | | | |
| Zif268 | G/C rich major groove | DNA transcription | 9 |
| Protein-RNA interactions | | | |
| HIV Reverse Transcriptase | Rev Response Element (RRE) | RNA reverse transcription | 10 |
| λ-N peptide | BoxB RNA | Transcriptional anti-termination | 10 |

TABLE 1-continued

Some Biological Processes Mediated by Interaction of Alpha-Helices with Other Biomolecules

| α-Helical Peptide | Biological target | Process Mediated | Reference |
|---|---|---|---|
| P22 peptides | BoxB RNA | Transcriptional anti-termination | 10 |
| Protein-Protein interactions | | | |
| p53 | HDM2 | Tumor Suppressor silencing | 4 |
| Bak | Bcl-$X_L$ | Apoptosis Regulation | 7 |
| VHL peptide | Elongin C | DNA transcription | 11 |
| VP16 activation domain | $HTAF_{II}31$ | DNA transcription | 12 |
| hPTH | hPTHrP | Calcium homeostasis | 13 |
| Dynorphin A | κ,δ-Opioid receptors | Pain signal transmission | 14, 15 |
| Apolipoprotein-E | LDL receptor | Lipid metabolism, cholesterol homeostasis | 16 |
| Neuropeptide-Y | NPY receptors | Multiple functions | 17 |
| Galanin | Gal receptors | Multiple functions | 18 |
| Corticotropin Releasing Factor | CRF receptors | Stress responses | 19 |
| Calcitonin Gene Related Peptide | CGRP receptors | Multiple functions | 20 |
| Nociceptin | ORL1 receptor | Pain transmission | |
| Vasointestinal Peptide | $VPAC_{1\&2}$ | Multiple functions | 21 |
| Nuclear Coactivators (eg. SRC1, GRIP1) | Nuclear Receptors | DNA Transcription | 22, 23 |

Short peptide sequences of less than 15 amino acid residues that correspond to these helical protein regions are not thermodynamically stable structures in water when removed from their protein environments.[24,25] Short synthetic peptides corresponding to such alpha helical recognition motifs tend not to display appreciable helical structure in water, away from the helix-stabilizing hydrophobic environments of proteins. If short peptide alpha helices could be stabilized or mimicked by small molecules, such compounds might be valuable chemical or biological probes and lead to development of novel pharmaceuticals, vaccines, diagnostics, biopolymers, and industrial agents. The goal of structurally mimicking short alpha helices with small molecules that have biological activity comparable to proteins has not yet been realized.

Attempts to stabilize short alpha helical peptides have met with limited success to date. Examples of methods used to stabilize alpha helicity in peptides longer than 15 residues are helix-nucleating templates[26-29], metals[30-35], unnatural amino acids[36,37], non-covalent side chain constraints[38,39] and covalent side chain linkers (e.g. disulfide-[40,41], hydrazone-[42], lactam-[43-50], aliphatic linkers[51-53]). Although mimics of short alpha helical segments have remained elusive, some recent attempts have been reported using non-peptidic oligoamide and terphenyl scaffolds that project 2-3 substituents into similar three dimensional space as the side chains of an alpha helix[54-56].

Helix nucleating templates are organic molecules at the N- or C-terminus of a peptide which can make hydrogen bonds with the first or last four NH or C=O groups in the peptide, and thus nucleate helicity throughout the rest of the peptide. Such a task is not trivial due to the specific position, pitch and orientation of the required NH or C=O groups. Several attempts have had some success, these include Kemp's triacid, cyclic proline molecules,[26,57-61] Mueller's Cage compound[62], Bartlett's cap[28], and Kahn's cap[63]. There have also been some attempts to synthesize capping groups by replacing a hydrogen bond with a covalent link as in the case of Satterthwait's cap[64].

Transition metals[30-35] are often found in proteins serving both catalytic and structural roles. By exploiting the ability of transition metals such as $Cu^{2+}$, $Zn^{2+}$, $Cd^{2+}$, $Ru^3$, $Pd^{2+}$ to bind both acidic and basic residues it has been possible to achieve helix stabilization. Chelation of metals to donor groups generally yields ~1 kcal/mol$^{-1}$ in helix stabilization, however stabilization is very dependent on solvent, salt concentration and pH.

Unnatural amino acids have also been reported to favor helix stabilization. In general n-alkyl substitution, α,α- and γγ-disubstitution increases helix stability. β,β-Disubstitution reduces helicity, and β-tertiary substitution totally abolishes helix propensity, thus it appears the helix is quite sensitive to steric effects at the beta position[65]. α-Aminoisobutyric acid (Aib) in particular is known to stabilize α- and $3_{10}$-helical conformations and has been used to improve the biological activity of several peptides. Nociceptin analogues containing 1 or 2 Aib residues resulted in 10-15 fold increases in potency and affinity ($K_i$=0.02 nM)[66]. Similarly an analogue of p53 containing Aib and 1-aminocyclopropanecarboxylic acid ($Ac_3c$) yielded a peptide 1735 more active than the native peptide[67]. Finally when Aib was substituted into deltorphin-C analogues a 10-fold $K_i$ increase in selectivity was obtained for δ vs μ opioid receptor subtypes[68].

Disulfide bridges have been employed to stabilize helices via two methods. The first involves the use of a modified, unnatural amino acid D,L 2-amino-6-mercaptohexanoic acid placed at the $i^{th}$ (D) and $i+7^{th}$ (L) residues to stabilize two turns of an alpha helix[41]. The second approach involves using a D-cysteine (i) and L-cysteine (i+3) disulfide to stabilize a single alpha helical turn. This approach was successful to a certain extent, however the conformation was quite solvent dependent[40]. It has recently been reported that this approach was used to constrain the SRC-1 peptide, which is known to adopt an alpha helical conformation in the estrogen receptor-α, and inhibit this receptor with a $K_i$ of 25 nM[69]

Lactam bridges have often been used to increase helicity and turn conformations in long peptides. They generally involve the covalent amide linkage of the side chains of lysine/ornithine residues with the side chains of aspartic/glutamic acid residues at either i to i+3 or i to i+4 positions. These constraints although initially examined in model peptides have been applied to numerous biological targets in which the bioactive conformation is deemed to be helical. In general this constraint has been employed in relatively long sequences (15-30 residues) generally to create monocyclic analogues, but in some cases, up to three lactam bridges have been included. Some examples of their use include PTH, NPY, CRF, GCN4, Galanin and Dynorphin-A. Despite their inception over 10 years ago, there is still a lack of consensus over which residue combinations are the best, although it appears i to i+4 spacing is optimal for alpha helicity. Early pioneering work by Taylor[48] suggested Lys→Asp was the optimal combination, however, later work by Houston identified Glu→Lys as optimal, although this study totally neglected to use aspartic acid[70]. More recent work by Taylor has involved using overlapping lactam bridges to yield a highly rigid hexapeptide alpha helix, highly resistant to chemical and thermal degradation[45], and with some templating capability[71]. However, this hexapeptide scaffold is limited for general application as a template since only two of six residues are available for interaction with a biological target. The synthesis and properties of side-chain lactam bridged peptides, their alpha helical nature, functional activity and potential for improved proteolysis resistance has recently been reviewed[43].

Modified lactam-type bridges can also be spaced i to i+7, therefore requiring longer linkers, and in this regard, aspartic/glutamic acid, and/or diaminopropionic acid residues provide a convenient functionality to which linkers can be attached. Some of these have included diaminopentane linkers joined to two glutamic acids[53], 4-(aminomethyl)-phenylacetic acid linked via aspartic acid and 1,3-diaminopropionic acid[49], or alternately 4-(aminomethyl)-phenylazobenzoic acid joined to the N- and C-terminus of an octapeptide. The two former methods resulted in reasonably stable helices, whilst the latter resulted in a $3_{10}$ helical/random coil conformation depending on the cis/trans isomerization of the azo linkage.

Ring closing metathesis has been used in helix stabilization. Pioneered by Grubbs[72], this approach has been utilized with allyl-modified serine/homoserine residues in i→i+4 fashion. It has not been overly successful in stabilizing alpha helicity, although some $3_{10}$ stabilization was observed. Other approaches have incorporated both S- and R-α-methyl-α-allylglycine, along with the α-homoallyl and α-homo-homoallyl derivatives, positioned at either i→i+4 or i→i+7[51]. It was found that the R-isomer at the i position and the S-isomer at the i+7 position, with an 11 carbon link provided 44% helix stability compared to the uncyclized peptide.

Non-peptidic mimicry of alpha helices has been rare, with only a few examples reported. The first reported non-peptidic helix mimetics were 1,1,6-trisubstituted indanes, that when coupled to an amino acid were capable of presenting three side chains in a helical like conformation. When applied as tachykinin mimetics, they had micromolar affinity for NK and $NK_3$ receptors[73]. These type of molecules were recently applied to magainin mimicry, and whilst they were capable of killing bacterial strains they still maintained high hemolytic activity[74]. Recently Kahne and co-workers developed a pentasaccharide helix mimetic based on GCN4 which bound DNA with micromolar affinity[75]. By far the most successful approach to non-peptidic alpha helix mimicry has been achieved by Hamilton and co-workers who have successfully developed two generic types of molecules—terphenyls and oligoamides capable of mimicking the i, i+4, i+7 side chains on one face of an alpha helix. These mimetics have been successfully applied to inhibition of HIV gp41 mediated viral fusion with an $IC_{50}$ of 15.7 μg/mL[76], and also inhibit Bak/Bcl-$X_L$ complex with low micromolar to nanomolar efficiency[77,78].

There have been no previous reports of cyclic pentapeptides adopting alpha helices on their own. Usually cyclic pentapeptides have been used to mimic the smaller beta or gamma turns of peptides and proteins. There are numerous examples of cyclic peptides that mimic beta or gamma turns reported in the literature as demonstrated by several reviews[73-81]. A prime example is synthetic compound 1 which is a cyclic pentapeptide containing the RGD tripeptide sequence. This compound is a potent glycoprotein IIb/IIIa antagonist and orally bioavailable antithrombotic and antitumor agent[73,82,83]. Compound 1 provides a demonstration of how the simple insertion into a cyclopeptide of a rigid amino acid as a conformational constraint can result in favorable biological and pharmacological properties; and a number of its derivatives are in advanced clinical trials. For example, in phase III clinical trials, the cyclic RGD-containing heptapeptide drug eptifibatide (Integrilin) has been shown to reduce the incidence of cardiac events in patients at risk of abrupt vessel closure after coronary angioplasty[84].

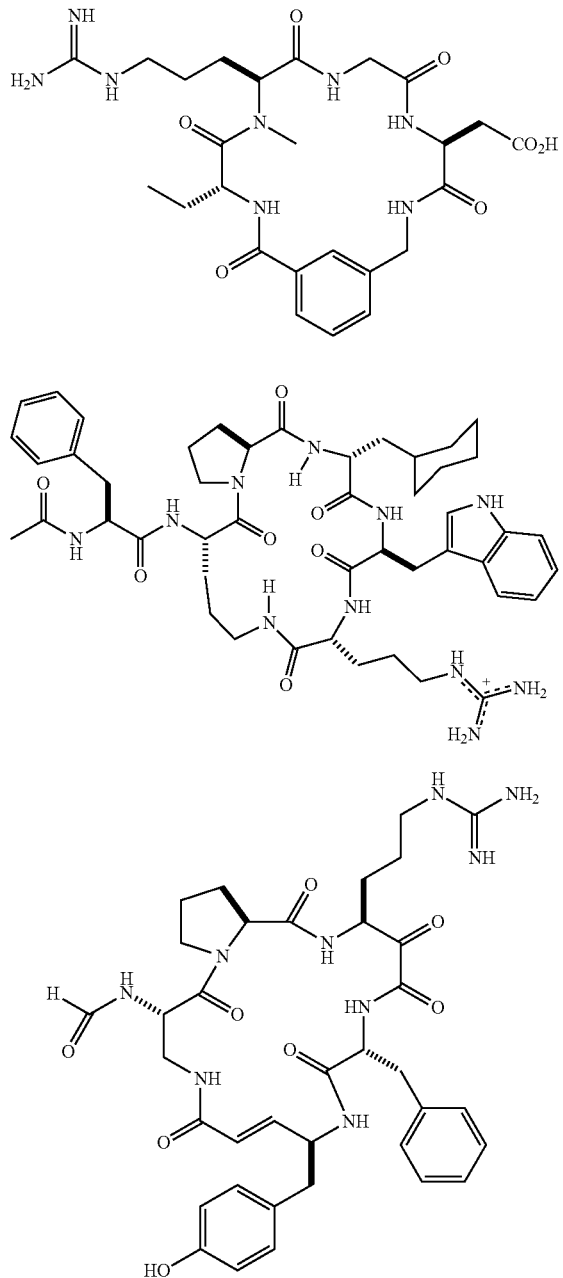

Constraints do not need to be complex, as shown in compound 2 where an ornithine (or lysine) side chain is used to form the macrocycle. This constraint, in conjunction with proline and D-cyclohexylalanine constraints, induces intramolecular hydrogen bonding that confers potent antagonism ($IC_{50}$ 10 nM) against human C5a receptors on polymorphonuclear leukocytes both in vitro and in vivo[85]. C5a antagonists are expected to be useful for combating inflammatory diseases.

Cyclotheonamide A (Compound 3) is a 19-membered cyclic pentapeptide possessing α-keto amide and trans-4-aminobutenoyl constraints. It was isolated from the marine sponge Theonella sp. and was shown to inhibit the serine proteases thrombin (Ki 180 nM) and trypsin (Ki 23 nM). The NMR solution structure of compound 3 was recently found to be the same in water as those found in the solid state when bound to trypsin and thrombin[86], suggesting that this natural product is pre-organized for enzyme binding, and that selectivity is associated with the positioning of the D-Phe side chain.

Lactam bridges (i→i+3, i→i+4, i→i+7) have previously been reported to increase alpha helicity in longer peptides, although the literature is very inconsistent about their capacity to do so[43–51]. There have been no reports of cyclic pentapeptides adopting alpha helical structures.

The synthesis and conformation of multicyclic alpha helical peptides comprising three repeats of a heptapeptide constrained by a side-chain to side-chain lactam bridge in (i)→(i+4) positions has been reported[48,114]. These studies showed that spaced cyclic moieties in a peptide can induce or stabilize alpha helicity.

Conformational restrictions in the form of (i)→(i+4) lactam bridges incorporated into known peptide sequences to induce helical conformation have also been reported[115]. Three constrained helical 31-residue peptides derived from human parathyroid hormone and containing 1, 2 or 3 cyclic moieties were shown to be potent agonists of the parathyroid hormone and parathyroid hormone-related protein receptor There are few studies that report alpha helicity for the theoretical minimum (pentapeptide) sequence needed to define a beta turn, the existence and properties of which are not well defined despite the likelihood that only one or a few turns of a protein helix need to be mimicked for agonist/antagonist biological activity.

There are many commercially important peptides that are known to adopt alpha helical structures that would benefit from improved structural stabilization and improved resistance to proteolysis. Some examples include calcitonin which has been launched for the treatment of osteoporosis, the parathyroid hormone which is in phase II clinical trials for the treatment of osteoporosis, a substance-P/saporin conjugate which is in preclinical trials for the treatment of pain and conantokin-G which is under development for the treatment of epilepsy (Pharmaprojects, 2004).

Accordingly, there is a need for stabilized short peptide alpha helices that can mimic biological molecules or that can be incorporated into non-peptidic or semi-peptidic compounds to mimic biological molecules. Such peptides could potentially be valuable as chemical and biological probes, pharmaceuticals, biotechnology products such as vaccines, or diagnostic agents, new components of biopolymers and industrial agents.

SUMMARY OF THE INVENTION

This invention is predicated in part on the unexpected discovery that certain short chain peptides, which comprise at least one macrocyclic pentapeptide unit, are highly alpha helical in their own right in water even when subjected to denaturing conditions (e.g., 8M guanidine.HCl; trypsin; human plasma). Based on this discovery, the present invention resides in novel alpha helical compounds and non peptidic structures, which use one or more such cyclic pentapeptides or their analogues as alpha helical scaffolds that can project additional peptidic, cyclic, and non-peptidic appendages into positions typical of side chains of alpha helical peptides and protein segments. The present invention is also directed to methods for their preparation and use, as described hereinafter.

DETAILED DESCRIPTION OF THE INVENTION

Unless defined otherwise, all technical and scientific terms used herein have the same meaning as commonly understood by those of ordinary skill in the art to which the invention belongs. Although any methods and materials similar or equivalent to those described herein can be used in the practice or testing of the present invention, preferred methods and materials are described. For the purposes of the present invention, the following terms are defined below.

The articles "a" and "an" are used herein to refer to one or to more than one (i.e. to at least one) of the grammatical object of the article. By way of example, "an element" means one element or more than one element.

Throughout this specification and the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

Advantageously, at least one embodiment of the present invention provides compounds comprising at least one macrocyclic moiety, particularly a cyclic pentapeptide moiety, which has surprising alpha helicity in water, even under strong protein denaturing conditions such as high temperature (e.g., 40 to 80° C.), or the presence of up to 8M guanidine hydrochloride, or the presence of proteolytic enzymes such as trypsin.

According to one aspect of the present invention there is provided a compound comprising at least one alpha helical cyclic peptide, wherein the peptide consists essentially of a sequence of five amino acid residues having a first terminal residue and a second terminal residue that are separated by an intervening sequence of three amino acid residues, and wherein the side chains of the first and second terminal residues are linked to each other, with the proviso that when the compound comprises a single cyclic peptide it is selected from a compound that consists essentially of the single peptide or a compound that comprises the single peptide and a non-peptide moiety or a compound that comprises the single peptide and at least one other peptide that comprises at least one amino acid whose side chain has been derivatized and that when the compound comprises two or more cyclic peptides, at least two of these are located immediately adjacent to each other.

As used herein "alpha helical" refers to a three dimensional structural conformation which is analogous to those found in proteins and polypeptides. The alpha helix conformation found in naturally occurring proteins and polypeptides has its side chains extending to the outside of the structure, has a complete turn every 3.6 amino acids, is right-handed and typically has hydrogen bonding between the carbonyl groups of the amide bond and an amide N—H group 4 amino acids further on in the sequence. The cyclic peptides of the present invention have a helicity calculated from molar elipticities obtained from circular dichroism spectroscopy (CD spectroscopy) and are expressed as a percentage of the theoretical helicity obtainable for that peptide or a relative helicity compared to a reference standard or standard helix.

As used herein, the term "amino acid" refers to compounds having an amino group and a carboxylic acid group. An amino acid may be a naturally occurring amino acid or non-naturally occurring amino acid and may be a proteogenic amino acid or a non-proteogenic amino acid. The amino acids incorporated into the amino acid sequences of the present invention may be L-α-amino acids, D-α-amino acids or mixtures thereof.

In some embodiments, the cyclic peptides of the invention are linked directly or indirectly to non-peptide moieties. Such moieties include, but are not limited to, aldehydes, toxins; drugs; polysaccharides; nucleotides; oligonucleotides; labels such as radioactive substances (e.g. $^{111}$In, $^{125}$I, $^{131}$I, $^{99m}$Tc, $^{212}$B, $^{90}$Y, $^{86}$Rh); biotin; fluorescent tags; imaging reagents (e.g., those described in U.S. Pat. No. 4,741,900 and U.S. Pat. No. 5,326,856); hydrocarbon linkers (e.g., an alkyl group or derivative thereof) conjugated to a moiety providing for attachment to a solid substratum, or to a moiety providing for easy separation or purification (e.g., a hapten recognized by an antibody bound to a magnetic bead), etc. Linkage of the peptide to the non-peptide moiety may be by any of several well-known methods in the art.

Suitable naturally occurring proteogenic amino acids are shown in Table 2 together with their one letter and three letter codes.

TABLE 2

| Amino Acid | one letter code | three letter code |
| --- | --- | --- |
| L-alanine | A | Ala |
| L-arginine | R | Arg |
| L-asparagine | N | Asn |
| L-aspartic acid | D | Asp |
| L-cysteine | C | Cys |
| L-glutamine | Q | Gln |
| L-glutamic acid | E | Glu |
| glycine | G | Gly |
| L-histidine | H | His |
| L-isoleucine. | I | Ile |
| L-leucine | L | Leu |
| L-lysine | K | Lys |
| L-methionine | M | Met |
| L-phenylalanine | F | Phe |
| L-proline | P | Pro |
| L-serine | S | Ser |
| L-threonine | T | Thr |
| L-tryptophan | W | Trp |
| L-tyrosine | Y | Tyr |
| L-valine | V | Val |

Suitable non-proteogenic or non-naturally occurring amino acids may be prepared by side chain modification or by total synthesis. Examples of side chain modifications contemplated by the present invention include, but are not limited to modifications of amino groups such as by reductive alkylation by reaction with an aldehyde followed by reduction with NaBH$_4$; amidination with methylacetimidate; acylation with acetic anhydride; carbamoylation of amino groups with cyanate; trinitrobenzylation of amino groups with 2,4,6-trinitrobenzene sulphonic acid (TNBS); acylation of amino groups with succinic anhydride and tetrahydrophthalic anhydride; and pyridoxylation of lysine with pyridoxal-5-phosphate followed by reduction with NaBH$_4$.

The guanidine group of arginine residues may be modified by the formation of heterocyclic condensation products with reagents such as 2,3-butanedione, phenylglyoxal and glyoxal.

The carboxyl group may be modified by carbodiimide activation via O-acylisourea formation followed by subsequent derivatisation, for example, to a corresponding amide.

Sulfhydryl groups may be modified by methods such as carboxymethylation with iodoacetic acid or iodoacetamide; performic acid oxidation to cysteic acid; formation of a mixed disulfides with other thiol compounds; reaction with maleimide, maleic anhydride or other substituted maleimide; formation of mercurial derivatives using 4-chloromercuribenzoate, 4-chloromercuriphenylsulfonic acid, phenylmercury chloride, 2-chloromercuri-4-nitrophenol and other mercurials; carbamoylation with cyanate at alkaline pH.

Tryptophan residues may be modified by, for example, oxidation with N-bromosuccinimide or alkylation of the indole ring with 2-hydroxy-5-nitrobenzyl bromide or sulfenyl halides. Tyrosine residues on the other hand, may be altered by nitration with tetranitromethane to form a 3-nitrotyrosine derivative.

Modification of the imidazole ring of a histidine residue may be accomplished by alkylation with iodoacetic acid derivatives or N-carboethoxylation with diethylpyrocarbonate.

Examples of incorporating unnatural amino acids and derivatives during protein synthesis include, but are not limited to, use of norleucine, t-butylglycine, norvaline, phenylglycine, ornithine, sarcosine, 2-thienyl alanine and/or D-isomers of amino acids. Examples of suitable non-proteogenic or non-naturally occurring amino acids contemplated herein is shown in Table 3.

TABLE 3

| Non-conventional amino acid | Code | Non-conventional amino acid | Code |
|---|---|---|---|
| α-aminobutyric acid | Abu | L-N-methylalanine | Nmala |
| α-amino-α-methylbutyrate | Mgabu | L-N-methylarginine | Nmarg |
| aminocyclopropane-carboxylate | Cpro | L-N-methylasparagine | Nmasn |
| L-N-methylaspartic acid | Nmasp | L-N-methylcysteine | Nmcys |
| aminonorbornyl-carboxylate | Norb | L-N-methylglutamine | Nmgln |
| cyclohexylalanine | Chexa | L-N-methylglutamic acid | Nmglu |
| cyclopentylalanine | Cpen | L-N-methylhistidine | Nmhis |
| D-alanine | Dal | L-N-methylisolleucine | Nmile |
| D-arginine | Darg | L-N-methylleucine | Nmleu |
| D-aspartic acid | Dasp | L-N-methyllysine | Nmlys |
| D-cysteine | Dcys | L-N-methylmethionine | Nmmet |
| D-glutamine | Dgln | L-N-methylnorleucine | Nmnle |
| D-glutamic acid | Dglu | L-N-methylnorvaline | Nmnva |
| D-histidine | Dhis | L-N-methylornithine | Nmorn |
| D-isoleucine | Dile | L-N-methylphenylalanine | Nmphe |
| D-leucine | Dleu | L-N-methylproline | Nmpro |
| D-lysine | Dlys | L-N-methylserine | Nmser |
| D-methionine | Dmet | L-N-methylthreonine | Nmthr |
| D-ornithine | Dorn | L-N-methyltryptophan | Nmtrp |
| D-phenylalanine | Dphe | L-N-methyltyrosine | Nmtyr |
| D-proline | Dpro | L-N-methylvaline | Nmval |
| D-serine | Dser | L-N-methylethylglycine | Nmetg |
| D-threonine | Dthr | L-N-methyl-t-butylglycine | Nmtbug |
| D-tryptophan | Dtrp | L-norleucine | Nle |
| D-tyrosine | Dtyr | L-norvaline | Nva |
| D-valine | Dval | α-methyl-aminoisobutyrate | Maib |
| D-α-methylalanine | Dmala | α-methyl--aminobutyrate | Mgabu |
| D-α-methylarginine | Dmarg | α-methylcyclohexylalanine | Mchexa |
| D-α-methylasparagine | Dmasn | α-methylcylcopentylalanine | Mcpen |
| D-α-methylaspartate | Dmasp | α-methyl-α-napthylalanine | Manap |
| D-α-methylcysteine | Dmcys | α-methylpenicillamine | Mpen |
| D-α-methylglutamine | Dmgln | N-(4-aminobutyl)glycine | Nglu |
| D-α-methylhistidine | Dmhis | N-(2-aminoethyl)glycine | Naeg |
| D-α-methylisoleucine | Dmile | N-(3-aminopropyl)glycine | Norn |
| D-α-methylleucine | Dmleu | N-amino-α-methylbutyrate | Nmaabu |
| D-α-methyllysine | Dmlys | α-napthylalanine | Anap |
| D-α-methylmethionine | Dmmet | N-benzylglycine | Nphe |
| D-α-methylornithine | Dmorn | N-(2-carbamylethyl)glycine | Ngln |
| D-α-methylphenylalanine | Dmphe | N-(carbamylmethyl)glycine | Nasn |
| D-α-methylproline | Dmpro | N-(2-carboxyethyl)glycine | Nglu |
| D-α-methylserine | Dmser | N-(carboxymethyl)glycine | Nasp |
| D-α-methylthreonine | Dmthr | N-cyclobutylglycine | Ncbut |
| D-α-methyltryptophan | Dmtrp | N-cycloheptylglycine | Nchep |
| D-α-methyltyrosine | Dmty | N-cyclohexylglycine | Nchex |
| D-α-methylvaline | Dmval | N-cyclodecylglycine | Ncdec |
| D-N-methylalanine | Dnmala | N-cylcododecylglycine | Ncdod |
| D-N-methylarginine | Dnmarg | N-cyclooctylglycine | Ncoct |
| D-N-methylasparagine | Dnmasn | N-cyclopropylglycine | Ncpro |
| D-N-methylaspartate | Dnmasp | N-cycloundecylglycine | Ncund |
| D-N-methylcysteine | Dnmcys | N-(2,2-diphenylethyl)glycine | Nbhm |
| D-N-methylglutamine | Dnmgln | N-(3,3-diphenylpropyl)glycine | Nbhe |
| D-N-methylglutamate | Dnmglu | N-(3-guanidinopropyl)glycine | Narg |
| D-N-methylhistidine | Dnmhis | N-(1-hydroxyethyl)glycine | Nthr |
| D-N-methylisoleucine | Dnmile | N-(hydroxyethyl))glycine | Nser |
| D-N-methylleucine | Dnmleu | N-(imidazolylethyl))glycine | Nhis |
| D-N-methyllysine | Dnmlys | N-(3-indolylyethyl)glycine | Nhtrp |
| N-methylcyclohexylalanine | Nmchexa | D-N-methylmethionine | Dnmmet |
| D-N-methylornithine | Dnmorn | N-methylcyclopentylalanine | Nmcpen |
| N-methylglycine | Nala | D-N-methylphenylalanine | Dnmphe |
| N-methylaminoisobutyrate | Nmaib | D-N-methylproline | Dnmpro |
| N-(1-methylpropyl)glycine | Nile | D-N-methylserine | Dnmser |
| N-(2-methylpropyl)glycine | Nleu | D-N-methylthreonine | Dnmthr |
| D-N-methyltryptophan | Dnmtrp | N-(1-methylethyl)glycine | Nval |
| D-N-methyltyrosine | Dnmtyr | N-methyl-napthylalanine | Nmanap |
| D-N-methylvaline | Dnmval | N-methylpenicillamine | Nmpen |
| L-t-butylglycine | Tbug | N-(p-hydroxyphenyl)glycine | Nhtyr |
| L-ethylglycine | Etg | N-(thiomethyl)glycine | Ncys |

TABLE 3-continued

| Non-conventional amino acid | Code | Non-conventional amino acid | Code |
|---|---|---|---|
| L-homophenylalanine | Hphe | penicillamine | Pen |
| L-α-methylarginine | Marg | L-α-methylalanine | Mala |
| L-α-methylaspartate | Masp | L-α-methylasparagine | Masn |
| L-α-methylcysteine | Mcys | L-α-methyl-t-butylglycine | Mtbug |
| L-α-methylglutamine | Mgln | L-methylethylglycine | Metg |
| L-α-methylhistidine | Mhis | L-α-methylglutamate | Mglu |
| L-α-methylisoleucine | Mile | L-α-methylhomophenylalanine | Mhphe |
| L-α-methylleucine | Mleu | N-(2-methylthioethyl)glycine | Nmet |
| L-α-methylmethionine | Mmet | L-α-methyllysine | Mlys |
| L-α-methylnorvaline | Mnva | L-α-methylnorleucine | Mnle |
| L-α-methylphenylalanine | Mphe | L-α-methylornithine | Morn |
| L-α-methylserine | Mser | L-α-methylproline | Mpro |
| L-α-methyltryptophan | Mtrp | L-α-methylthreonine | Mthr |
| L-α-methylvaline | Mval | L-α-methyltyrosine | Mtyr |
| N-(N-(2,2-diphenylethyl)carbamylmethyl)glycine | Nnbhm | L-N-methylhomophenylalanine | Nmhphe |
| 1-carboxy-1-(2,2-diphenylethylamino)cyclopropane | Nmbc | N-(N-(3,3-diphenylpropyl)carbamylmethyl)glycine | Nnbhe |

As used herein, "amino acid side chain" or "side chain" refers to the characterizing substituent of the amino acid. This term refers to the substituent bound to the α-carbon of either a natural or non-natural α-amino acid. For example, the characterizing substituents of some naturally occurring amino acids are shown in Table 4.

TABLE 4

The Proteinogenic Amino Acids

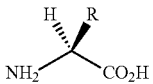

| Amino acid | —R |
|---|---|
| Alanine | —CH₃ |
| Arginine | —(CH₂)₃NHC(=NH)NH₂ |
| Asparagine | —CH₂CONH₂ |
| Aspartic acid | —CH₂CO₂H |
| Cysteine | —CH₂SH |
| Glutamine | —(CH₂)₂CONH₂ |
| Glutamic acid | —(CH₂)₂CO₂H |
| Glycine | —H |
| Histidine | —CH₂(4-imidazolyl) |
| Isoleucine | —CH(CH₃)CH₂CH₃ |
| Leucine | —CH₂CH(CH₃)₂ |
| Lysine | —(CH₂)₄NH₂ |
| Methionine | —(CH₂)₂SCH₃ |
| Phenylalanine | —CH₂Ph |
| Serine | —CH₂OH |
| Threonine | —CH(CH₃)OH |
| Tryptophan | —CH₂(3-indolyl) |
| Tyrosine | —CH₂(4-hydroxyphenyl) |
| Valine | —CH(CH₃)₂ |

Another naturally occurring amino acid is proline.

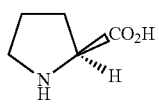

in which the α-side chain terminates in a bond with the amino acid amine nitrogen atom. Some non-limiting examples of characterizing substituents of non-naturally occurring amino acids are shown in Table 5:

TABLE 5

Non-Natural Amino Acids

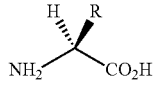

| Amino acid | —R |
|---|---|
| α-aminobutyric acid | —CH₂CH₃ |
| ornithine | —(CH₂)₃NH₂ |
| cyclohexylalanine | —CH₂C₆H₁₀ |
| cyclopentylalanine | —CH₂C₅H₈ |
| norvaline | —CH₂CH₂CH₃ |
| norleucine | —(CH₂)₃CH₃ |

In some embodiments, the cyclic peptide is a macrocycle formed by consecutively linking at least 18 to 22 atoms, wherein the first and last atoms are bonded to one another to form a ring. In a preferred embodiment the macrocycle is formed from 19 to 21 atoms, especially preferred are macrocycles formed from 20 atoms. In some embodiments, the first terminal residue and second terminal residue of the pentapeptide are alpha amino acids. In these embodiments, the resulting macrocycle ring size is preferably 18-22 atoms, more preferably 20 atoms. In particular, where one of the first terminal residue and second terminal residue of the pentapeptide is Lys and the other is Asp, the resulting macrocycle ring size is preferably 18-22 atoms, more preferably 20 atoms. It will be apparent to persons skilled in the art that modifications to the substituents at the first and second terminal residues of the pentapeptide will result in a slightly different optimal macrocycle requirements.

The two amino acid side chains of the first and second terminal residues defined above may be linked in any suitable manner to form a cyclic pentapeptide. In some embodiments, the side chains are linked by a covalent bond either directly or through a linker. In an illustrative example, the side chains are covalently linked to one another without an intervening linker, for example, by formation of a lactam bridge between a side chain carboxylic acid group and a side chain amino group or a disulfide bond between two side chain thiol groups. In a preferred embodiment, a carboxylic acid in the side chain of one amino acid residue is reacted with an amine in the side chain of a second amino acid residue to form an amide bond or lactam bridge.

In some embodiments, one of the amino acid residues having a side chain participating in the linkage is selected from L-aspartic acid, L-glutamic acid, D-aspartic acid, D-glutamic acid, L-α-methyl-aspartic acid, L-α-methyl-glutamic acid, D-α-methylaspartic acid and D-α-methylglutamic acid, and the other amino acid residue having a side chain participating in the linkage is selected from L-lysine, L-ornithine, D-lysine, D-ornithine, L-α-methyllysine, D-α-methyllysine, L-α-methylornithine and D-α-methylornithine. Preferably the amide bond is formed by reaction of an L-aspartic acid or L-glutamic acid with an L-lysine or L-ornithine.

In a preferred embodiment of the invention the amino acid residues in the sequence are D- or L-α-amino acids, especially L-α-amino acids.

In another aspect of the invention there is provided a compound having the following formula (I):

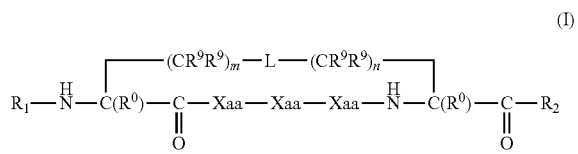

(I)

wherein each Xaa is independently selected from any amino acid residue;

$R_1$ is selected from H, an N-terminal capping group, a non-peptidic group or a group that mimics an amino acid side chain;

$R_2$ is selected from H, a C-terminal capping group, a group that mimics an amino acid side chain or a group that activates the terminal carboxylic acid carbonyl group to nucleophilic substitution;

each R9 and R0 are independently selected from H, $C_1$-$C_{10}$ alkyl, $C_2$-$C_{10}$ alkenyl, $C_2$-$C_{10}$ alkynyl, $C_3$-$C_{10}$cylcoalkyl, $C_5$-$C_{10}$cycloalkenyl, —OH, —O$C_1$-$C_{10}$ alkyl, —NH$_2$, —NH($C_1$-$C_{10}$alkyl), —N($C_1$-$C_{10}$alkyl)$_2$, $C_6$-$C_{12}$aryl, $C_3$-$C_{10}$heterocyclyl, $C_5$-$C_{10}$heteroaryl and halo;

L is selected from —NH—C(O)—, —C(O)—NH—, —S—S—, —CH(OH)CH$_2$—, —CH$_2$CH(OH)—, —CH═CH—, —CH$_2$—CH$_2$—, —NH—CH$_2$—CH$_2$—NH—, —CH$_2$—S—, —S—CH$_2$—, —C(O)—CH$_2$—, —CH$_2$—C(O)—, —S(O)$_t$—NH—, —NH—S(O)$_t$—, CH$_2$—P(═O)(OH)— and —P(═O)(OH)—CH$_2$—;

m is an integer from 1 to 4, n is an integer from 1 to 4, and t is 0, 1 or 2, wherein m+n=4, 5 or 6 and wherein when m is 2, n is not 3 and when m is 3, n is not 2.

As used herein, the term "alkyl" refers to a saturated, straight or branched chain hydrocarbon group, preferably having 1 to 10 carbon atoms. Examples of suitable alkyl groups include, but are not limited to, methyl, ethyl, n-propyl, isopropyl, butyl, sec-butyl, tert-butyl, pentyl, 2-methylbutyl, 3-methylbutyl, 4-methylbutyl, hexyl, 2-ethylbutyl, heptyl, octyl, nonyl and decyl. Preferred alkyl groups have 1 to 6 carbon atoms. Especially preferred alkyl groups have 1 to 3 carbon atoms.

As used herein, the term "alkenyl" refers to a straight or branched chain hydrocarbons containing at least one carbon-carbon double bond. Suitable alkenyl groups having 2 to 10 carbon atoms and include, but are not limited to, vinyl, allyl, 1-methylvinyl, butenyl, pentenyl, hexenyl, heptenyl, octenyl, nonenyl and decenyl. Preferred alkenyl groups have 2 to 6 carbon atoms. Especially preferred alkenyl groups have 2 or 3 carbon atoms.

As used herein, the term "alkynyl" refers to straight chain hydrocarbons containing at least one carbon-carbon triple bond. Suitable alkynyl groups having 2 to 10 carbon atoms include, but not limited to, ethynyl, 1-propynyl, 2-propynyl, butynyl, pentynyl, hexynyl, heptynyl, octynyl, nonynyl and decynyl. Preferred alkynyl groups have 2 to 6 carbon atoms. Especially preferred alkynyl groups have 2 or 3 carbon atoms.

As used herein, "halo" is intended to include fluoro, chloro, bromo and iodo.

As used herein, the term "cycloalkyl" refers to saturated mono- or poly-cyclic hydrocarbon groups. Suitable cycloalkyl groups having 3 to 10 carbon atoms include, but are not limited to, cyclopropyl, cyclobutyl, cyclopentyl, cyclohexyl, cycloheptyl, cyclooctyl, cyclononyl, cyclodecyl and the like. Preferred cycloalkyl groups include cyclopentyl and cyclohexyl.

As used herein, the term "cycloalkenyl" refers to saturated mono- or poly-cyclic hydrocarbon groups containing at least one carbon-carbon double bond. Suitable cycloalkenyl groups having 5 to 10 carbon atoms include, but are not limited to, cyclopentenyl, 1-methyl-cyclopentenyl, cyclohexenyl, cyclooctenyl, 1,3-cyclopentadienyl, 1,3-hexadienyl, 1,3-cyclohexadienyl, 1,4-cyclohexadienyl, 1,3-cycloheptadienyl, 1,3,5-cycloheptatrienyl and 1,3,5,7-cyclooctatetraenyl. Preferred cycloalkenyl groups include cyclopentenyl and cyclohexenyl.

The term "aryl" used either alone or in compound words denotes single, polynuclear, conjugated or fused residues of aromatic hydrocarbons. Examples of aryl include, but are not limited to, phenyl, biphenyl, naphthyl, tetrahydronaphthyl. Preferred aryl groups include phenyl and naphthyl.

The term "heteroaryl" refers to aromatic heterocyclic ring systems, wherein one or more carbon atoms (and where appropriate, hydrogen atoms attached thereto) of a cyclic hydrocarbon residue are replaced with a heteroatom to provide an aromatic residue. Where two or more carbon atoms are replaced, this may be by two or more of the same heteroatom or by different heteroatoms. Suitable heteroatoms include O, N, S and Se. Examples of heteroaryl include, but are not limited to, pyridyl, thienyl, furyl, pyrrolyl, indolyl, pyridazinyl, pyrazolyl, pyrazinyl, thiazolyl, pyrimidinyl, quinolinyl, isoquinolinyl, benzofuranyl, benzothienyl, purinyl, quinazolinyl, phenazinyl, acridinyl, benzoxazolyl, benzothiazolyl and the like. Preferred heteroaryl groups include pyridyl, thienyl, furyl, pyrrolyl.

The term "heterocyclyl" when used alone or in compound words includes monocyclic, polycyclic, fused or conjugated hydrocarbon residues, preferably $C_{3-10}$, preferably $C_{3-6}$, wherein one or more carbon atoms (and where appropriate, hydrogen atoms attached thereto) are replaced by a heteroatom so as to provide a non-aromatic residue. Suitable heteroatoms include, O, N, S, and Se. Where two or more carbon atoms are replaced, this may be by two or more of the same heteroatom or by different heteroatoms. Suitable examples of heterocyclic groups may include pyrrolidinyl, pyrrolinyl, piperidyl, piperazinyl, morpholino, indolinyl, imidazolidinyl, pyrazolidinyl, thiomorpholino, dioxanyl, tetrahydrofuranyl, tetrahydropyranyl, tetrahydropyrrolyl etc.

In preferred embodiments, any one of the following may apply:

$R_1$ is selected from H, an N-terminal capping group that stabilizes the terminus of a helix, usually having hydrogen atoms able to form hydrogen bonds or having a negative charge at the N-terminus to match with the helix dipole, a non-peptidic group or a mimic of an amino acid side chain. Suitable N-terminal capping groups include acyl and N-succinate. Suitable groups that mimic an amino acid side chain are any natural or unnatural amino acid side chain that is attached to the N-terminal amino group of the peptide through a carbonyl group derived from a carboxylic acid by formation of an amide bond. Suitable mimics of amino acid side chains include, but are not limited to:

$CH_3CH_2C(O)(CH_2)_uC(O)$—, $NH_2$ $(NH$=$)CNHC(O)(CH_2)_uC(O)$—, $H_2NC(O)(CH_2)_2C(O)(CH_2)_uC(O)$—, $HOC(O)(CH_2)_2C(O)(CH_2)_uC(O)$—, $HS(CH_2)_2C(O)(CH_2)_uC(O)$—, $H_2NC(O)(CH_2)_3C(O)(CH_2)_uC(O)$—, $HOC(O)(CH_2)_2C(O)(CH_2)_uC(O)$—, $(4$-imidazolyl$)(CH_2)C(O)(CH_2)_uC(O)$—, $CH_3CH_2CH(CH_3)CH_2C(O)(CH_2)_uC(O)$—, $(CH_3)_2CH(CH_2)_2C(O)(CH_2)_uC(O)$—, $H_2N(CH_2)_5C(O)(CH_2)_uC(O)$—, $CH_3S(CH_2)_3C(O)(CH_2)_uC(O)$—, $Ph(CH_2)_2C(O)(CH_2)_uC(O)$—, $Ph(CH_2)_4C(O)(CH_2)_uC(O)$—, $HO(CH_2)_2C(O)(CH_2)_uC(O)$—, $HOCH(CH_3)CH_2C(O)(CH_2)_uC(O)$—, $(3$-indolyl$)(CH_2)_2(CH_2)_uC(O)$—, $(4$-hydroxyphenyl$)(CH_2)_2C(O)(CH_2)_uC(O)$—, $(4$-hydroxyphenyl$)(CH_2)_3C(O)(CH_2)_uC(O)$—, $(CH_3)_2CHCH_2C(O)(CH_2)_uC(O)$—, $CH_3CH_2CH_2C(O)(CH_2)_uC(O)$—, $C_6H_{10}CH_2C(O)(CH_2)_uC(O)$—, $CsH_8$ $CH_2C(O)(CH_2)_uC(O)$—, $CH_3C(O)(CH_2)_uC(O)$—, $CH_3$ $(CH_2)_4C(O)(CH_2)_uC(O)$—, $CH_3(CH_2)_5C(O)(CH_2)_uC(O)$—, $HOC(O)CH_2C(O)(CH_2)_uC(O)$—, $HS(CH_2)C(O)(CH_2)_uC(O)$—, $H_2N(CH_2)_4C(O)(CH_2)_uC(O)$— and $HOCH_2C(O)(CH_2)_uC(O)$— wherein u is 0 or an integer from 1 to 10. The preferred non-peptidic groups enhance the stability, bioavailability or activity of the peptides. Suitable non-peptidic groups include, but are not limited to hydrophobic groups such as carbobenzoxyl, dansyl, t-butyloxycarbonyl, acetyl, 9-fluorenylmethoxycarbonyl, groups which stabilize or mimic alpha-helices, groups which mimic the secondary structure of peptides, particularly alpha helical peptides, such as those disclosed in WO 03/018587, groups which improve bioavailability, such as hydrophilic groups which aid aqueous solubility, for example, cyclodextrans; groups which are recognized by transport receptors to allow or improve transport of the peptides to the site of activity, for example, transport across cell walls or through an epithelial layer such as skin or the gut wall.

$R_2$ is selected from H, a C-terminal capping group that stabilizes the terminus of a helix, usually having hydrogen atoms able to form hydrogen bonds or having a positive charge at the C-terminus to match with the helix dipole, a peptide of 1, 2, 3, 4 or 5 amino acid residues optionally capped with a C-terminal capping group that stabilizes the terminus of a helix, usually having hydrogen atoms able to form hydrogen bonds or having a positive charge at the C-terminus to match with the helix dipole, a mimic of an amino acid side chain or a group which activates the terminal carboxylic acid carbonyl group to nucleophilic substitution. A suitable C-terminal capping group is $NH_2$. Suitable mimics of amino acid side chains are any common or unnatural amino acid side chain that is attached to the C-terminal carbonyl group of the peptide through an amine group by formation of an amide bond. Suitable mimics of amino acid side chains include but are not limited to:

—$NH(CH_2)_uNHCH_2CH_3$, —$NH(CH_2)_uNH(CH_2)_4NHC$(=$NH)NH_2$, —$NH(CH_2)_uNH(CH_2)_2C(O)NH_2$, —$NH(CH_2)_uNH(CH_2)_2CO_2H$, —$NH(CH_2)_uNH(CH_2)_2SH$, —$NH(CH_2)_uNH(CH_2)_3C(O)NH_2$, —$NH(CH_2)_uNH(CH_2)_3CO_2H$, —$NH(CH_2)_uNH(CH_2)_2(4$-imidazolyl$)$, —$NH(CH_2)_uNHCH_2CH(CH_3)CH_2CH_3$, —$NH(CH_2)_uNH$—$(CH_2)_2CH(CH_3)_2$, —$NH(CH_2)_uNH(CH_2)_5NH_2$, —$NH(CH_2)NH(CH_3)_3SCH_3$, —$NH(CH_2)_uNH(CH_2)_2(3$-indolyl$)$, —$NH(CH_2)_uNH(CH_2)_2(4$-hydroxyphenyl$)$, —$NH(CH_2)_uNH(CH_2)_3(4$-hydroxyphenyl$)$, —$NH(CH_2)_uNH$—$CH_2CH(CH_3)_2$, —$(NHCH_2)_uNHCH_2CH_2CH_3$, —$NH(CH_2)_uNH$—$CH_2C_6H_8$, —$NH(CH_2)_uNHCH_2C_5H_8$, —$NH(CH_2)_uNHCH_3$, —$NH(CH_2)_uNH(CH_2)_4CH_3$, —$NH(CH_2)_uNH(CH_2)_5CH_3$, —$NH(CH_2)_uNHCH_2CO_2H$, —$NH(CH_2)_uNHCH_2SH$, —$NH(CH_2)_uNH(CH_2)_2OH$, —$NH(CH_2)_uNH(CH_2)_5NH_2$ and —$NH(CH_2)_uNHCH_2OH$; wherein u is 0 or an integer from 1 to 10.

Suitable groups which activate the C-terminal carboxylic to nucleophilic attack include converting the carboxylic acid to an acid chloride, an acid anhydride, an acyl azide, an O-acylisourea, a phosphonium derivative or an activated ester, especially those known in the art for activating carboxylic acids for peptide bond formation.

In some embodiments, non-peptidic groups enhance the stability and circulating time, or decrease immunogenicity, or increase solubility, bioavailability or activity of the peptides (see U.S. Pat. No. 4,179,337). Suitable non-peptidic groups include but are not limited to hydrophobic groups such as t-butyl, groups which stabilize or mimic alpha-helices, groups which mimic the secondary structure of peptides, particularly alpha helical peptides, such as those disclosed in WO 03/018587, groups which improve bioavailability, such as hydrophilic groups which aid aqueous solubility, for example, cyclodextrans; groups which are recognized by transport receptors to allow or improve transport of the peptides to the site of activity, for example, transport across cell walls or through an epithelial layer such as skin or the gut wall. In some embodiments, PEG (polyethylene glycol) groups are conjugated to the peptide compounds to make those compounds more easily formulated and orally available. The amphiphilic nature of PEG helps protect the parent peptide from enzymatic breakdown and positions the drug for absorption across the gastrointestinal tract into the plasma. The terms "pegylated" and "pegylation" refer to the process of reacting a poly(alkylene glycol), suitably an activated poly(alkylene glycol), with a facilitator such as an amino acid, e.g. lysine, to form a covalent bond. Although "pegylation" is often carried out using poly(ethylene glycol) or derivatives thereof, such as methoxy poly(ethylene glycol), the term is not intended to be so limited here, but is intended to include any other useful poly(alkylene glycol), such as, for example poly(propylene glycol). The chemical moieties for derivitization may also be selected from water soluble polymers such as polyethylene glycol, ethylene glycol/propylene glycol copolymers, carboxymethylcellulose, dextran, polyvinyl alcohol and the like. The pentapeptide compounds may be modified at random positions within the molecule, or at predetermined positions within the molecule and may include one, two, three or more attached chemical moieties. In some embodiments, the modification occurs at a position outside of the cyclic pentapeptide moiety, for example at amino acids preceding the cyclic pentapeptide moiety or at the N-terminus.

The polymer may be of any molecular weight, and may be branched or unbranched. For polyethylene glycol, exemplary examples include micropegylated groups devised specifically to enhance oral delivery in peptides as described in WO2004047871. Methods for attaching Peg groups are well described in the patent literature (WO2004047871, U.S. Pat. No. 5,643,575; EP 0 401 384; WO03057235A2) For example, polyethylene glycol may be covalently bound through amino acid residues via a reactive group, such as, a free amino or carboxyl group. Reactive groups are those to which an activated polyethylene glycol molecule may be bound. One or more reaction chemistries may be employed to attach polyethylene glycol to specific amino acid residues (e.g., lysine, histidine, aspartic acid, glutamic acid, or cysteine) of the polypeptide or to more than one type of amino acid residue (e.g., lysine, histidine, aspartic acid, glutamic acid, cysteine and combinations thereof) of the protein or polypeptide. Polyethylene glycol may be attached to the protein or polypeptide either directly or by an intervening linker. Polyethylene glycol can also be attached to polypeptides using a number of different intervening linkers. For example, U.S. Pat. No. 5,612,460 discloses urethane linkers for connecting polyethylene glycol to proteins. Protein polyethylene glycol conjugates wherein the polyethylene glycol is attached to the protein or polypeptide by a linker can also be produced by reaction of proteins or polypeptides with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number of additional polyethylene glycol derivatives and reaction chemistries for attaching polyethylene glycol to proteins and polypeptides are described in WO 03/057235; PCT/GB03/00062; U.S. Pat. No. 5,428,128; U.S. Pat. No. 6,127,355; and U.S. Pat. No. 5,880,131.

Each R9 is selected from H, $CH_3$, $CH_2CH_3$, vinyl, OH, $OCH_3$, $NH_2$, $NH(CH_3)$, $N(CH_3)_2$, phenyl, F or Cl; most preferably H or $CH_3$, especially H.

Each R0 is selected from H, $CH_3$, $CH_2CH_3$ or vinyl, especially H.

m is 1 and n is 3 or 4, m is 2 and n is 4, m is 3 and n is 1 or m is 4 and n is 1 or 2, especially where m is 1 and n is 4.

Each Xaa may be any amino acid residue selected to mimic the amino acid residues in a known alpha helical peptide of interest or to prepare an unknown peptide having new properties. An individual Xaa can be the same or different as another Xaa and is preferably selected from a D- or L-alpha amino acid residue. Especially preferred peptides of formula (I) have at least one Xaa which is a D- or L-alpha amino acid residue that is favorable to helix formation. Even more preferred are peptides in which 2 or 3 of Xaa are D- or L-alpha amino acid residues that are favorable to helix formation, for example, alanine, arginine, lysine, methionine, leucine, glutamic acid, glutamine, cysteine, isoleucine, phenylalanine, tyrosine, tryptophan, histidine and aspartic acid, especially alanine, arginine, lysine, methionine, leucine, glutamic acid and glutamine.

L is preferably —NH—C(O)— or —C(O)—NH—.

Surprisingly, the cyclic pentapeptides of the invention display tolerance of variation of Xaa residues, with most amino acid substitutions of these residues retaining a high degree of helicity. The range of amino acid substitutions that could be made at a specific Xaa residue would be readily apparent to a person of skill in the art.

Representative peptides of the invention include, but are not limited to:

```
Ac-cyclo-1,5-[KXaaXaaXaaD]-NH2      [SEQ ID NO. 1]
Ac-cyclo-1,5-[DXaaXaaXaaK]-NH2      [SEQ ID NO. 2]
Ac-cyclo-1,5-[KXaaXaaXaaE]-NH2      [SEQ ID NO. 3]
Ac-cyclo-1,5-[EXaaXaaXaaK]-NH2      [SEQ ID NO. 4]
Ac-cyclo-1,5-[OXaaXaaXaaD]-NH2      [SEQ ID NO. 5]
Ac-cyclo-1,5-[DXaaXaaXaaO]-NH2      [SEQ ID NO. 6]
Ac-Xaa-cyclo-2,6-[KXaaXaaXaaD]-NH2  [SEQ ID NO. 7]
```

Especially preferred peptides are those of SEQ ID NO. 1, SEQ ID NO. 2, SEQ ID NO. 4, SEQ ID NO. 6 and SEQ ID NO. 7, more especially SEQ ID NO. 1 and SEQ ID NO. 7.

Illustrative examples of amino acid sequences represented by the above peptides include:

```
Ac-(cyclo-1,5)-[KARAD]-NH2      [SEQ ID NO. 8]
Ac-(cyclo-1,5)-[DARAK]-NH2      [SEQ ID NO. 9]
Ac-(cyclo-1,5)-[KARAE]-NH2      [SEQ ID NO. 10]
Ac-(cyclo-1,5)-[EARAK]-NH2      [SEQ ID NO. 11]
Ac-(cyclo-1,5)-[OARAD]-NH2      [SEQ ID NO. 12]
Ac-(cyclo-1,5)-[DARAO]-NH2      [SEQ ID NO. 13]
Ac-[KARAD]-NH2                  [SEQ ID NO. 14]
Ac-cyclo-2,6-R[KLLLD]-NH2       [SEQ ID NO. 15]
Ac-cyclo-2,6-R[KLALD]-NH2       [SEQ ID NO. 16]
Ac-cyclo-2,6-R[KLFAD]-NH2       [SEQ ID NO. 17]
Ac-(cyclo-1,5)-[OARAE]-NH2      [SEQ ID NO. 18]
Ac-(cyclo-1,5)-[EARAO]-NH2      [SEQ ID NO. 19]
Ac-(cyclo-1,5)-[KARAD]-OH       [SEQ ID NO. 20]
H-(cyclo-1,5)-[KARAD]-NH2       [SEQ ID NO. 21]
H-(cyclo-1,5)-[KARAD]-OH        [SEQ ID NO. 22]
Ac-(cyclo-2,6)-R[KAAAD]-NH2     [SEQ ID NO. 23]
Ac-(cyclo-2,6)-R[KALAD]-NH2     [SEQ ID NO. 24]
Ac-(cyclo-2,6)-R[KAMAD]-NH2     [SEQ ID NO. 25]
Ac-(cyclo-2,6)-R[KAQAD]-NH2     [SEQ ID NO. 26]
Ac-(cyclo-2,6)-R[KAFAD]-NH2     [SEQ ID NO. 27]
Ac-(cyclo-2,6)-R[KAGAD]-NH2     [SEQ ID NO. 28]
Ac-(cyclo-2,6)-R[KGSAD]-NH2     [SEQ ID NO. 29]
Ac-(cyclo-2,6)-R[KSSSD]-NH2     [SEQ ID NO. 30]
Ac-(cyclo-2,6)-R[KGGGD]-NH2     [SEQ ID NO. 31]
```

In some embodiments, the peptide compound comprises at least one cyclic pentapeptide of the invention and at least 1, 2, 3, 4, 5, 6, 7, 8, 9, 10, 11, 12, 13, 14, 15 or more amino acid residues adjacent thereto. In specific embodiments, the peptide compound comprises a single cyclic pentapeptide of the invention and another amino acid residue located immediately upstream or downstream thereof.

In another aspect, the present invention provides a method for constructing a constrained helical peptide comprising the steps of: (1) synthesizing a peptide, wherein the peptide comprises a sequence of five amino acid residues having a first terminal residue and a second terminal residue that are separated by an intervening sequence of three amino acid residues, and wherein the individual side chains of the first and second terminal residues are linkable to each other; and (2) cyclizing the peptide by linking the side chain of the first terminal residue with the side chain of the second terminal residue, thereby yielding a constrained helical peptide. In certain embodiments, the first terminal residue has a side chain containing an amide bond-forming substituent and the second terminal residue has a side chain containing a functional group capable of forming an amide linkage with the side chain amide bond-forming substituent of the first terminal residue and the peptide is cyclised by reacting the side chain amide bond-forming substituent of the first terminal residue with the functional group of the second terminal residue to form an amide bond linkage, thereby yielding a constrained helical peptide. During peptide synthesis, reactive groups on the side chains, including the amide forming substituents are suitably protected, for example, carboxy groups can be suitably protected as esters such as methyl, ethyl, allyl, benzyl, t-butyl or phenyl esters and amino groups can be suitably protected with alkyloxy carbonyl, allyloxycarbonyl (Alloc), benzyloxycarbonyl (Z), t-butoxycarbonyl (Boc), 2-(4-biphenylyl)-isopropoxycarbonyl (Bpoc), 9-fluorenylmethoxycarbonyl (Fmoc), triphenylmethyl (trityl) or 2-nitrophenylsulphenyl (Nps) groups, which may be removed after synthesis of the peptide and before reaction to form the amide bond linkage. Suitable methods for selectively protecting and deprotecting functional groups can be found in Green & Wutz[94] and Taylor (2002)[43]

The peptides of the present invention may be prepared using techniques known in the art. For example, peptides can be synthesized using various solid phase techniques[91] or using an automated synthesis and standard Fmoc chemistry[92]. These techniques are also suitable for incorporating non-naturally occurring amino acid residues into the amino acid sequence.

Alternatively, non-naturally occurring amino acids may be incorporated into the sequence by manipulation of a residue in the sequence. For example, the hydroxy group or thiol group of threonine, serine or cysteine may be alkylated to provide an ether or thioether, or substituents may be introduced into the phenyl ring of phenylalanine or tyrosine using known substitution reactions such as Friedel-Crafts alkylation or acylation.

Once the peptides of the present invention have been prepared, they may be substantially purified using preparative HPLC. The composition of the peptides can be confirmed by amino acid analysis or by sequencing, for example, using the Edman Degradation procedure.

Suitable protecting groups for use during solid phase synthesis or solution phase of the amino acid sequences, together with suitable protecting and deprotecting methods for reactive functional groups such as amines and carboxylic acids, are known in the art, for example, as found in Green & Wutz[94].

Once the peptide is prepared and deprotection of the side chains is effected, cyclization to form a cyclic peptide may be achieved by methods known in the art. For example, an amide bond may be formed between a side chain carboxylic acid and a side chain amine by activation of the carboxylic acid, for example, as an acid chloride, acid anhydride, an acyl azide, a carbodiimide, an acyloxyphosphonium or uronium compound or an active ester, and allowing nucleophilic attack from the amine nitrogen atom. A particularly preferred method of activating the carboxylic acid to nucleophilic attack is preparation of an acyloxyphosphonium or uronium derivative of the carboxylic acid, for example, by reaction with the carboxylic acid with benzotriazolyloxy-tri-(dimethylamino)phosphonium hexafluorophosphate (BOP) or benzotriazolyloxy-tris-(pyrrolidinyl)phosphonium hexafluorophosphate (Py-BOP) in the presence of a tertiary amine such as triethylamine or diisopropylethylamine (DIPEA) or similar reaction using Benzotriazol-1-yl-1,1,3,3-tetramethyluronium ion (HBTU).

A representative solid phase synthesis is shown in Scheme 1:

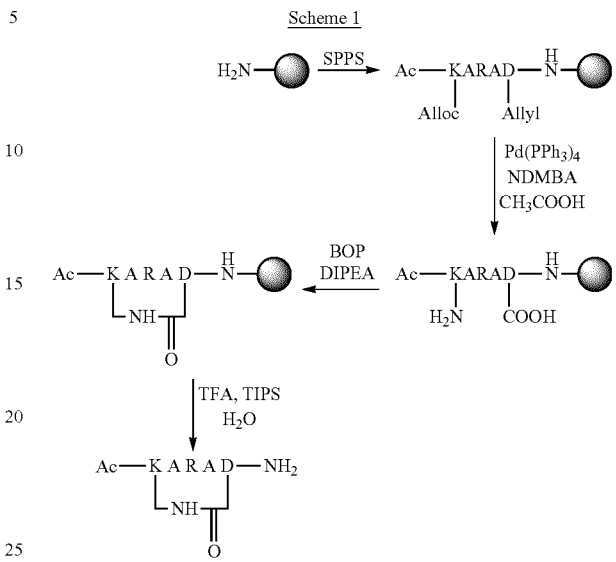

The peptides of the invention are designed to mimic binding determinants from alpha helical binding domains of known proteins. Such peptides have a number of uses, including the determination of whether a binding determinant in an alpha helical binding domain of a known protein can serve as a structural model for the design of peptidomimetics or small molecules capable of mimicking or antagonizing the binding activity of the intact protein. In using the peptides of the invention for this purpose, the practitioner may select a binding protein with an alpha helical domain that interacts with a ligand, and then identify a candidate binding determinant situated within a sequence of (e.g., three or more) contiguous amino acid residues in the helical binding domain. The candidate binding determinant can be identified by using mutagenesis (e.g., alanine scanning mutagenesis) to determine whether the candidate sequence contains one or more amino acid residues that are critical for ligand binding. Subsequently, a constrained peptide containing the candidate sequence is designed by selecting two residues in the candidate sequence (designated i and i+4) which are separated by an intervening sequence of n–1 (e.g., 3) amino acid residues and which do not substantially interact with ligand (as determined by mutagenesis in the previous step) for substitution with amino acid residues having side chains that can be linked to each other. The peptide is synthesized and the side chains of the foreign i and i+4 residues are used to tether the peptide in an alpha helical conformation according to the methods of the invention described herein. Finally, the peptide's binding activity with the ligand is assayed, e.g., in a binding competition assay with the intact binding protein, and the results of the assay can be used to determine whether a peptidomimetic or small molecule antagonist could be developed using the binding determinant as a structural model.

Thus, in a further aspect, the invention contemplates the use an alpha helical cyclic peptide, wherein the peptide comprises a sequence of five amino acid residues having a first terminal residue and a second terminal residue that are separated by an intervening sequence of three amino acid residues, and wherein the side chains of the first and second terminal residues are linked to each other as a scaffold for presenting the side chains of at least some of the five amino acid residues in a (three dimensional) conformation that is analogous to the conformation of amino acid side chains of at least a portion of an alpha helical domain of a known protein. In some embodiments, the side chains of at least 1 or 2 or all 3 of the intervening amino acid residues are so analogously presented. In other embodiments, the side chains of at least 1 or 2 or all 3 of the intervening amino acid residues and at least one terminal amino acid residue are so analogously presented. Suitably, at least part of the conformationally constrained secondary structure defined by the five amino acid residues (i.e., pentapeptide) mimics a member of a ligand-receptor binding pair. Illustrative examples of ligand-receptor binding pairs include protein-DNA binding partners (e.g., Zif268 and G/C rich major groove), protein-RNA binding partners (e.g., HIV reverse transcriptase and Rev response element (RRE); λ-N peptide and BoxB RNA; p22 peptides and BoxB RNA) and protein-protein binding partners (e.g., p53 and HDM2; Bak and Bcl-$X_L$; VHL peptide and Elongin C; VP16 activation domain and $HTAF_{II}31$; hPTH and hPTHrP; Dynorphin A and κ,δ-Opioid receptors; Apolipoprotein-E and LDL receptor; Neuropeptide-Y and NPY receptors; Galanin and Gal receptors; Corticotropin Releasing Factor and CRF receptors; Calcitonin Gene Related Peptide and CGRP receptors; Nociceptin and ORL1 receptor; Vasointestinal Peptide and $VPAC_{1 \& 2}$; and Nuclear Coactivators (eg. SRC1, GRIP1) and Nuclear Receptors.

While not wishing to be limited by any one particular theory or mode of operation, the constrained helical peptides of the present invention are believed to derive their activity by interaction of the face of the helix opposing the i→i+4 constraint. However, when two or more tandemly arrayed constrained helical peptides are present, as part of an extended helix polypeptide backbone or super helix, the positions i→i+4 of a first constrained helical pentapeptide will be offset by approximately one third of a turn relative to positions i→i+4 of a second constrained helical pentapeptide. In other words, the i→i+4 faces of the two helices will not be aligned directly in the same plane and will be out of register by approximately one third of a turn. Thus, in certain embodiments where an extended helix polypeptide backbone or super helix is required for interaction with a biomolecule of interest, it may be desirable to take this offset into account when designing a helical peptide so that one face of its helix is substantially free of any cyclizing linkages that may occlude or otherwise interfere with this interaction. In illustrative examples, the helical peptide may simply comprise two or three consecutive constrained helical pentapeptides. In other illustrative examples, the helical peptide may comprise two consecutive constrained helical pentapeptides spaced from a third constrained helical pentapeptide by about 1, 2, 5, 8 or 9 natural or unnatural helix-forming amino acid residues. In still other illustrative examples, the helical peptide may comprise three consecutive constrained helical pentapeptides spaced from a fourth constrained helical pentapeptide by about 0, 3, 4, 6 or 7 natural or unnatural helix-forming amino acid residues; or alternatively 1, 2, 5, 6 or 9 natural or unnatural helix-forming amino acid residues, depending on which face is required to be kept substantially free of any cyclizing linkages. In still other illustrative examples, the helical peptide may comprise four consecutive constrained helical pentapeptides spaced from a fifth constrained helical pentapeptide by about 1, 2 or 3 natural or unnatural helix-forming amino acid residues. In still other illustrative examples, the helical peptide may comprise five consecutive constrained helical pentapeptides spaced from a sixth constrained helical pentapeptide by about 2, 7, 12 or 17 natural or unnatural helix-forming amino acid residues. The optimal spacing between cyclic pentapeptide modules is determined on a case-by-case basis and would be readily apparent to a person skilled in the art through simple molecular modeling experiments using commercially available programs (e.g., InsightII)[104].

In certain embodiments which require mimicking multiple turns of an alpha helical binding domain, the conformationally constrained peptide comprises a plurality (e.g., 2, 3, 4, 5, 6, 7, 8, 9 or more) of pentapeptides as broadly described above. Accordingly, in yet another aspect, the present invention provides the use of a conformationally constrained peptide having a plurality of alpha helical pentapeptide sequences, wherein the pentapeptide sequences comprise a sequence of five amino acid residues having a first terminal residue and a second terminal residue that are separated by an intervening sequence of three amino acid residues, and wherein the side chains of the first and second terminal residues are linked to each other, as a scaffold for presenting the side chains of at least some of the amino acid residues of the pentapeptide sequences in a (three-dimensional) configuration that is analogous to the configuration of amino acid side chains of at least a portion of an alpha helical domain of a known protein.

As used herein, the term "scaffold" is used in its broadest sense and includes a region or domain that has a conserved tertiary structural motif that can be modified to display one or more specific amino acid residues in a fixed conformation.

In some embodiments, the side chains of at least 1 or 2 or all 3 of the intervening amino acid residues of each pentapeptide sequence are so analogously presented. In other embodiments, the side chains of at least 1 or 2 or all 3 of the intervening amino acid residues and at least one terminal amino acid residue of each pentapeptide sequence are so analogously presented. Suitably, at least part of the conformationally constrained secondary structure defined by the pentapeptide sequences mimics a member of a ligand-receptor binding pair. In illustrative examples, some or all of the pentapeptides are located adjacent to each other. Alternatively, at least one of the pentapeptides is spaced from a pair of adjacent pentapeptides.

In certain embodiments, the conformationally constrained peptides of the invention are designed to mimic epitopes in proteins and are used to selectively raise polyclonal or monoclonal antibodies against such individual epitopes. Since the peptides will frequently be too small to generate an immune response, the peptides can be conjugated to carriers known to be immunogenic in the species to be immunized, e.g., keyhole limpet hemocyanin, serum albumin, bovine thyroglobulin, or soybean trypsin inhibitor using a bifunctional or derivatising agent, for example, maleimidobenzoyl sulfosuccinimide ester (conjugation through cysteine residues), N-hydroxysuccinimide (through lysine residues), glutaraldehyde, succinic anhydride, SOCl, or $R^1N=C=NR$, where R and $R^1$ are different alkyl groups.

Advantageously, the macrocyclic moiety of the pentapeptide is stable in water to temperatures of up to about 80° C. and stable to denaturants such as 8M guanidine hydrochloride, and to the degradative effects of proteolytic enzymes such as trypsin or those present in human serum. The alpha helical short-chain peptides are therefore suitable for use as chemical or biological probes, pharmaceuticals, biotechnology products such as vaccines or diagnostic agents, new components of novel biopolymers and as industrial agents.

The alpha helical pentapeptides of the invention can be used alone to mimic a specific peptide motif of a protein or polypeptide or may be incorporated into a larger polymeric or non polymeric non-peptidic molecules or into hybrids of peptidic and non-peptidic components.

In another aspect of the present invention there is provided a use of at least one alpha helical cyclic peptide, wherein the peptide comprises a sequence of five amino acid residues having a first terminal residue and a second terminal residue that are separated by an intervening sequence of three amino acid residues, and wherein the side chains of the first and second terminal residues are linked to each other, as a macrocyclic module for incorporation into a non-peptidic molecular structure, or for constructing a multi-macrocyclic structure that mimics multiple turns of an alpha helix.

Multi-macrocyclic structures may provide new or unknown three dimensional positioning of side chains in an alpha helix or may mimic a portion of, or an entire, alpha helical motif from a known protein or polypeptide.

In a preferred embodiment, the alpha helical cyclic peptide, which is used as the scaffold or macrocyclic module, has the formula (II):

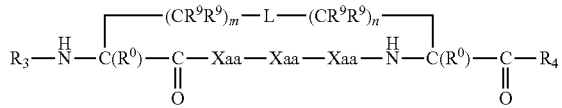

(II)

wherein each Xaa is independently selected from any amino acid;

each R9 and R0 are independently selected from H, $C_1$-$C_{10}$alkyl, $C_2$-$C_{10}$ alkenyl, $C_2$-$C_{10}$ alkynyl, $C_3$-$C_{10}$cylcoalkyl, $C_1$-$C_{10}$cycloalkenyl, —OH, —O$C_1$-$C_{10}$ alkyl, —NH$_2$, —NH($C_1$-$C_{10}$alkyl), —N($C_1$-$C_{10}$alkyl)$_2$, $C_6$-$C_{10}$aryl, $C_3$-$C_{10}$heterocyclyl, $C_5$-$C_{10}$heteroaryl and halo;

L is selected from —NH—C(O)—, —C(O)—NH—, —S—S—, —CH(OH)CH$_2$—, CH$_2$CH(OH)—, —CH=CH—, —CH$_2$—CH$_2$—, —NH—CH$_2$— —CH$_2$—NH—, —CH$_2$—S—, —S—CH$_2$—, —C(O)—CH$_2$—, —CH$_2$—C(O)—, —S(O)$_t$—NH—, —NH—S(O)$_t$—, CH$_2$—P(=O)(OH)— and —P(=O)(OH)—CH$_2$—;

$R_3$ is selected from H, an N-capping group or a mimic of an amino acid side chain, $R_4$ is selected from H, a C-terminal capping group, a mimic of an amino acid side chain or a group which activates the terminal carboxylic acid carbonyl group to nucleophilic substitution;

m is an integer from 1 to 4, n is an integer from 1 to 4, and t is 0, 1 or 2, wherein m+n=4, 5 or 6 and wherein when m is 2, n is not 3 and when m is 3, n is not 2.

In preferred embodiments, any one of the following may apply:

$R_1$ is selected from H, an N-terminal capping group that stabilizes the terminus of a helix, usually having hydrogen atoms able to form hydrogen bonds or having a negative charge at the N-terminus to match with the helix dipole, or a mimic of an amino acid side chain. Suitable N-terminal capping groups include acyl and N-succinate. Suitable groups that mimic an amino acid side chain are any natural or unnatural amino acid side chain that is attached to the N-terminal amino group of the peptide through a carbonyl group derived from a carboxylic acid by formation of an amide bond. Suitable mimics of amino acid side chains include, but are not limited to:

CH$_3$CH$_2$C(O)(CH$_2$)$_u$C(O)—, NH$_2$ (NH=)CNHC(O)(CH$_2$)$_u$C(O)—, H$_2$NC(O)(CH$_2$)$_2$C(O)(CH$_2$)C(O)—, HOC(O)(CH$_2$)$_2$C(O)(CH$_2$)$_u$C(O)—, HS(CH$_2$)$_2$C(O)(CH$_2$)$_u$C(O)—, H$_2$NC(O)(CH$_2$)$_3$C(O)(CH$_2$)$_u$C(O)—, HOC(O)(CH$_2$)$_2$C(O)(CH$_2$)$_u$C(O)—, (4-imidazolyl)(CH$_2$)C(O)(CH$_2$)$_u$C(O)—, CH$_3$CH$_2$CH(CH$_3$)CH$_2$C(O)(CH$_2$)$_u$C(O)—, (CH$_3$)$_2$CH(CH$_2$)$_2$C(O)(CH$_2$)$_u$C(O)—, H$_2$N(CH$_2$)$_5$C(O)(CH$_2$)$_u$C(O)—, CH$_3$S(CH$_2$)$_3$C(O)(CH$_2$)$_u$C(O)—, Ph(CH$_2$)$_2$C(O)(CH$_2$)$_u$C(O)—, Ph(CH$_2$)$_4$C(O)(CH$_2$)$_u$C(O)—, HO(CH$_2$)$_2$C(O)(CH$_2$)$_u$C(O)—, HOCH(CH$_3$)CH$_2$C(O)(CH$_2$)$_u$C(O)—, (3-indolyl)(CH$_2$)$_2$(CH$_2$)$_u$C(O)—, (4-hydroxyphenyl)(CH$_2$)$_2$C(O)(CH$_2$)$_u$C(O)—, (4-hydroxyphenyl)(CH$_2$)$_3$C(O)(CH$_2$)$_u$C(O)—, (CH$_3$)$_2$CHCH$_2$C(O)(CH$_2$)C(O)—, CH$_3$CH$_2$CH$_2$C(O)(CH$_2$)$_u$C(O)—, $C_6H_{10}$CH$_2$C(O)(CH$_2$)$_u$C(O)—, $C_5H_8$CH$_2$C(O)(CH$_2$)$_u$C(O)—, CH$_3$C(O)(CH$_2$)$_u$C(O)—, CH$_3$(CH$_2$)$_4$C(O)(CH$_2$)$_u$C(O)—, CH$_3$(CH$_2$)$_5$C(O)(CH$_2$)$_u$C(O)—, HOC(O)CH$_2$C(O)(CH$_2$)C(O)—, HS(CH$_2$)$_2$C(O)(CH$_2$)C(O)—, H$_2$N(CH$_2$)$_4$C(O)(CH$_2$)$_u$C(O)— and HOCH$_2$C(O)(CH$_2$)$_u$C(O)— wherein u is 0 or an integer from 1 to 10;

$R_2$ is selected from H, a C-terminal capping group that stabilizes the terminus of a helix, usually having hydrogen atoms able to form hydrogen bonds or having a positive charge at the C-terminus to match with the helix dipole, a mimic of an amino acid side chain or a group which activates the terminal carboxylic acid carbonyl group to nucleophilic substitution. A suitable C-terminal capping group is NH$_2$. Suitable mimics of amino acid side chains are any common or unnatural amino acid side chain that is attached to the C-terminal carbonyl group of the peptide through an amine group by formation of an amide bond. Suitable mimics of amino acid side chains include but are not limited to:

—NH(CH$_2$)$_u$NHCH$_2$CH$_3$, —NH(CH$_2$)$_u$NH(CH$_2$)$_4$NHC(=NH)NH$_2$, —NH(CH$_2$)$_u$NH(CH$_2$)$_2$C(O)NH$_2$, —NH(CH$_2$)$_u$NH(CH$_2$)$_2$CO$_2$H, —NH(CH$_2$)$_u$NH(CH$_2$)$_2$SH, —NH(CH$_2$)$_u$NH(CH$_2$)$_3$C(O)NH$_2$, —NH(CH$_2$)$_u$NH(CH$_2$)$_3$CO$_2$H, —NH(CH$_2$)$_u$NH(CH$_2$)$_2$(4-imidazolyl), —NH(CH$_2$)$_u$NHCH$_2$CH(CH$_3$)CH$_2$CH$_3$, —NH(CH$_2$)$_u$NH(CH$_2$)$_2$CH(CH$_3$)$_2$, —NH(CH$_2$)$_u$NH(CH$_2$)$_5$NH$_2$, —NH(CH$_2$)$_u$NH(CH$_3$)$_3$SCH$_3$, —NH(CH$_2$)$_u$NH(CH$_2$)$_2$(3-indolyl), —NH(CH$_2$)$_u$NH(CH$_2$)$_2$(4-hydroxyphenyl), —NH(CH$_2$)$_u$NH(CH$_2$)$_3$(4-hydroxyphenyl), —NH(CH$_2$)$_u$NHCH$_2$CH(CH$_3$)$_2$, —NH(CH$_2$)$_u$NHCH$_2$CH$_2$CH$_3$, —NH(CH$_2$)$_u$NHCH$_2$$C_6H_{10}$, —NH(CH$_2$)$_u$NHCH$_2$$C_5H_8$, —NH(CH$_2$)$_u$NHCH$_3$, —NH(CH$_2$)$_u$NH(CH$_2$)$_4$CH$_3$, —NH(CH$_2$)$_u$NH(CH$_2$)$_5$CH$_3$, —NH(CH$_2$)$_u$NHCH$_2$CO$_2$H, —NH(CH$_2$)$_u$NHCH$_2$SH, —NH(CH$_2$)$_u$NH(CH$_2$)$_2$OH, —NH(CH$_2$)$_u$NH(CH$_2$)$_5$NH$_2$ and —NH(CH$_2$)$_u$NHCH$_2$OH; wherein u is 0 or an integer from 1 to 10.

Suitable groups which activate the C-terminal carboxylic to nucleophilic attack include converting the carboxylic acid to an acid chloride, an acid anhydride, an acyl azide, an O-acylisourea, a phosphonium derivative or an activated ester, especially those known in the art for activating carboxylic acids for peptide bond formation;

Each R9 is selected from H, CH$_3$, CH$_2$CH$_3$, vinyl, OH, OCH$_3$, NH$_2$, NH(CH$_3$), N(CH$_3$)$_2$, phenyl, F or Cl; most preferably H or CH$_3$, especially H;

Each R0 is selected from H, CH$_3$, CH$_2$CH$_3$ or vinyl, especially H;

m is 1 and n is 3 or 4, m is 2 and n is 4, m is 3 and n is 1 or m is 4 and n is 1 or 2, especially where m is 1 and n is 4;

Each Xaa may be any amino acid residue selected to mimic the amino acid residues in a known alpha helical peptide of interest or to prepare an unknown peptide having new properties. Xaa is preferably a D- or L-alpha amino acid residue. Especially preferred peptides of formula (II) have at least one Xaa which is a D- or L-alpha amino acid residue that is favorable to helix formation. Even more preferred are peptides in which 2 or 3 of Xaa are D- or L-alpha amino acid residues that are favourable to helix formation, for example, alanine, arginine, lysine, methionine, leucine, glutamic acid, glutamine, cysteine, isoleucine, phenylalanine, tyrosine, tryptophan, histidine and aspartic acid, especially alanine, arginine, lysine, methionine, leucine, glutamic acid and glutamine; and L is selected from —NH—C(O)— and —C(O)—NH—.

Scaffolds or macrocyclic modules of formula (II) can be prepared as described for peptides of formula (I).

N-terminal capping groups may and groups which mimic an amino acid side chain may be introduced by methods known in the art. For example the N-terminal amino group may be reacted with a carboxylic acid derivative of the capping group or mimic or an activated carboxylic acid derivative to form an amide bond.

C-terminal capping groups and groups which mimic an amino acid side chain may be introduced by methods known in the art. For example the C-terminal carboxylic acid may be activated and reacted with an amine derivative, preferably a primary amine derivative of the C-terminal capping group or group that mimics an amino acid side chain.

C-terminal carboxylic acid groups or any other carboxylic acid groups that require activation toward nucleophilic substitution can be activated by methods known in the art[95]. For example the carboxylic acid may be activated by conversion to an acyl chloride using $PCl_5$ or $SOCl_2$, conversion to an acyl azide by hydrazinolysis of a protected amino acid or peptide ester followed by treatment with $NaNO_2$ in aqueous acid, conversion to a symmetrical or mixed anhydride using two equivalents of an amino acid and a dicyclohexylcarbodiimide or by reaction with an acid chloride in a dry solvent in the presence of a mild base, conversion to an O-acylisourea by reaction with dicyclohexylcarbodiimide or by conversion to an acyloxyphosphonium or uronium species by reacting a carboxylate anion with a phosphonium or uronium cation, for example, BOP, PyBOP or HBTU.

A representative example of an alpha helical pentapeptide as a scaffold for projecting attached substituents into positions normally occupied the side chains of longer peptides than pentapeptides is given by formula (III):

The scaffold or macrocyclic module may also be incorporated into a multi-macrocyclic structure or may be incorporated into a non-peptidic molecule.

As used herein, the term "macrocyclic module" refers to a cyclic pentapeptide which may be unsubstituted at the N and C termini or may be activated for incorporation into a larger structure. For example, a pentacyclic peptide of formula II in which $R_3$ is H and $R_4$ is H or a group which activates the terminal carboxylic acid carbonyl group to nucleophilic substitution is a macrocyclic module.

Preparation of a non-peptidic molecule incorporating a scaffold or macrocyclic module may be prepared by reacting the N-terminal and/or activated C-terminal of the macrocyclic module with desired non-peptidic moieties.

Alternatively, a number of modules, which may be the same or different, may be prepared as described herein and then consecutively linked to form a multi-macrocyclic peptide that mimics a number of turns of an alpha helix. The multi-macrocyclic peptide may then be used to mimic a protein or polypeptide or part thereof, or may be incorporated into a longer peptide sequence.

Accordingly, in a further aspect of the invention there is provided a conformationally constrained peptide having a plurality of alpha helical pentapeptide sequences, wherein the pentapeptide sequences comprise a sequence of five amino acid residues having a first terminal residue and a second terminal residue that are separated by an intervening sequence of three amino acid residues, and wherein the side chains of the first and second terminal residues are linked to each other.

In a preferred embodiment at least one of the alpha helical pentapeptide sequences is a pentapeptide module of formula (II).

The number of macrocyclic modules in the peptide or polypeptide will depend on the length of the alpha helical portion of the polypeptide required. If the peptide is intended to mimic an alpha helical portion of a known protein or

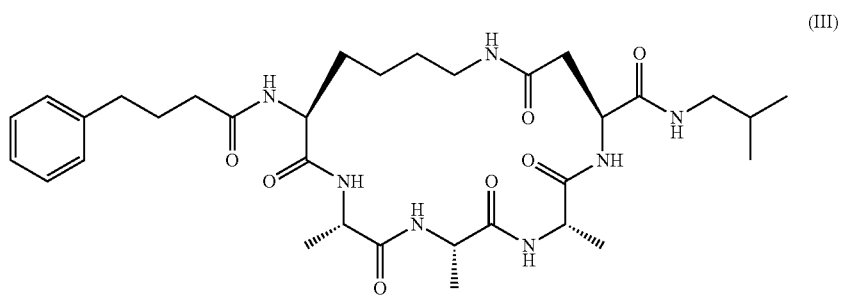 [SMILES: CC(C)CNC(=O)[C@@H]1CC(=O)NCCCC[C@H](NC(=O)CCCc2ccccc2)C(=O)N[C@@H](C)C(=O)N[C@@H](C)C(=O)N[C@@H](C)C(=O)N1]

(III)

The pentapeptide of formula (III) is an example of a peptide of formula (II) in which the three variable amino acid residues that represent Xaa are all alanine, the macrocycle is formed by amide bond formation between a lysine residue and an aspartic acid residue, $R_3$ is an amide formed from the reaction of phenylbutanoic acid and the N-terminal amino group and mimics a phenylalanine side chain, and $R_4$ is an amide formed by the reaction of isobutyl amine with an activated C-terminal carboxylic acid and mimics a valine side chain.

polypeptide, the number of macrocyclic modules will be determined by the number of turns in the alpha helical portion of the known protein or polypeptide. For example, two cyclic pentapeptide modules of Formula (II) could be linked such that the N-terminal nitrogen atom is directly bonded to the C-terminal carbonyl group, to form a 2.8-turn alpha helix. In a similar manner, three consecutively linked cyclic pentapeptide modules would form a 4.2-turn alpha helix, four consecutively linked cyclic pentapeptide modules would form a 5.6-turn alpha helix, five consecutively linked cyclic pentapeptide modules would form a 6.9-turn alpha helix, six consecutively linked cyclic pentapeptide modules would form a 8.3-turn alpha helix and larger alpha helices may be obtained in a similar fashion. In this manner multi-macrocyclic assemblies which are alpha helical in nature can be obtained.

In a preferred embodiment the conformationally constrained peptide having a plurality of alpha helical pentapeptide sequences, is a compound of formula (IV):

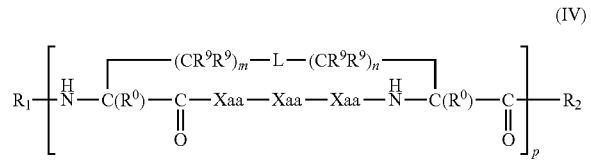

(IV)

wherein each Xaa is independently selected from any amino acid residue;

$R_1$ is selected from H, an N-terminal capping group, a peptide of 1 to 20 amino acid residues optionally capped by an N-terminal capping group, a non-peptidic group or a group that mimics an amino acid side chain;

$R_2$ is selected from H, a C-terminal capping group, a peptide of 1 to 20 amino acids optionally capped by a C-terminal capping group, a group that mimics an amino acid side chain or a group that activates the terminal carboxylic acid carbonyl group to nucleophilic substitution;

each R9 and R0 are independently selected from H, $C_1$-$C_{10}$ alkyl, $C_2$-$C_{10}$ alkenyl, $C_2$-$C_{10}$ alkynyl, $C_3$-$C_{10}$cylcoalkyl, $C_1$-$C_{10}$cycloalkenyl, —OH, —$OC_1$-$C_{10}$ alkyl, —$NH_2$, —NH($C_1$-$C_{10}$alkyl), —N($C_1$-$C_{10}$alkyl)$_2$, $C_6$-$C_{10}$aryl, $C_3$-$C_{10}$heterocyclyl, $C_5$-$C_{10}$heteroaryl and halo;

L is selected from —NH—C(O)—, —C(O)—NH—, —S—S—, —CH(OH)CH$_2$—, CH$_2$CH(OH)—, —CH=CH—, —CH$_2$—CH$_2$—, —NH—CH$_2$— —CH$_2$—NH—, —CH$_2$—S—, —S—CH$_2$—, —C(O)—CH$_2$—, —CH$_2$—C(O)—, —S(O)$_t$—NH—, —NH—S(O)$_t$—, CH$_2$—P(=O)(OH)— and —P(=O)(OH)—CH$_2$—;

m is an integer from 1 to 4,
n is an integer from 1 to 4, and
t is 0, 1 or 2,
wherein m+n=4, 5 or 6 and wherein when m is 2, n is not 3 and when m is 3, n is not 2; and
p is an integer from 2 to 12; with the proviso that bicyclo (Lys$^{13}$-Asp$^{17}$,Lys$^{18}$-Asp$^{22}$) [Ala$^1$, Nlc$^8$, Lys$^{18}$, Asp$^{22}$, Leu$^{27}$] hPTH (1-31) NH$_2$ is excluded.

In preferred embodiments, any one of the following may apply:

$R_1$ is selected from H, an N-terminal capping group that stabilizes the terminus of a helix, usually having hydrogen atoms able to form hydrogen bonds or having a negative charge at the N-terminus to match with the helix dipole, a peptide of 1 to 15, 1 to 10 or 1 to 5 amino acid residues optionally capped with an N-terminal capping group that stabilizes the terminus of a helix, usually having hydrogen atoms able to form hydrogen bonds or having a negative charge at the N-terminus to match with the helix dipole, or a mimic of an amino acid side chain. Suitable N-terminal capping groups include acyl and N-succinate. Suitable groups that mimic an amino acid side chain are any natural or unnatural amino acid side chain that is attached to the N-terminal amino group of the peptide through a carbonyl group derived from a carboxylic acid by formation of an amide bond. Suitable mimics of amino acid side chains include, but are not limited to:

CH$_3$CH$_2$C(O)(CH$_2$)$_u$C(O)—, NH$_2$ (NH=)CNHC(O)(CH$_2$)$_u$C(O)—, H$_2$NC(O)(CH$_2$)$_2$C(O)(CH$_2$)$_u$C(O)—, HOC(O)(CH$_2$)$_2$C(O)(CH$_2$)$_u$C(O)—, HS(CH$_2$)$_2$C(O)(CH$_2$)$_u$C(O)—, H$_2$NC(O)(CH$_2$)$_3$C(O)(CH$_2$)C(O)—, HOC(O)(CH$_2$)$_2$C(O)(CH$_2$)C(O)—, (4-imidazolyl)(CH$_2$)C(O)(CH$_2$)$_u$C(O)—, CH$_3$CH$_2$CH(CH$_3$)CH$_2$C(O)(CH$_2$)$_u$C(O)—, (CH$_3$)$_2$CH(CH$_2$)$_2$C(O)(CH$_2$)C(O)—, H$_2$N(CH$_2$)$_5$C(O)(CH$_2$)$_u$C(O)—, CH$_3$S(CH$_2$)$_3$C(O)(CH$_2$)$_u$C(O)—, Ph(CH$_2$)$_2$C(O)(CH$_2$)$_u$C(O)—, Ph(CH$_2$)$_4$C(O)(CH$_2$)$_u$C(O)—, HO(CH$_2$)$_2$C(O)(CH$_2$)$_u$C(O)—, HOCH(CH$_3$)CH$_2$C(O)(CH$_2$)$_u$C(O)—, (3-indolyl)(CH$_2$)$_2$(CH$_2$)$_u$C(O)—, (4-hydroxyphenyl)(CH$_2$)$_2$C(O)(CH$_2$)$_u$C(O)—, (4-hydroxyphenyl)(CH$_2$)$_3$C(O)(CH$_2$)$_u$C(O)—, (CH$_3$)$_2$CHCH$_2$C(O)(CH$_2$)$_u$C(O)—, CH$_3$CH$_2$CH$_2$C(O)(CH$_2$)$_u$C(O)—, $C_6H_{10}$CH$_2$C(O)(CH$_2$)$_u$C(O)—, $C_5H_8$CH$_2$C(O)(CH$_2$)$_u$C(O)—, CH$_3$C(O)(CH$_2$) C(O)—, CH$_3$(CH$_2$)$_4$C(O)(CH$_2$)C(O)—, CH$_3$ (CH$_2$)$_5$C(O)(CH$_2$)$_u$C(O)—, HOC(O)CH$_2$C(O)(CH$_2$)C(O)—, HS(CH$_2$)C(O)(CH$_2$)$_u$C(O)—, H$_2$N(CH$_2$)$_4$C(O)(CH$_2$)$_u$C(O)— and HOCH$_2$C(O)(CH$_2$)$_u$C(O)— wherein u is 0 or an integer from 1 to 10. The preferred non-peptidic groups enhance the stability, bioavailability or activity of the peptides. Suitable non-peptidic groups include, but are not limited to hydrophobic groups such as carbobenzoxyl, dansyl, t-butyloxycarbonyl, acetyl, 9-fluorenylmethoxycarbonyl, groups which stabilize or mimic alpha-helices, groups which mimic the secondary structure of peptides, particularly alpha helical peptides, such as those disclosed in WO 03/018587, groups which improve bioavailability, such as hydrophilic groups which aid aqueous solubility, for example, cyclodextrans; groups which are recognized by transport receptors to allow or improve transport of the peptides to the site of activity, for example, transport across cell walls or through an epithelial layer such as skin or the gut wall;

$R_2$ is selected from H, a C-terminal capping group that stabilizes the terminus of a helix, usually having hydrogen atoms able to form hydrogen bonds or having a positive charge at the C-terminus to match with the helix dipole, a peptide of 1 to 15, 1 to 10 or 1 to 5 amino acid residues optionally capped with a C-terminal capping group that stabilizes the terminus of a helix, usually having hydrogen atoms able to form hydrogen bonds or having a positive charge at the C-terminus to match with the helix dipole, a mimic of an amino acid side chain or a group which activates the terminal carboxylic acid carbonyl group to nucleophilic substitution. A suitable C-terminal capping group is NH$_2$. Suitable mimics of amino acid side chains are any common or unnatural amino acid side chain that is attached to the C-terminal carbonyl group of the peptide through an amine group by formation of an amide bond. Suitable mimics of amino acid side chains include but are not limited to:

—NH(CH$_2$)$_u$NHCH$_2$CH$_3$, —NH(CH$_2$)NH(CH$_2$)$_4$NHC(=NH)NH$_2$, —NH(CH$_2$)NH(CH$_2$)$_2$C(O)NH$_2$, —NH(CH$_2$)NH(CH$_2$)$_2$CO$_2$H, —NH(CH$_2$)NH(CH$_2$)$_2$SH, —NH(CH$_2$)NH(CH$_2$)$_3$C(O)NH$_2$, —NH(CH$_2$)NH(CH$_2$)$_3$CO$_2$H, —NH(CH$_2$)NH(CH$_2$)$_2$(4-imidazolyl), —NH(CH$_2$)NHCH$_2$CH(CH$_3$)CH$_2$CH$_3$, —NH(CH$_2$)NH(CH$_2$)$_2$CH(CH$_3$)$_2$, —NH(CH$_2$)NH(CH$_2$)$_5$NH$_2$, —NH(CH$_2$)NH(CH$_3$)$_3$SCH$_3$, —NH(CH$_2$)NH(CH$_2$)$_2$(3-indolyl), —NH(CH$_2$)NH(CH$_2$)$_2$(4-hydroxyphenyl), —NH(CH$_2$)NH(CH$_2$)$_3$(4-hydroxyphenyl), —NH(CH$_2$)NHCH$_2$CH(CH$_3$)$_2$, —NH(CH$_2$)NHCH$_2$CH$_2$CH$_3$, —NH(CH$_2$)NHCH$_2$C$_6$H$_{10}$, —NH(CH$_2$)NHCH$_2$C$_5$H$_8$, —NH(CH$_2$)NHCH$_3$, —NH(CH$_2$)NH(CH$_2$)$_4$CH$_3$, —NH(CH$_2$)NH(CH$_2$)$_5$CH$_3$, —NH(CH$_2$)NHCH$_2$CO$_2$H, —NH(CH$_2$)NHCH$_2$SH, —NH(CH$_2$)NH(CH$_2$)$_2$OH, —NH(CH$_2$)NH(CH$_2$)$_5$NH$_2$ and —NH(CH$_2$)NHCH$_2$OH; wherein u is 0 or an integer from 1 to 10.

Suitable groups which activate the C-terminal carboxylic to nucleophilic attack include converting the carboxylic acid to an acid chloride, an acid anhydride, an acyl azide, an O-acylisourea, a phosphonium derivative or an activated ester, especially those known in the art for activating carboxylic acids for peptide bond formation;

The preferred non-peptidic groups enhance the stability, bioavailability or activity of the peptides. Suitable non-peptidic groups include but are not limited to hydrophobic groups such as t-butyl, groups which stabilize or mimic alpha-helices, groups which mimic the secondary structure of peptides, particularly alpha helical peptides, such as those disclosed in WO 03/018587, groups which improve bioavailability, such as hydrophilic groups which aid aqueous solubility, for example, cyclodextrans; groups which are recognized by transport receptors to allow or improve transport of the peptides to the site of activity, for example, transport across cell walls or through an epithelial layer such as skin or the gut wall;

Each R9 is selected from H, $CH_3$, $CH_2CH_3$, vinyl, OH, $OCH_3$, $NH_2$, $NH(CH_3)$, $N(CH_3)_2$, phenyl, F or Cl; most preferably H or $CH_3$, especially H;

Each R0 is selected from H, $CH_3$, $CH_2CH_3$ or vinyl, especially H;

m is 1 and n is 3 or 4, m is 2 and n is 4, m is 3 and n is 1 or m is 4 and n is 1 or 2, especially where m is 1 and n is 4;

Each Xaa may be any amino acid residue selected to mimic the amino acid residues in a known alpha helical peptide of interest or to prepare an unknown peptide having new properties. Xaa is preferably a D- or L-alpha amino acid residue. Especially preferred peptides of formula (IV) have at least one Xaa which is a D- or L-alpha amino acid residue that is favorable to helix formation. Even more preferred are peptides in which 2 or 3 of Xaa are D- or L-alpha amino acid residues that are favorable to helix formation, for example, alanine, arginine, lysine, methionine, leucine, glutamic acid, glutamine, cysteine, isoleucine, phenylalanine, tyrosine, tryptophan, histidine and aspartic acid, especially alanine, arginine, lysine, methionine, leucine, glutamic acid and glutamine;

L is —NH—C(O)— or —C(O)—NH—;

Preferably p is selected to provide the appropriate number of turns in the alpha helix. Especially preferred are those peptides where p is 2 to 11, 2 to 10, 2 to 9 or 2 to 8, 2 to 7, 2 to 6, 2 to 5, 2 to 4, 2 to 3, 3 to 10, 3 to 9, 3 to 8, 3 to 7, 3 to 6, 3 to 5, especially 2 to 5.

Preferred peptides containing more than one consecutive macrocyclic module include those of formula (V):

$$R_1-[1,5\text{-}cyclo(Zaa\text{-}XaaXaaXaa\text{-}Yaa)]_q-R_2 \quad (V)$$

wherein each 1,5-cyclo(Zaa-XaaXaaXaa-Yaa) is independently selected from:

```
cyclo-1,5-KXaaXaaXaaD     [SEQ ID NO: 32]
cyclo-1,5-DXaaXaaXaaK     [SEQ ID NO: 33]
cyclo-1,5-KXaaXaaXaaE     [SEQ ID NO: 34]
cyclo-1,5-EXaaXaaXaaK     [SEQ ID NO: 35]
cyclo-1,5-OXaaXaaXaaD     [SEQ ID NO: 36]
and
cyclo-1,5-DXaaXaaXaaO     [SEQ ID NO: 37]
``` q is an integer from 2 to 12 and $R_1$ and $R_2$ are as defined above.

Illustrative examples of 1,5-cyclo(Zaa-XaaXaaXaa-Yaa) sequences include:

```
cyclo-1,5-KARAD     [SEQ ID NO: 38]
cyclo-1,5-DARAK     [SEQ ID NO: 39]
cyclo-1,5-KARAE     [SEQ ID NO: 40]
cyclo-1,5-EARAK     [SEQ ID NO: 41]
cyclo-1,5-OARAD     [SEQ ID NO: 42]
cyclo-1,5-DARAO     [SEQ ID NO: 43]
cyclo-1,5-KAAAD     [SEQ ID NO: 44]
and
cyclo-1,5-KGSAD.    [SEQ ID NO: 45]
```

In another embodiment, individual macrocyclic modules in the peptide are different.

In yet another embodiment, individual macrocyclic modules in the peptide are the same.

Examples of peptides containing more than one consecutive cyclic pentapeptide module which are very stable alpha helices in water include:

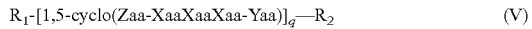

[SEQ ID NO: 46]
cyclo(1-5, 6-10)-Ac-[KARADKARAD]-$NH_2$
and

[SEQ ID NO: 47]
cyclo(1-5, 6-10, 11-15)-Ac-[KARADKARADKARAD]-$NH_2$.

Peptides comprising more than one macrocyclic module can be prepared by conventional solid phase synthesis as described for single macrocycles above, where cyclization occurs while the peptide is still attached to the solid phase resin by incorporation of amino acid residues with suitably protected side chains such as allyl protected aspartic acid or Alloc protected lysine, deprotection and cyclization. Further amino acid residues may be added to the resin bound macrocycle including other amino acid residues with suitable protected side chains, after the addition of five further amino acids, further cyclization may be effected to provide two consecutively linked macrocycles. This may be continued until the desired number of macrocycles is present and then the peptide can be cleaved from the resin.

Alternatively, a single cyclic macrocyclic module may be prepared using solid phase synthesis as hereinbefore described. The single macrocyclic module may be cleaved from the resin and undergo either N-terminal protection or deprotection or C-terminal protection or deprotection. A macrocycle having N-terminal protection and a macrocycle having C-terminal protection may then be reacted with one another by activating the unprotected carboxylic acid to nucleophilic attack by the unprotected amine nitrogen, to provide a multi-macrocyclic structure. Further N-terminal and/or C-terminal protection and deprotection of a single macrocyclic module and a multi-macrocyclic module followed by coupling will allow the preparation of a multi-macrocyclic peptide.

Two macrocyclic modules may be coupled using conventional peptide coupling chemistry. For example, the C-terminal carboxylic acid may be activated by formation of an acid chloride, acid anhydride, an acyl azide, a carbodiimide, an acyloxyphosphonium compound or an active ester, and allowing nucleophilic attack from the N-terminal nitrogen atom. A particularly preferred method of activating the carboxylic acid to nucleophilic attack is preparation of an acyloxyphosphonium derivative of the carboxylic acid, for example, by reaction with the carboxylic acid with BOP, Py-BOP or HBTU in the presence of a tertiary amine such as triethylamine or diisopropylethylamine.

A representative synthesis of a multi-macrocyclic peptide where each macrocyclic module is the same is shown in Scheme 2.

Scheme 2

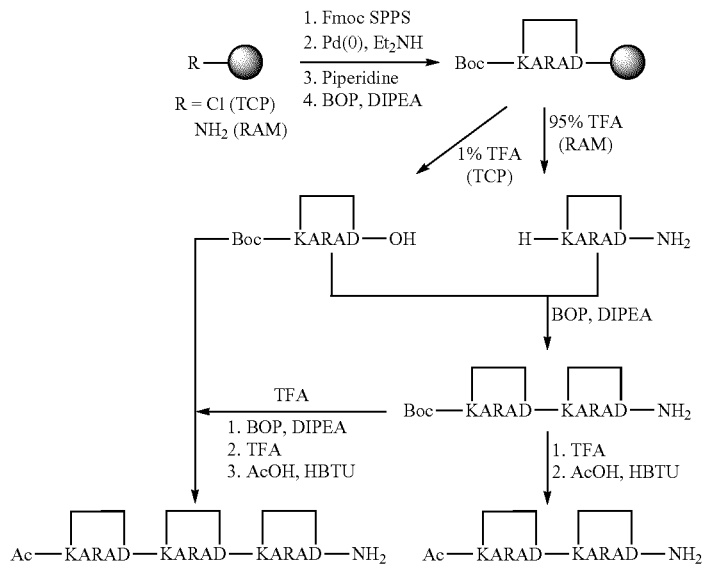

The helically constrained peptides described herein can be synthesized with additional chemical groups present at their amino and/or carboxy termini, such that, for example, the stability, bioavailability, and/or inhibitory activity of the peptides is enhanced. For example, hydrophobic groups such as carbobenzoxyl, dansyl, or t-butyloxycarbonyl groups, may be added to the amino termini. An acetyl group or a 9-fluorenyl-methoxy-carbonyl group may be placed at the amino termini. A hydrophobic group, t-butyloxycarbonyl, or an amido group may be added to carboxy termini. Furthermore, the peptides of the invention can be synthesized such that their steric configuration is altered. For example, the D-isomer of one or more of the amino acid residues of the peptide can be used, rather than the usual L-isomer. The compounds can contain at least one bond linking adjacent amino acids that is a non-peptide bond, and is preferably not helix breaking. Non-peptide bonds for use in flanking sequences include an imino, ester, hydrazine, semicarbazide, oxime, or azo bond. Still further, at least one of the amino acid residues of the peptides of the invention can be substituted by one of the well known non-naturally occurring amino acid residues, that is preferably not helix breaking. Desirably, the non-natural amino acid or non-amide bond linking adjacent amino acids, when present, is present outside of the internal sequence, and is, preferably, not helix breaking. Still further, at least one of the amino acid residues of the peptides of the invention can be substituted by one of the well known non-naturally occurring amino acid residues. Alterations such as these can serve to increase the stability, bioavailability, immunogenicity, and/or inhibitory action of the peptides of the invention.

A representative example of alpha helical cyclic pentapeptides incorporated in a modular fashion into biologically active sequences is described. The opioid receptor-like 1 (ORL-1) is the most recently identified member of the opioid receptor family[137]. Unlike the other three types of opioid receptor ($\mu$, $\delta$, $\kappa$), the ORL-1 receptor does not display affinity for the naturally occurring opioid peptide ligands or for many synthetic opiates that selectively bind $\mu$-, $\delta$-, $\kappa$-receptors[137].

In 1995 the endogenous ligand for the ORL-1 receptor was identified and called nociceptin (NC). Like other opioid receptor peptide ligands nociceptin consists of an N-terminal tetrapeptide which is referred to as the "message" sequence and is primarily responsible for triggering stimulation of the receptor, whilst the remaining C-terminal portion is referred to as the "address" sequence and is involved in binding and receptor specificity[137].

SEQ ID NO: 48

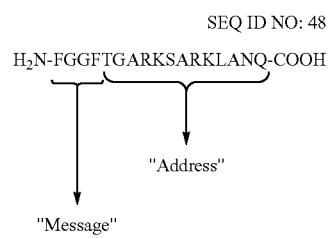

Recent NMR structures of NC and related peptides revealed a highly helical structure in the address domain and suggested amphipathicity[98-139]. Another recent report successfully substituted Aib residues into the NC address sequence resulting in increased potency and affinity in 13-residue peptide sequences. Structure-activity relationship (SAR) studies suggest the minimal sequence is $NC_{1-13}$. An alanine scan showed the first five residues (FGGFT) are critical, whilst G6 and A7 appear to tolerate substitution, R8 is highly crucial, whilst the remaining residues are necessary but tolerate alanine substitution[138]. Another recent report identified a pure, selective peptide antagonist of the ORL-1 receptor which involved replacing the first residue in the native sequence with Nphe[137]

Since the present invention establishes a general method for constraining short peptides into alpha helical conformations, nociceptin is an ideal target to show that constraining biologically important helices into an alpha helical conformation can improve activity and affinity. Thus the peptides of SEQ ID NOs: 49 to 51 were designed using the available SAR. The peptide of SEQ ID NO: 49 is designed to be a nociceptin mimetic for agonism, whilst the peptide of SEQ ID NO: 50 is based on the recently reported antagonist [Nphel] NC (1-15). The peptide of SEQ ID NO: 51 consists of just the address sequence and the inventors consider that if this peptide has sufficiently high affinity for the receptor it may function as an antagonist. There are no studies to date on peptides incorporating only the address sequence.

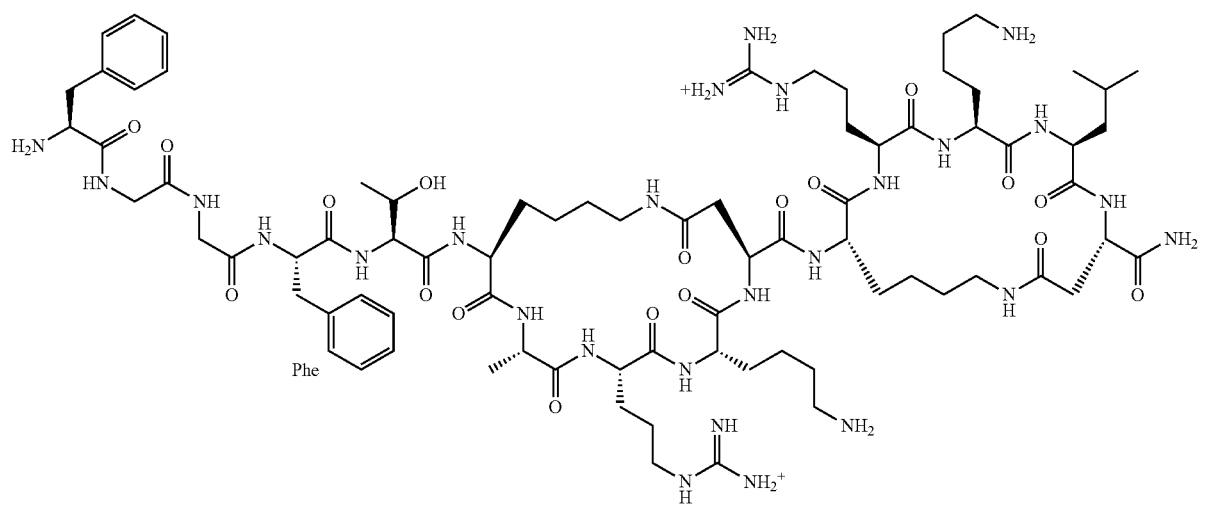

FGFT[1,4-cyclo(KARKD)][1,4-cyclo(KRKLD)]-NH₂

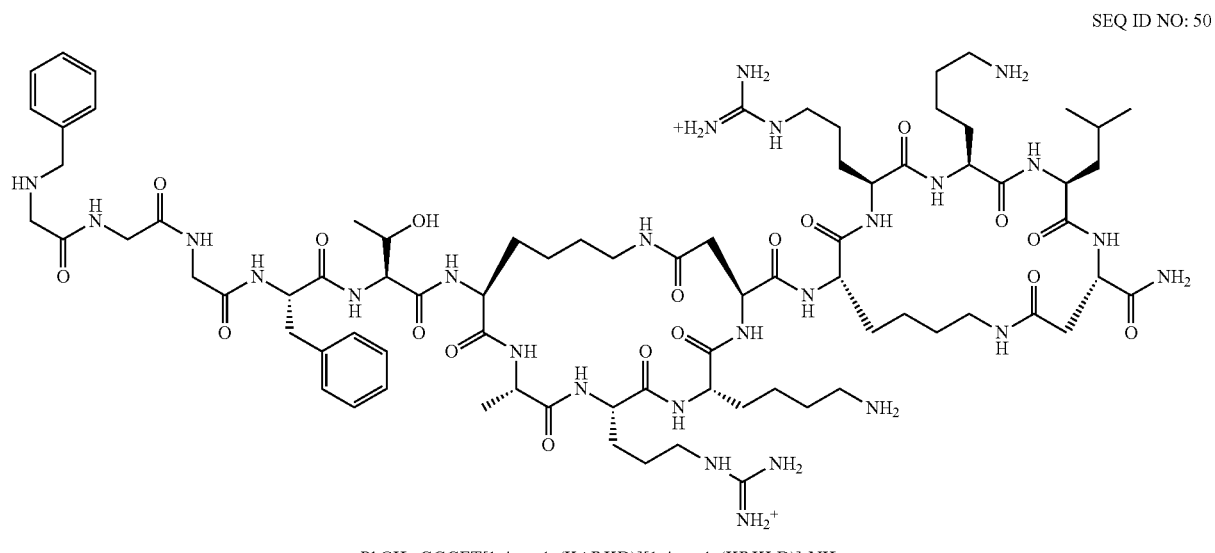

PhCH₂-GGGFT[1,4-cyclo(KARKD)][1,4-cyclo(KRKLD)]-NH₂

-continued

SEQ ID NO: 51

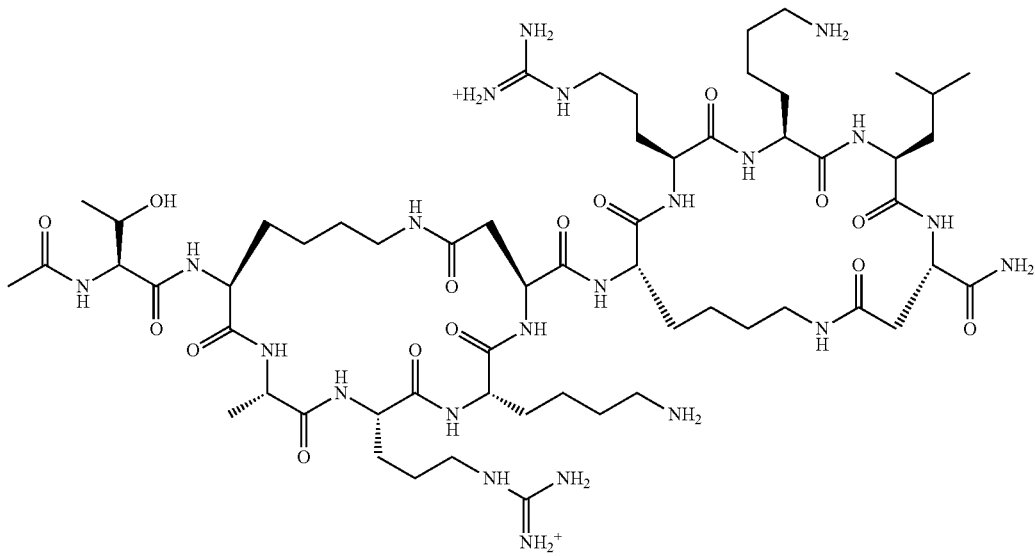

Ac-T-[1,4-cyclo(KARKD)][1,4-cyclo(KRKLD)]-NH₂

The reaction scheme for the synthesis of the Nociceptin mimetics of SEQ ID NOs: 49 to 51 is shown in Scheme 3. The 2-hydroxy-4-methoxybenzyl protecting group is used during synthesis of multi-macrocyclic compounds, however this group is removed during deprotection and cleavage of the peptides from the resin.

Scheme 3

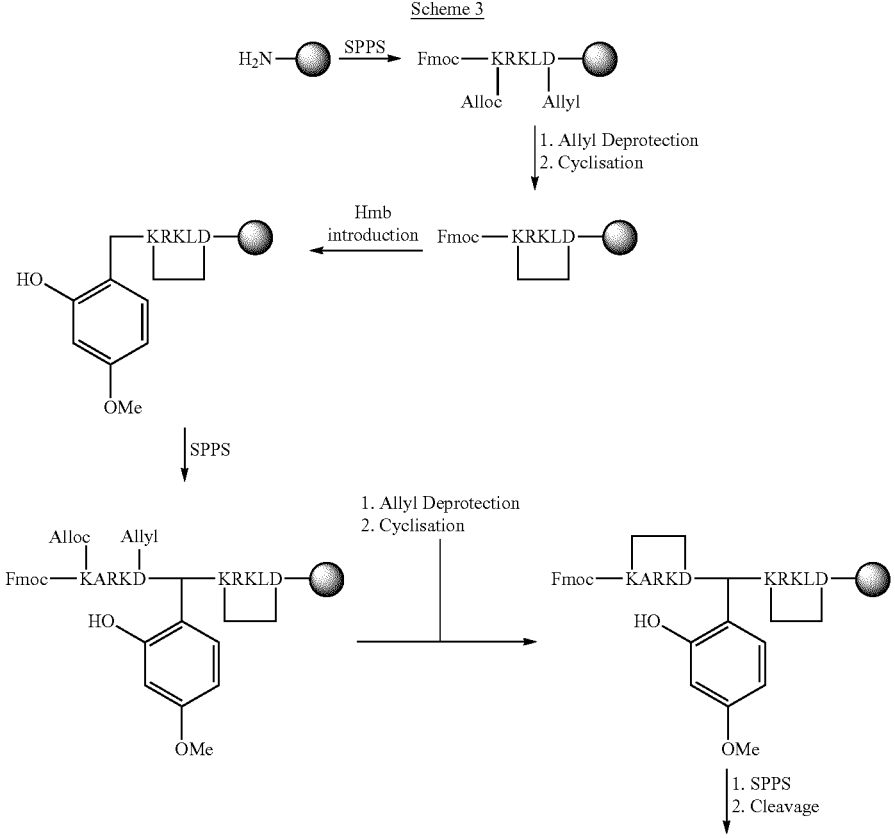

SEQ ID NOs: 49-51

The present invention also provides compositions which comprise one or more compounds of the invention. The compounds themselves may be present in the compositions in any of a wide variety of forms. For example, two or more compounds may be merely mixed together or may be more closely associated through complexation, crystallization, or ionic or covalent bonding.

Those of skill in the art will appreciate that a wide variety of prophylactic, diagnostic, and therapeutic treatments may be prepared from the compounds and compositions of the present invention, due in large part to the cross-reactivity—i.e., agonism or antagonism—of the macrocyclic moieties of the compounds with one or more naturally-occurring peptides or polypeptides. Thus, a compound of the present invention finds utility as a molecular mimic or antagonist of a member of a ligand-receptor binding pair that underlies or is otherwise associated with the development of a particular disease or condition, wherein the ligand-receptor interaction is mediated at least in part by one or more alpha helical motifs present in the ligand or the receptor. Accordingly, in some embodiments, a compound of the present invention having one or more macrocyclic moieties that antagonize the interaction of a ligand and a receptor will be useful in the prevention or treatment of a disease or condition that results from inappropriate activation of the receptor by the ligand. In other embodiments, a disease or condition may arise through inadequate activation of a receptor, in which case the disease or condition may be treated or prevented by means of a compound having one or more macrocyclic moieties that mimic the binding determinants of the ligand or the receptor. Illustrative diseases or conditions mediated by alpha-helix associated ligand-receptor interactions include diseases or conditions related to DNA transcription, diseases related to RNA reverse transcription, diseases or disorders related to transcriptional antitermination, diseases related to apoptosis regulation and tumor suppression, for example, cancers such as brain tumors, breast cancer, lung cancer, bone cancer, colon cancer, ovarian cancer, testicular cancer, renal cancer, liver cancer, lymphoma and leukemia; diseases or disorders related to calcium homeostasis, diseases or disorders related to pain transmission, diseases or disorders associated with lipid metabolism and cholesterol homeostasis, diseases and disorders related to stress response, or to anxiety, appetite, alcohol withdrawal, opiate withdrawal or epilepsy.

Thus, a further aspect of the invention contemplates a method for treating or preventing a disease or condition associated with a ligand-receptor interaction that is mediated at least in part by an alpha helical domain present in the ligand or the receptor, comprising administering an effective amount of a compound comprising at least one alpha helical cyclic peptide, wherein each peptide comprises a sequence of five amino acid residues having a first terminal residue and a second terminal residue that are separated by an intervening sequence of three amino acid residues, and wherein the side chains of the first and second terminal residues are linked to each other and wherein the side chains of at least some of the amino acid residues of the or each peptide are in a (three-dimensional) configuration that is analogous to the configuration of amino acid side chains of at least a portion of the alpha helical domain of the ligand or the receptor. Preferably the compound is a compound of any one of formula (I), (II) or (IV).

As used herein, the term "effective amount" relates to an amount of compound which, when administered according to a desired dosing regimen, provides the desired mediation of the disease or disorder, therapeutic activity or disease prevention. Dosing may occur at intervals of minutes, hours, days, weeks, months or years or continuously over any one of these periods. A therapeutic, or treatment effective amount is an amount of the compound which, when administered according to a desired dosing regimen, is sufficient to at least partially attain the desired therapeutic effect, or delay the onset of, or inhibit the progression of or halt or partially or fully reverse the onset or progression of the disease or disorder. A prevention effective amount of compound which when administered to the desired dosing regimen is sufficient to at least partially prevent or delay the onset of a particular disease or condition.

Yet another aspect of the invention provides a use of a compound comprising an alpha helical cyclic peptide, wherein the peptide comprises a sequence of five amino acid residues having a first terminal residue and a second terminal residue that are separated by an intervening sequence of three amino acid residues, and wherein the side chains of the first and second terminal residues are linked to each other, in the preparation of a medicament for the treatment or prevention of a disease or disorder mediated by the interaction of alpha helical peptides with biomolecules.

Suitable dosages may lie within the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another preferred embodiment, the dosage is in the range of 1 mg to 100 mg per kg of body weight per dosage, such as up to 50 mg per kg of body weight per dosage. In yet another embodiment, the dosage is in the range of 1 µg to 1 mg per kg of body weight per dosage.

Suitable dosage amounts and dosing regimens can be determined by the attending physician and may depend on the severity of the condition as well as the general age, health and weight of the subject.

The active ingredient may be administered in a single dose or a series of doses. While it is possible for the active ingredient to be administered alone, it is preferable to present it as a composition, preferably as a pharmaceutical composition.

According to a further aspect, the invention contemplates a pharmaceutical composition comprising a compound comprising an alpha helical cyclic peptide, wherein the peptide comprises a sequence of five amino acid residues having a first terminal residue and a second terminal residue that are separated by an intervening sequence of three amino acid residues, and wherein the side chains of the first and second terminal residues are linked to each other, or a conformationally constrained peptide having a plurality of alpha helical pentapeptide sequences, wherein the pentapeptide sequences comprise a sequence of five amino acid residues having a first terminal residue and a second terminal residue that are separated by an intervening sequence of three amino acid residues, and wherein the side-chains of the first and second terminal residues are linked to each other, or a pharmaceutically acceptable salt thereof and a pharmaceutically acceptable carrier, excipient or diluent.

Suitable pharmaceutically acceptable salts include, but are not limited to, salts of pharmaceutically acceptable inorganic acids such as hydrochloric, sulfuric, phosphoric, nitric, carbonic, boric, sulfamic, and hydrobromic acids, or salts of pharmaceutically acceptable organic acids such as acetic, propionic, butyric, tartaric, maleic, hydroxymaleic, fumaric, malic, citric, lactic, mucic, gluconic, benzoic, succinic, oxalic, phenylacetic, methanesulphonic, toluenesulphonic, benzenesulphonic, salicylic, sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, zinc, ammonium, alkylammonium such as salts formed from triethylamine, alkoxyammonium such as those formed with ethanolamine and salts formed from ethylenediamine, choline or amino acids such as arginine, lysine or histidine.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

The formulation of such compositions is well known to those skilled in the art. The composition may contain pharmaceutically acceptable additives such as carriers, diluents or excipients. These include, where appropriate, all conventional solvents, dispersion agents, fillers, solid carriers, coating agents, antifungal and antibacterial agents, dermal penetration agents, surfactants, isotonic and absorption agents and the like. It will be understood that the compositions of the invention may also include other supplementary physiologically active agents.

The carrier must be pharmaceutically acceptable in the sense of being compatible with the other ingredients of the composition and not injurious to the subject. Compositions include those suitable for oral, rectal, inhalational, nasal, transdermal, topical (including buccal and sublingual), vaginal or parenteral (including subcutaneous, intramuscular, intraspinal, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Depending on the disease or condition to be treated, it may or may not be desirable for a compound of Formula (I) or (IV) to cross the blood/brain barrier. Thus the compositions for use in the present invention may be formulated to be water or lipid soluble.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (eg inert diluent, preservative, disintegrant (eg. sodium starch glycolate, cross-linked polyvinyl pyrrolidone, cross-linked sodium carboxymethyl cellulose)) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavored base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

The compounds of Formula (I) or (IV) may also be administered intranasally or via inhalation, for example by atomizer, aerosol or nebulizer means.

Compositions suitable for topical administration to the skin may comprise the compounds dissolved or suspended in any suitable carrier or base and may be in the form of lotions, gel, creams, pastes, ointments and the like. Suitable carriers include mineral oil, propylene glycol, polyoxyethylene, polyoxypropylene, emulsifying wax, sorbitan monostearate, polysorbate 60, cetyl esters wax, cetearyl alcohol, 2-octyldodecanol, benzyl alcohol and water. Transdermal devices, such as patches, may also be used to administer the compounds of the invention.

Compositions for rectal administration may be presented as a suppository with a suitable carrier base comprising, for example, cocoa butter, gelatin, glycerin or polyethylene glycol.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question, for example, those suitable for oral administration may include such further agents as binders, sweeteners, thickeners, flavoring agents, disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavoring agents include peppermint oil, oil of wintergreen, cherry, orange or raspberry flavoring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

BRIEF DESCRIPTION OF THE FIGURES

FIG. 8 depicts (a) Helical wheel for dimer SEQ ID NO: 46, cyclo(1-5,6-10)-Ac-[KARADKARAD]—NH$_2$ showing side chain distribution; (b) side view of SEQ ID NO: 46 with helical backbone (yellow), bridging lactam restraints (white), exposed side chains (green spheres); and (c) SEQ ID NO: 46 viewed end on.

Figure 1A:
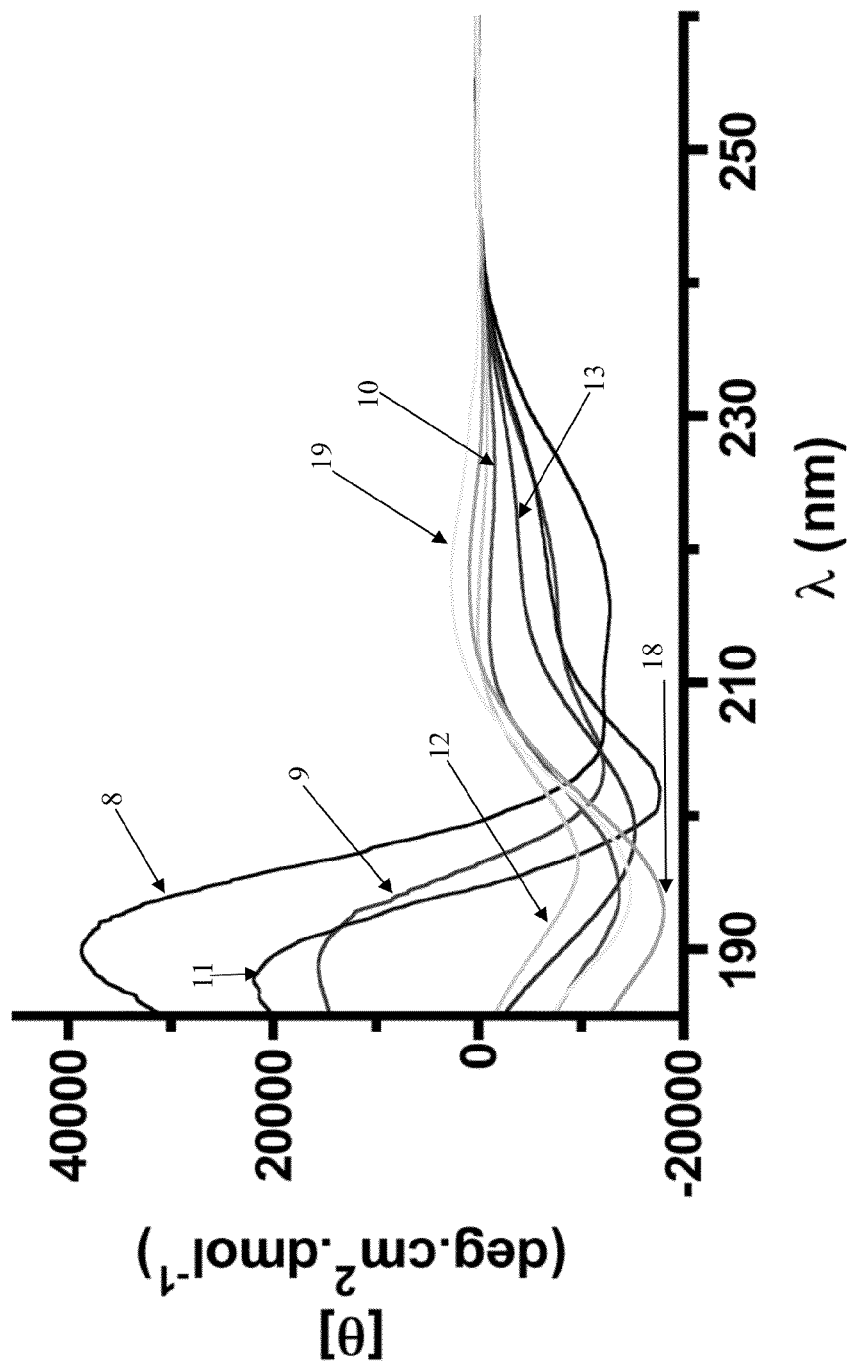
FIG. 1A depicts a CD spectra of cyclic pentapeptides SEQ ID NOs: 8, 9, 10, 11, 12, 13, 18, and 19 in 10 mM phosphate buffer (pH 7.4, 25° C.).

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention will now be described with reference to the following examples which are included for the purpose of illustration only and are not intended to limit the generality of the invention hereinbefore described.

EXAMPLES

Example 1

Peptide Synthesis (Pentapeptides and Hexapeptides)

Peptides represented by SEQ ID NO. 8 to SEQ ID NO: 31 were prepared on 0.25 mmol scale by manual stepwise solid phase peptide synthesis using HCTU/DIPEA activation for Fmoc chemistry on Rink Amide MBHA resin (substitution 0.78 mmol·g$^{-1}$), or Tentagel S RAM resin (substitution 0.25 mmol·g), or Trityl chloride resin (substitution 1.0 mmol·g$^1$). Four equivalents of amino acid and eight equivalents of diisopropylethylamine (DIPEA) were employed in each coupling step (45 mins), except for Fmoc-Asp (OAllyl)-OH and Fmoc-Lys (Alloc)-OH where only 2 equivalents were used. Fmoc deprotections were achieved with 3×5 min treatments with excess 1:1 piperidine:DMF. Coupling yields were monitored by quantitative ninhydrin assay[51] and double couplings were employed for yields below 99.6%. After the assembly was complete, the allyl ester of aspartic acid and allyl carbamate of lysine were removed by treating the peptide resin with Pd(PPh$_3$)$_4$ (0.1 eq) and N,N-dimethylbarbituric acid (4 eq), in DCM, under argon and in the dark for 2 hrs, this procedure was repeated once. After which the peptide was washed with DCM, DMF and 0.5% diethyldithiocarbamate in DMF. 2 mg of resin was subjected to cleavage and the progress of the reaction monitored by MS. This process was repeated if necessary.

Cyclization was effected on-resin using 1.5 eq BOP, 2 eq DIPEA in DMSO/NMP (1:4). The reaction was monitored by cleavage of ~2 mg resin and subjecting the residue to MS, total reaction time was <24 hours. The peptides were simultaneously deprotected and cleaved from the resin by 2 hr treatment of the washed and dried resin in 95% TFA, 2.5% TIPS, 2.5% H$_2$O, or 1% TFA in DCM (15 μl per 10 mg resin). The solution was then filtered, the filtrate concentrated in vacuo and the peptide precipitated with cold diethyl ether. The peptide precipitate was filtered washed with copious amounts of diethyl ether, redissolved in 1:1 acetonitrile/water and lyophilised. The crude peptides were purified by rp-HPLC(R$_{t1}$:Vydac C18 column, 300 Å. 22×250 mm, 214 nm, Solvent A=0.1% TFA in H$_2$O, Solvent B=0.1% TFA, 10% H$_2$O in Acetonitrile. Gradient: 0% B to 100% B over mins. R$_{t2}$:Phenomenex C18 column, 300 Å. 22×250 mm, 214 nm, Solvent A=0.1% TFA in H$_2$O, Solvent B=0.1% TFA, 10% H$_2$O in Acetonitrile. Gradient: 0% B to 100% B over 30 mins.). $^1$H NMR was carried out in H$_2$O:D$_2$O (9:1) at 298K.

Example 2

Cyclic Pentapeptides with Non-Peptidic Capping Groups

Synthesis of the peptide of formula (II) was achieved by standard Fmoc SPPS protocols using trityl chloride polystyrene resin. The peptide was capped with phenyl butanoic acid, cleaved from the resin using 1% TFA in dichloromethane (DCM) leaving side chain protecting groups intact. Isobutylamine was then coupled on using BOP, DIPEA, with CuCl$_2$—an additive known to minimize racemisation of the C-terminal residue. Following this final deprotection was effected with 95% TFA, 2.5% TIPS, 2.5% H$_2$O.

Example 3

N-Terminal Cyclic Pentapeptide Building Block

NH$_2$-(cyclo-1-5)-KARAD-NH$_2$ (SEQ ID NO. 52) was prepared by manual stepwise solid phase peptide synthesis using HBTU/DIPEA activation for Fmoc chemistry[107] on Rink Amide MBHA resin (substitution 0.78 mmol·g$^{-1}$, 1.56 mmol, 2000 mg). Four equivalents of amino acid and eight equivalents of diisopropylethylamine (DIPEA) were employed in each coupling step (45 mins), except for Fmoc-Asp(OAllyl)-OH and Boc-Lys(Fmoc)-OH where only 2 equivalents were used. Fmoc deprotections were achieved with 3×5 min treatments with excess 1:1 piperidine:DMF. Coupling yields were monitored by quantitative ninhydrin assay[108] and double couplings were employed for yields below 99.6%. After the assembly was complete, the allyl ester of aspartic acid was removed by treating the peptide resin with Pd(PPh$_3$)$_4$ (0.05 eq) and diethylamine (5 eq) in DCM, under argon and in the dark for 2 hrs. After which the peptide was washed with DCM, DMF and 0.5% diethyldithiocarbamate in DMF. 2 mg of resin was subjected to cleavage and the progress of the reaction monitored by Mass spectrometry (MS). This process was repeated if necessary. Following Allyl ester deprotection the N(ζ)-Fmoc group was removed by treatment with piperidine (1:1 in DMF). Cyclization was effected on-resin using 1.5 eq BOP, 2 eq DIPEA in DMF/Benzene (2:1). The reaction was monitored by cleaving ~2 mg resin and subjecting the residue to MS, total reaction time was approximately 48-72 hours. The peptides were simultaneously deprotected and cleaved from the resin by 2 hr treatment of the washed and dried resin in 95% TFA, 2.5% TIPS, 2.5% H$_2$O (15 μl per 10 mg resin). The solution was then filtered, the filtrate concentrated in vacuo and the peptide precipitated with cold diethyl ether. The peptide precipitate was filtered washed with copious amounts of diethyl ether, redissolved in 1:1 acetonitrile/water and lyophilised. The crude peptides were purified by rp-HPLC (Vydac C18 column, 300 Å. 22×250 mm, 214 nm, Solvent A=0.1% TFA in H$_2$O, Solvent B=0.1% TFA, 10% H$_2$O in Acetonitrile. Gradient: 0% B to 100% B over 30 mins. Yield 30% (isolated). [R$_t$=12.82 min]. MS: [M+H$^+$](calc.)=calc. 541.31 (expt.)=541.39.

Example 4

C-Terminal Cyclic Pentapeptide Building Block

Boc-(cyclo-1-5)-KAR(Pbf)AD-OH (SEQ ID NO: 53) was synthesized in an analogous manner to peptide (SEQ ID NO: 52 above), however using trityl chloride resin (0.95 mmol·g$^{-1}$, 1.28 g, 1.16 mmol). Cleavage was achieved using 50 mL 10% acetic acid, 20% 2,2,2-trifluoroethanol, 70% DCM for 2 hrs. After lyophilization the crude peptide was deemed pure enough by analytical HPLC and used without further purification. Yield 50%. MS: [M+H$^+$](calc)=893.43 (expt.)=893.67].

Example 5

Synthesis of cyclo(1-5,6-10)-Ac-[KARADKARAD]—NH$_2$ [SEQ ID NO: 46]

To DIPEA (135 μL, 0.38 mmol) was added to a solution of Boc-cyclo(1-5)-KAR(Pbf)AD-OH [SEQ ID NO: 53](154 mg, 0.17 mmol), NH$_2$-cyclo(1-5)-KARAD-NH$_2$ [SEQ ID NO: 52](102 mg, 0.19 mmol, and BOP (80 mg, 0.18 mmol) in DMF (5 mL). After stirring (2 h, RT), solvent was evaporated in vacuo, the residue dissolved in H$_2$O/MeCN (1:1), lyophilized and purified (rpHPLC). The product was treated with TFA/TIPS19:1 (1 h, 20° C.), evaporated, and reacted (2 h, 20° C.) with AcOH (15 μL, 0.26 mmol), 0.5M HBTU (500 μL 0.25 mmol) and DIPEA (90 μL, 0.52 mmol). Solvent was removed in vacuo, H$_2$O/MeCN (1:1) added, lyophilized and purified (rpHPLC) to yield cyclo(1-5,6-10)-Ac-[KARAD-KARAD]—NH$_2$ [SEQ ID NO: 46](19.1 mg, 10% isolated). MS [M+H$^+$](calc.) 1106.6 (expt.) 1106.97, [M+2H]/2 (calc.)=554.3 (expt.)=554.04. Anal. rpHPLC: 14.8 min. (Gradient 0%-100% acetonitrile over 30 min).

Example 6

Synthesis of cyclo(1-5,6-10, 11-15)-Ac-[KARADKARADKARAD]—NH$_2$ [SEQ ID NO: 45]

DIPEA (135 μL, 0.38 mmol) was added to a solution of Boc-(cyclo1-5)-KAR(Pbf)AD-OH [SEQ ID NO: 53](66 mg, 0.077 mmol), NH$_2$—(cyclo1-5)-KARAD-NH$_2$ [SEQ ID NO: 52](42 mg, 0.074 mmol, and BOP (52 mg, 0.154 mmol) in DMF (5 mL). After stirring (2 h, RT), solvent was evaporated in vacuo, the residue dissolved in H$_2$O/MeCN (1:1), lyophilized and purified (rpHPLC). The product (34 mg, 0.024 mmol) was treated with TFA/TIPS 19:1 (1 h, 20° C.), evaporated, and reacted (2 h, RT) with peptide Boc-(cyclo1-5)-KAR(Pbf)AD-OH ([SEQ ID NO: 53](20 mg, 0.024 mmol), BOP (15 mg, 0.034 mmol), and lastly DIPEA (50 μL, 0.24 mmol). The solvent was evaporated in vacuo, the residue dissolved in H$_2$O/MeCN (1:1), lyophilized and purified (rpHPLC). The product was once again treated with TFA/TIPS 19:1 (1 h, 20° C.), evaporated, and reacted with AcOH (2 μL, 0.0132 mmol), BOP 7 mg, 0.016 mmol) and DIPEA (19 μL, 0.138 mmol) for 2 hrs at RT. The solvent was removed in vacuo, H$_2$O/MeCN (1:1) added, lyophilized and purified (rpHPLC) to yield cyclo (1-5,6-10, 11-15)-Ac-[KARADKARADKARAD]—NH$_2$ [SEQ ID NO: 47](7.8 mg, 5.5% (isolated). MS [M+2H$^+$]/2 (calc.)=815.44 (expt.)=815.55. [M+3H]/3 (calc.)=543.97 (expt.)=544.03. Anal. rpHPLC: 15.09 min.

Example 7

Non-Cyclic Analogues

Linear Peptides Ac(KARAD)$_n$-NH$_2$ where n=2 (SEQ ID NO: 54) and n=3 (SEQ ID NO: 55) were prepared by manual stepwise solid phase peptide synthesis using HBTU/DIPEA activation for Fmoc chemistry[107] on Rink Amide MBHA resin (substitution 0.78 mmol·g$^{-1}$, 0.5 mmol, 648 mg). Four equivalents of amino acid and eight equivalents of diisopropylethylamine (DIPEA) were employed in each coupling step (45 min). Fmoc deprotections were achieved with 3×5 min treatments with excess 1:1 piperidine:DMF. Coupling yields were monitored by quantitative ninhydrin assay[108] and double couplings were employed for yields below 99.6%. After assembly of the first 10 residues, the peptide resin was washed, dried and split into two portions, one portion was acetylated, whilst to the other was added the final 5 residues. N-terminal acetylation was achieved by treating the fully protected peptide with 4 equivalents of glacial acetic acid, 4 equivalents of HBTU, and 8 equivalents of DIPEA. The peptides were simultaneously deprotected and cleaved from the resin by 2-hr treatment of the washed and dried resin in 95%

TFA, 2.5% TIPS, 2.5% H$_2$O (15 µL per 10 mg resin). The solution was then filtered, the filtrate concentrated in vacuo and the peptide precipitated with cold diethyl ether. The peptide precipitate was filtered washed with copious amounts of diethyl ether, redissolved in 1:1 acetonitrile/water and lyophilized. The crude peptides were purified by rp-HPLC (Vydac C18 column, 300 Å. 22×250 mm, 214 nm, Solvent A=0.1% TFA in H$_2$O, Solvent B=0.1% TFA, 10% H$_2$O in Acetonitrile. Gradient: 0% B to 100% B over 30 mins. (SEQ ID NO: 54) Yield 20% (isolated). [R$_t$=12.65 min]. MS: [M+H$^+$](calc.)=1142.63 (expt.)=1142.75; [M+2H$^+$]/2 (calc.) 571.85 (expt.)=571.86. (SEQ ID NO: 55) Yield 30% (isolated) [R$_t$=13.16 min]. MS: [M+2H$^+$]/2 (calc.)=842.46 (expt.)=842.64; [M+3H]/3 (calc.) 561.98 (expt.)=562.08.

Example 8

Synthesis of SEQ ID NOs: 77 to 79 was carried on Tentagel-S-RAM resin (0.25 mmol scale) by manual stepwise solid phase peptide synthesis using HCTU/DIPEA activation Tentagel-S-RAM resin using standard Fmoc SPPS (scheme), Four equivalents of amino acid and eight equivalents of diisopropylethylamine (DIPEA) were employed in each coupling step (45 mins), except for Fmoc-Asp(OAllyl)-OH and Fmoc-Lys(Alloc)-OH where only 2 equivalents were used. Fmoc deprotections were achieved with 3×5 min treatments with excess 1:1 piperidine:DMF. Coupling yields were monitored by quantitative ninhydrin assay and double couplings were employed for yields below 99.6%. After the assembly was complete, the allyl ester of aspartic acid and allyl carbamate of lysine were removed by treating the peptide resin with Pd(PPh$_3$)$_4$ (0.1 eq) and N,N-dimethylbarbituric acid (4 eq), in DCM, under argon and in the dark for 2 hrs, this procedure was repeated once. After which the peptide was washed with DCM, DMF and 0.5% diethyldithiocarbamate in DMF. 2 mg of resin was subjected to cleavage and the progress of the reaction monitored by MS. This process was repeated if necessary.

Cyclization was effected on-resin using 1.5 eq BOP, 2 eq DIPEA in DMSO/NMP (1:4). The reaction was monitored by cleavage of ~2 mg resin and subjecting the residue to MS, total reaction time was <24. After subsequent piperidine deprotection, the resin was shaken with 2-hydroxy-4-methoxybenzaldehyde in dimethylormamide/trimethylorthoformate (1:1) for 10 hr, the resin was then drained and NaBH(OAc)$_3$ (10 eq) in dimethylormamide/trimethylorthoformate (1:1). The ninhydrin test indicated that the 2-hydroxy-4-methoxybenzyl had successfully (>99.4%) been introduced onto Na of lysine. The resin was then acylated overnight with the symmetrical anhydride of Fmoc-Asp(OAll)-OH (generated by stirring 6 eq Fmoc-Asp(OAll)-OH, and 3 eq Diisopropylcarbodimide in DCM for 30 mins). Cleavage of a small amount of resin and analysis by MS indicated complete N acylation after 24 hrs. The remaining residues were introduced using the standard HCTU/DIPEA activation, and allyl deprotection and macrolactamization was achieved as previously described. After attachment of the final 5 residues the peptide resin was deprotected, washed and dried. Final cleavage of the peptides was achieved with 92.5% TFA, 2.5% TIPS, 2.5% EDT, 2.5% H$_2$O. The solution was then filtered, the filtrate concentrated in vacuo and the peptide precipitated with cold diethyl ether. The peptide precipitate was filtered washed with copious amounts of diethyl ether, redissolved in 1:1 acetonitrile/water and lyophilised. The crude peptides were purified by rp-HPLC (R$_t$1:Vydac C18 column, 300 Å. 22×250 mm, 214 nm, Solvent A=0.1% TFA in H$_2$O, Solvent B=0.1% TFA, 10% H$_2$O in Acetonitrile. Gradient: 0% B to 100% B over 30 mins. R$_t$2:Phenomenex C18 column, 300 Å. 22×250 mm, 214 nm, Solvent A=0.1% TFA in H$_2$O, Solvent B=0.1% TFA, 10% H$_2$O in Acetonitrile. Gradient: 0% B to 100% B over 30 mins.).

Example 9

CD and NMR Studies on Cyclic Penta and Hexapeptides

Circular Dichroism (CD) was performed on peptides having SEQ ID NOs: 8 to 14 and 18 to 31, using methods described above. The molar elipticities at 222 nm, 208 nm and 190 nm, ratios of elipticities at 222 nm/208 nm and relative helicity are shown in Tables 6 and 7. CD spectra of these peptides are given in FIG. 1.

TABLE 6

CD spectra on peptides having one cyclic pentapeptide module - effects of varying the bridge partner and the termini Molar elipticities ([θ] deg.cm$^2$.dmol$^{-1}$.residue$^{-1}$) at λ = 215, 207 and 190 nm, ratios of elipticities at 215/207 nm, and percentage helicity for peptides in 10 mM phosphate buffer (pH 7.4, 25° C).

| Peptide | [θ]$_{215}$ | [θ]$_{207}$ | [θ]$_{190}$ | θ$_{215}$/θ$_{207}$ | Relative helicity[c] |
|---|---|---|---|---|---|
| Ac-(cyclo-1,5)-[KARAE]-NH$_2$ [SEQ ID NO: 10] | −1068 | −3393 | −10611 | 0.31 | 0.08 |
| Ac-(cyclo-1,5)-[EARAK]-NH$_2$ [SEQ ID NO: 11] | −7430 | −12803 | 20735 | 0.58 | 0.58 |
| Ac-(cyclo-1,5)-[KARAD]-NH$_2$ [SEQ ID NO: 8] | −12757 | −12211 | 38300 | 1.04 | 1.00 |
| Ac-(cyclo-1,5)-[DARAK]-NH$_2$ [SEQ ID NO: 9] | −7723 | −10705 | 15600 | 0.72 | 0.60 |
| Ac-(cyclo-1,5)-[OARAD]-NH$_2$ [SEQ ID NO: 12] | 92 | −2077 | −4613 | −0.04 | 0 |
| Ac-(cyclo-1,5)-[DARAO]-NH$_2$ [SEQ ID NO: 13] | −4671 | −9748 | −6954 | 0.48 | 0.37 |

TABLE 6-continued

CD spectra on peptides having one cyclic pentapeptide module -
effects of varying the bridge partner and the termini
Molar elipticities ([θ] deg.cm². dmol⁻¹.residue⁻¹) at λ = 215,
207 and 190 nm, ratios of elipticities at 215/207 nm, and
percentage helicity for peptides in 10 mM phosphate buffer
(pH 7.4, 25° C).

| Peptide | $[\theta]_{215}$ | $[\theta]_{207}$ | $[\theta]_{190}$ | $\theta_{215}/\theta_{207}$ | Relative helicity[c] |
|---|---|---|---|---|---|
| Ac-(cyclo-1,5)-[OARAE]-NH₂ [SEQ ID NO: 18] | 741 | −3368 | −16228 | −0.22 | 0 |
| Ac-(cyclo-1,5)-[EARAO]-NH₂ [SEQ ID NO: 19] | 2442 | −1917 | −11256 | −1.27 | 0 |
| Ac-KARAD-NH₂ [SEQ ID NO: ZZ14] | −524 | −5555 | −7372 | 0.09 | 0.04 |
| Ac-(cyclo-1,5)-[KARAD]-OH [SEQ ID NO: 20] | 207 | −5643 | −13953 | −0.04 | 0 |
| [a] | −625 | −3195 | −2659 | 0.20 | 0.06 |
| H-(cyclo-1,5)-[KARAD]-NH₂ [SEQ ID NO: 21] | −812 | −2228 | 1355 | 0.36 | 0.06 |
| [b] | −2590 | −3327 | 8452 | 0.78 | 0.2 |
| H-(cyclo-1,5)-[KARAD]-OH [SEQ ID NO: 22] | −1033 | −5737 | −4966 | 0.18 | 0.08 |

[a]In 0.01 M HCl pH 2.
[b]In 0.001 M NaOH pH 10.
[c][θ]₂₁₅ (8)/[θ]₂₁₅ (x) refer to "Quantitation of helicity".

Of interest, the CD spectrum for SEQ ID NO: 8 shows a slight shift in its minima to lower wavelengths compared with longer alpha helical peptides (222 nm→215 nm, 208 nm→207 nm), as has been observed before in short fixed nucleus alanine helices[116]. Given that these are the first CD spectra of very short isolated alpha helices, it is not surprising that their CD spectra differ from those of much longer helices. Theoretical studies[117,118] into the chiroptic properties of the alpha helix have predicted that short alpha helices should have different CD spectra from longer alpha helices. The negative minimum at 215 nm is consistent with the long wavelength n→π*transition commonly observed for alpha helices and beta sheets in the 215-230 nm wavelength range.[119] The observed positive maximum at 190 nm and negative minimum at 207 nm characterize the structure as alpha helix rather than beta sheet, as these bands can only arise from exciton splitting of the $NV_1$ transition by the interaction of electric dipole transition moments among amides in the well defined geometry of the alpha helix. The relative intensities of these peaks for SEQ ID NO 8 mirror those observed for other alpha helices, therefore we have quoted the intensities at 190 nm, 207 nm and 215 nm in Table 6.

Helix Dependence on Sequence

Certain residues are known to favor or disfavor alpha helicity, therefore the residues in this system were altered in an attempt to gain insight into the helicity for these cycles. Initial solubility issues with hydrophobic pentapeptides prompted us to incorporate an additional arginine at the N-terminus. Nine K(i)→D(i+4) side-chain cyclised hexapeptides were synthesized with the three residues intervening the bridge systematically replaced by alpha helix inducing (alanine, leucine, methionine, glutamine), alpha helix indifferent (phenylalanine, serine), or alpha helix breaking (glycine) residues (Table 7).

TABLE 7

Molar elipticities ([θ] deg.cm². dmol⁻¹.residue⁻¹) at λ = 215,
207 and 190 nm, ratios of elipticities at 215/207 nm, and
percentage helicity for cyclic peptides 23-31 in 10 mM
phosphate buffer pH 7.4 at 25° C.

| Peptide | $[\theta]_{215}$ | $[\theta]_{297}$ | $[\theta]_{190}$ | $\theta_{215}/\theta_{207}$ | Relative Helicity[a] |
|---|---|---|---|---|---|
| Ac-(cyclo-2,6)-R[KAAAD]-NH₂ [SEQ ID NO: 23] | −13537 | −13684 | 39352 | 0.99 | 0.91 |
| Ac-(cyclo-2,6)-R[KALAD]-NH₂ [SEQ ID NO: 24] | −14798 | −15165 | 46621 | 0.98 | 1.00 |
| Ac-(cyclo-2,6)-R[KAMAD]-NH₂ [SEQ ID NO: 25] | −11853 | −12296 | 38464 | 0.96 | 0.80 |

TABLE 7-continued

Molar elipticities ([θ] deg.cm².dmol⁻¹.residue⁻¹) at λ = 215, 207 and 190 nm, ratios of elipticities at 215/207 nm, and percentage helicity for cyclic peptides 23-31 in 10 mM phosphate buffer pH 7.4 at 25° C.

| Peptide | $[\theta]_{215}$ | $[\theta]_{297}$ | $[\theta]_{190}$ | $\theta_{215}/\theta_{207}$ | Relative Helicity[a] |
|---|---|---|---|---|---|
| Ac-(cyclo-2,6)-R[KAQAD]-NH₂ [SEQ ID NO: 26] | −11394 | −12279 | 36865 | 0.93 | 0.84 |
| Ac-(cyclo-2,6)-R[KAFAD]-NH² [SEQ ID NO: 27] | −8644 | −9087 | 27718 | 0.95 | 0.76 |
| Ac-(cyclo-2,6)-R[KAGAD]-NH₂ [SEQ ID NO: 28] | −4874 | −7678 | 10036 | 0.63 | 0.32 |
| Ac-(cyclo-2,6)-R[KGSAD]-NH₂ [SEQ ID NO: 29] | −4810 | −6975 | 12831 | 0.69 | 0.32 |
| Ac-(cyclo-2,6)-R[KSSSD]-NH₂ [SEQ ID NO: 30] | −4432 | −8017 | 6827 | 0.55 | 0.30 |
| Ac-(cyclo-2,6)-R[KGGGD]-NH₂ [SEQ ID NO: 31] | −2131 | −4868 | −1593 | 0.44 | 0.14 |

[a] $\theta_{215}$ [SEQ ID NO: 24]/$\theta_{215}$ (x) refer to "Quantitation of helicity" section below.

Figure 2:
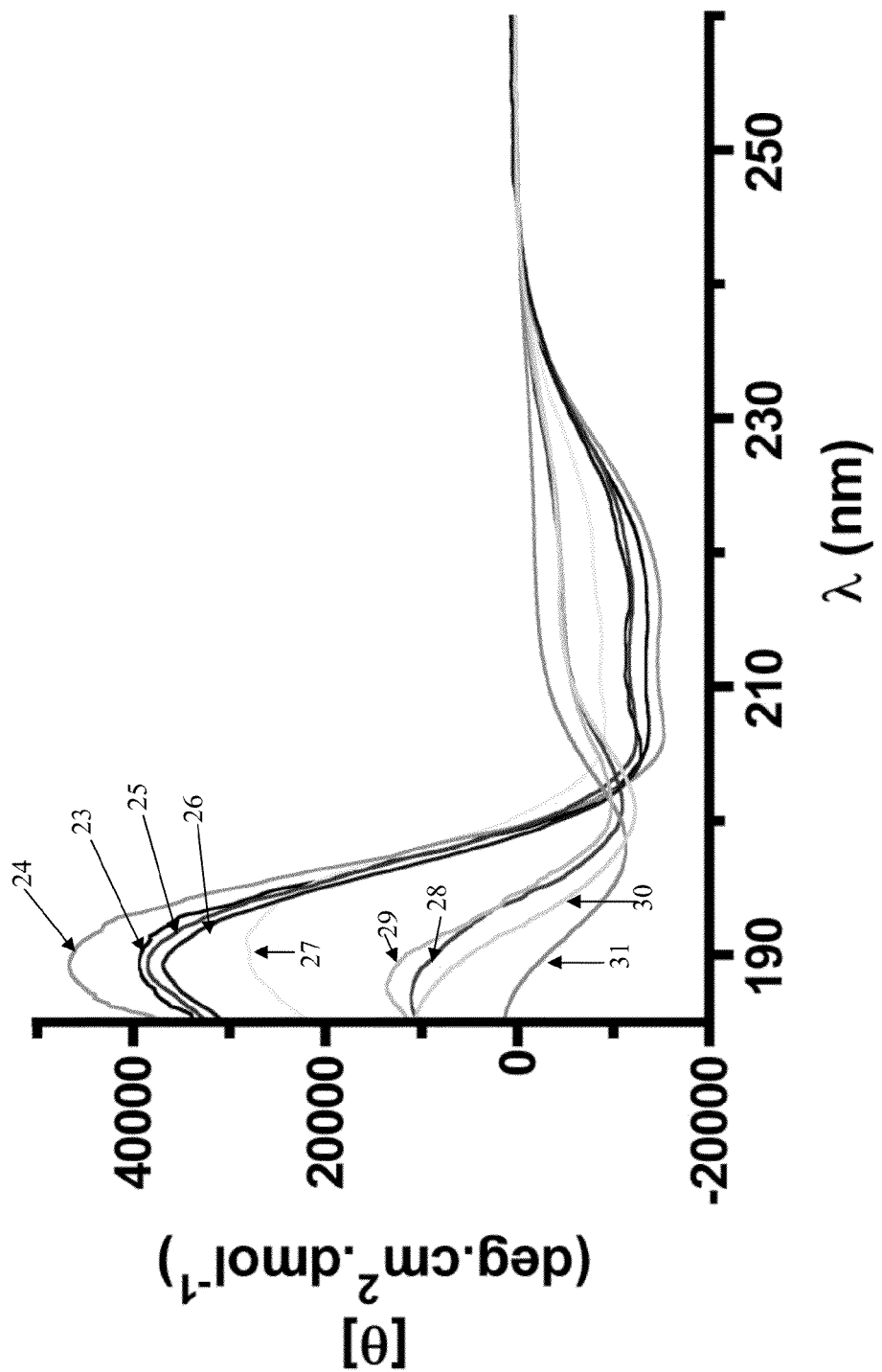
FIG. 2 depicts CD spectra of compounds SEQ ID NOS: 23, 24, 25, 26, 27, 28, 29, 30 and 31 in 10 mM phosphate buffer (pH 7.4, 25° C.) demonstrating the variation of helicity by varying the residues within the lactam cycle.

FIG. 2 shows that helicity is dependent on which residues intervene between the PGP-45.DNA bridging residues. The helical structure is tolerant of substitution by alpha helix inducing residues like Ala ([SEQ ID NO: 23], Leu [SEQ ID NO: 24], Met [SEQ ID NO: 25], Gln [SEQ ID NO: 26] and Phe [SEQ ID NO: 27], as demonstrated by the deep minima at 215/207 nm, high maximum at 190 nm, and high ratio $\theta_{215}/\theta_{207}$. There is some variation in the intensity at these wavelengths which closely mirrors the intrinsic alpha helical propensity of specific amino acids determined in protein environments[35]. The system can be perturbed by replacing the central residue with glycine [SEQ ID NO: 28], which results in a decrease in intensity at 215 nm, 207 nm and 190 nm, along with the appearance of a deeper minimum at 201 nm that is commonly observed for 3₁₀-helicity/random coil structures. This reduction in alpha helicity also results from placement of two [SEQ ID NO: 29] or three [SEQ ID NO: 30] helix disfavoring residues between the bridging residues, although based on the shape of their CD spectra there is some bias towards a helical conformation. Not surprisingly, where three alpha helix breaking residues are present [SEQ ID NO: 31], total abolition of helicity was indicated by the single deep minimum at 200 nm characteristic of a random coil.

NMR Evidence for Alpha Helicity

Structural characterization was conducted for SEQ ID NO. 8 and SEQ ID NO 23 using 1D and 2D ¹H-NMR spectroscopy in 90% H₂O: 10% D₂O at 288 K (pH 4.0). 2D-TOCSY spectra at 600 MHz were used to identify resonances for each amino acid. Due to the molecular weight of the macrocycle, ROESY instead of NOESY spectra had to be used to identify sequential connectivity and intra-residue NH—NH and NH—CH cross peaks Spectral overlap in SEQ ID NO. 8 prevented unambiguous identification of key long range ROEs, however SEQ ID NO. 23 gave well defined resonances and was investigated further. There were a number of spectral features that are characteristic of well-defined structure in the cyclic hexapeptide [SEQ ID NO: 23], and specifically characteristic of alpha helicity.

First, there were conspicuously low coupling constants ($^3J_{NHCH\alpha}$<6 Hz) for all amide resonances except D6, as normally observed in alpha helical peptides. Second, all of the residues displayed a upfield shift (0.18 to 0.32 ppm) for δ(Hα) relative to the corresponding residue in random coil structures, this also being typical of helical peptides. Third, there was a low temperature dependence for amide NH chemical shifts, with temperature coefficients (Δδ/T) being ≤4 ppb/K for Ala3, Ala4, Ala5, Asp6, and one C-terminal amide NH (FIG. S5, Supporting Information), consistent with their involvement in hydrogen bonds that characterise an alpha helix. Fourthly, the observation in ROESY spectra of non sequential medium range $d_{\alpha N}$ (i,i+4), $d_{\alpha N}$(i,i+3), $d_{\alpha\beta}$(i, i+3) ROEs (FIG. 4) suggest helical structure, and the particularly prominent $d_{\alpha N}$(i,i+4) versus weak $df_{\alpha N}$ (i,i+2) ROEs supports a high proportion of alpha helicity rather than 3₁₀-helicity or turn conformations.

Solution Structure of 23

Figure 3:
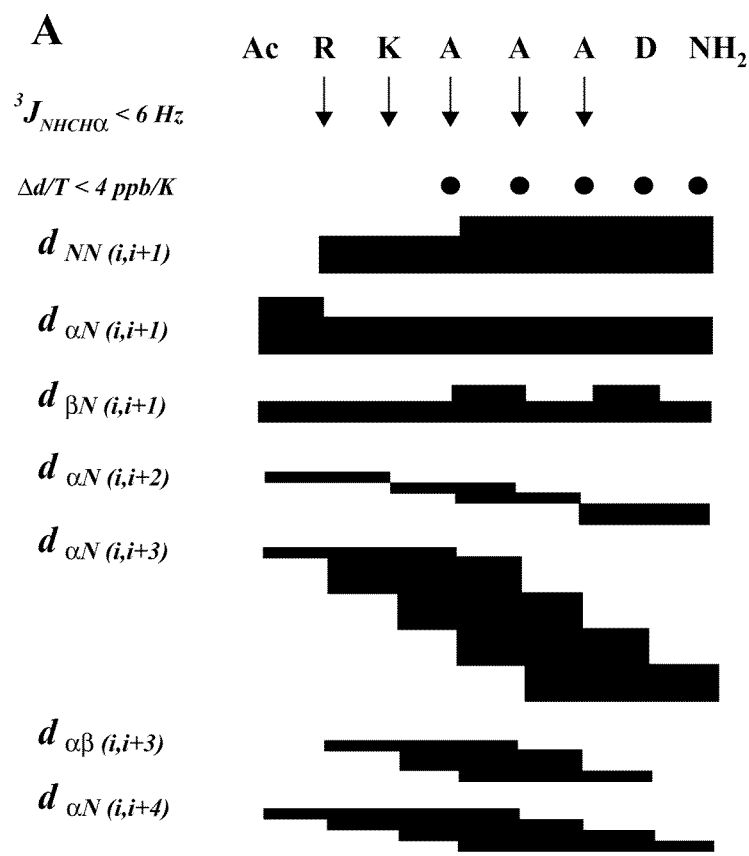
FIG. 3A depicts a ROE Summary Diagram (left) and 20 lowest energy calculated structures for Ac—(cyclo-2,6)—R[KAAAD]—NH$_2$ (23) in 90% H$_2$O: 10% D$_2$O at 20° C. Thickness of bars reflects intensity of ROEs.
FIG. 3B depicts a lactam bridge.
Figure 3:
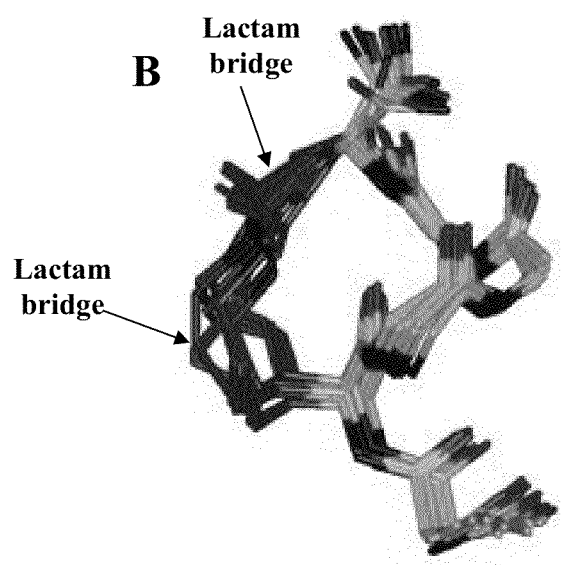

The three dimensional structure for the hexapeptide 23 in 90% H₂O: 10% D₂O at 20° C. was calculated using dynamic simulated annealing and energy minimization in Xplor (3.851) from 81 ROE (26 sequential, 25 medium range, 30 intra-residue) distance restraints, and 4 phi angle restraints ($^3J_{NHCH\alpha}$<6 Hzφ=−65±30°). No explicit Hbond restraints were included in calculations. The final 16 lowest energy structures contained no dihedral angle (>2°) or distance (>0.1 Å) violations and are displayed in FIG. 3. These lowest energy structures indicate a well defined alpha turn, with four i→i+4 hydrogen bonds involving NH protons of the C-terminal amide, Asp6, Ala5, Ala4 and the CO oxygens of Ala3, Lys2, Argi and N-terminal amide. The backbone pairwise RMSD for this family of structures for Ac—(cyclo-2,6)—R [KAAAD]—NH₂ (23) in water is 0.35 Å, indicating a fairly tight structural convergence. When 23 was superimposed on an idealized textbook hexapeptide alpha helix (i.e. backbone dihedral angles set wψ=−47°, φ=−57°), the backbone pairwise RMSD=0.81 Å. However, for just the cyclic pentapeptide component of 23, the backbone pairwise RMSD=0.22 Å over backbone carbon and nitrogen atoms. This structural evidence strongly supports the conclusion that the endocyclic residues are in a highly alpha helical conformation, more so than the exocyclic Arg residue.

Effect of a Helix Stabilizing Solvent

Figure 4:
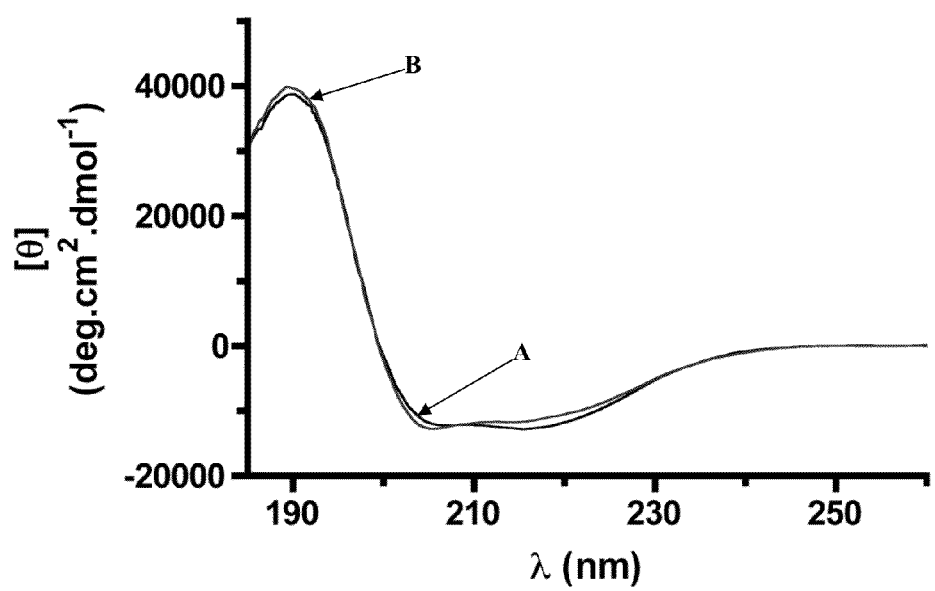
FIG. 4 depicts CD spectra of 8 in 10 mM phosphate buffer (A) (pH 7.4, 25° C.) and 50% TFE (B).

To see whether the alpha helicity exhibited by 8 in water could be increased, a CD spectrum was acquired for 8 in 50% aqueous TFE (a helix-inducing solvent which increases helicity for peptides). FIG. 4 shows that the presence of 50% TFE does not increase molar elipticity at 215 nm, suggesting that 8 is already maximally alpha helical in water alone. This optimum alpha helicity is also supported by the ratio $\theta_{215}/\theta_{207} > 1$ in water alone, as reported for an idealized (100%) alpha helix[120]. Although there is some controversy regarding the accuracy of this ratio[121], in this case it is at least still indicative of substantial alpha helicity.

Helix Dependence on Hydrogen Bonds

Figure 1B:
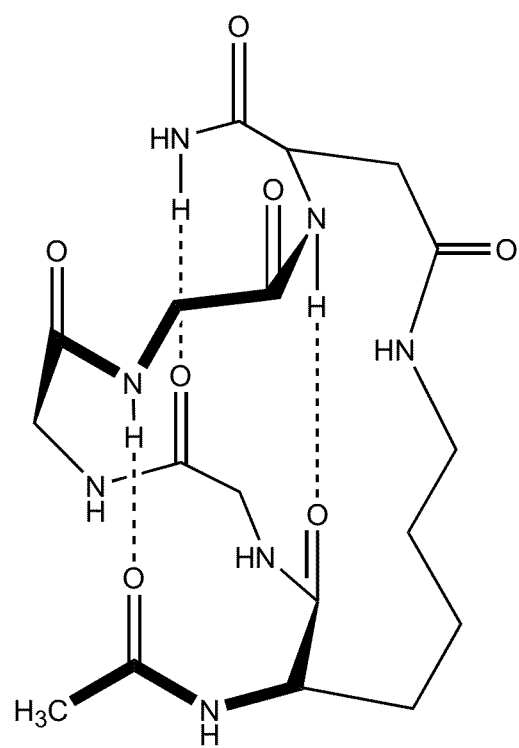
FIG. 1B depicts a schematic demonstrating the positions of the three hydrogen bonds (dotted lines) important for stabilization of the pentapeptide helix.

The NMR analysis indicated the presence of 3 hydrogen bonds within the pentapeptide cycle. To investigate the importance of these hydrogen bonds for the conformational stability of 8, we synthesized a series of analogues with variable potential for forming intramolecular hydrogen bonds. Since 1,5-hydrogen bonds are characteristic of alpha helicity, inclusion or exclusion of the N-terminal acetyl group or the C-terminal amide group allowed variation between 1-3 potential hydrogen bonds (FIG. 1). Thus Ac—(cyclo-1,5)-[KARAD]—NH$_2$ (8) can form 3 potential intramolecular 1,5-hydrogen bonds (FIG. 1), while Ac—(cyclo-1,5)-[KARAD]-OH (20) and H-(cyclo-1,5)-[KARAD]—NH$_2$ (21) can form only two hydrogen bonds, and H-(cyclo-1,5)-[KARAD]-OH (22) can only form 1 hydrogen bond.

Of this group of four peptides, only 8 showed alpha helical structure in water at pH 7 (see Table 6), indicating that a minimum of 3 hydrogen bonds is required for alpha helicity in a pentapeptide sequence (see FIG. 1). Since the effect of charges at the N- and C-termini might be expected to destabilize helicity, CD spectra were also recorded for 20 and 21 in 0.01M HCl (pH 2) and 0.001M NaOH (pH 11), ensuring that the uncapped termini were fully protonated and deprotonated respectively. The pH had little effect on conformation, both 20 and 21 showed slight increases in helicity, but remained largely unstructured. Compound 22 was not examined at high or low pH as one of the termini will always be charged.

Quantitation of Helicity

Assuming that mean alpha helix content ($f_H$) is linearly related to elipticity at 222 nm, or in our case 215 nm ($[\theta]_{obs215}$), then the equation for calculating helix content is:

$$f_H = ([\theta]_{obs215} - [\theta]_C)/([\theta]_{\infty 215} - [\theta]_C) \quad (1)$$

Luo and Baldwin[22] determined that the random coil ($[\theta]_C$) and infinite alpha helix ($[\theta]_{\infty 222}$) molar elipticities are temperature dependent based on the equations:

$$[\theta]_C = 2220 - 53T \quad (2a)$$

$$[\theta]_{\infty 215} = (-44000 + 250T)(1 - k/N_p) \quad (2b)$$

where T is temperature in degrees Celsius, $N_p$ is the number of peptide units, and k is a finite length correction.

Despite the widespread use of equation 1, a key problem is the implementation of a suitable k factor for which a range of values between 2.4-4.5 have been used[121]. Baldwin has suggested using k=3.0 for carboxyamidated peptides and 4.0 for unblocked peptides[123]. For 8, variation of the k factor from 2.4 to 4.5 resulted in 56-135% helicity, so it was clear that the k factor can impact significantly on reported values of alpha helical content. There is no empirical method to determine a suitable k factor, and the problem of choosing one becomes particularly acute for short peptides. Given our compelling high resolution NMR data and CD studies in the presence of benign, helix stabilizing, and helix destabilizing environments, we believe it is highly likely that the equilibrium between random coil, partial helix and pure alpha helix is shifted significantly towards pure alpha helix such that $f_H$ is ~1 and the contribution of $[\theta]_C$ is ~0. Based on the assumption that 8 has 100% α-helicity, we can derive k~4, which is within the suggested range. If we apply this value to equation 2b then the percentage helicities for the alpha helical compounds in tables 6 and 7 are 100% (8), 83% (23), 91% (24), 73% (25), 70% (26), 53% (27).

There are however, problems associated with this derivation. Firstly, despite the significance of the Luo-Baldwin study, it does not reflect the properties of very short peptides. Secondly it is based on extrapolating TFE titration data to CD data acquired in water alone[21]. Thirdly, their study is calibrated to elipticity at 222 nm, whereas the absolute minimum in these peptides occurs at 215 nm. Given these difficulties, we have expressed relative rather than absolute helicities for the peptides in Tables 6 and 7.

The implication of these results are that appreciable alpha helicity (50-100%) can be achieved in cyclic pentapeptides using systems like for example, SEQ ID NO: 8.

Twenty membered macrocycles related to that in SEQ ID NO: 8, with the same ring size and same positioned amide linker but with different intervening amino acids between K and D at positions i+1, i+2, and i+3 were also examined [SEQ ID NOs: 14 to 17 and 23 to 31]. An arginine was also tacked onto the N-terminus to promote aqueous solubility but would not be expected to affect rank orders of helicity in the following compounds. The rank order for decreasing alpha-helicity in these 20-membered cyclic pentapeptides was SEQ ID NOs: 24>23>26>25>27>28=29>30>31. Peptides having SEQ ID NOs: 30 and 31 have three of the same amino acids between linking amino acids, namely Serine or Glycine, and such amino acids are known in proteins to be the least favorable to helix formation. In fact Serine is often termed a helix breaker and Glycine is often thought of as a beta/gamma turn inducer. The peptide having SEQ ID NO: 29 suggests that even with two of these amino acids present, the cyclic pentapapetide can still have appreciable alpha helicity.

CD Spectra for SEQ ID NOs: 8 to 13, 18 and 19 and SEQ ID NOs: 23 to 31 can be found in FIGS. 1 and 2, respectively.

Discussion of Example 9

Herein the present inventors have disclosed the first 5-residue peptides that display essentially complete alpha helicity in water, making them the shortest and most stable peptide alpha helices known. This result, confirmed by NMR-derived structure determination in water, was unique for pentapeptides cyclized through amide formation specifically between Lysine and Aspartate at positions i and i+4 respectively. Their alpha helical nature has been convincingly established by circular dichroism and $^1$H-NMR spectra, neither of which were concentration dependent, thus ruling out alpha helicity due to aggregation. Failure to enhance alpha helicity (especially of 8) using 50% TFE, failure to diminish it with 8M guanidine.HCl, and lack of success in degrading it with proteolytic enzymes, supports our conclusion of an exceptionally high proportion of alpha helical conformers in the structural ensemble, especially for compound 8.

Conventional head to tail cyclic pentapeptides are traditionally associated with various types of β and gamma turn conformations in solution, although in water they tend to display no well defined structure at all. In the literature of peptide hormones there is evidence that lactam bridges, particularly (i, i+4) linkages, can increase helicity in longer peptides and enhance bioactivity. However there is considerable disparity in the alpha helix stabilizing effects of various lactam bridges, with little agreement about which sequences, ring sizes, and ring compositions impart the highest alpha helicity[43], and suggestions that effectiveness is case dependent[50]. Here, the inventors have systematically examined the effects of different lactam bridges on alpha helix stability in simple pentapeptides, cyclized through side chain to side chain coupling. They have shown that cyclic pentapeptides of defined size (20-membered rings) and specific composition have the capacity to adopt a single alpha turn conformation that is remarkably stable in water. Spectral data from circular dichroism and 2D $^1$H NMR strongly support alpha helicity for such cycles in water, even under severe peptide-denaturing conditions such as high concentrations of guanidine hydrochloride (<8 M). These results also demonstrate that a single lactam bridge can effectively stabilize alpha helicity in short peptides, which contrasts with the best results to date where two overlapping lactam bridges were required to necessitate alpha helix stabilization in short peptides[49,124].

A feature of this work is the finding that appreciable alpha helicity is dependent not only on the cyclic constraint that produces a 20-membered ring, but also on accompanying formation of three intramolecular 13-membered hydrogen bonded rings. Thus three i→i+4 hydrogen bonds together with the cyclic constraint would appear to be the minimum requirements to stabilize an alpha turn, since either removal of just one of these hydrogen bonds or minor modification to the cyclic restraint was sufficient to collapse the alpha helical structure. It is worth pointing out that, for a conventional uncapped peptide, three 1→5 hydrogen bonds would require a minimum sequence of seven amino acids. In the absence of the thermodynamic stability afforded by the cyclic constraint, it is therefore now explicable as to why acyclic peptides can only be highly alpha helical if they are much longer.

The significant difference observed in the RMSD values between the alpha helical hexapeptide structure 8 and its cyclic pentapeptide structural component is consistent with the need for the cyclization restraint, rather than just 3 (or 4) hydrogen bonds, for alpha helicity. Although NMR data at low temperature did indicate that the exocyclic Arg residue in 8 was in an alpha helical environment created by 4 hydrogen bonds and the cyclization constraint, the deviation from an idealized alpha helix was larger for the hexapeptide over the pentapeptide, reflecting less alpha helicity for this residue which is outside the cycle. This does not necessarily mean that the cyclic pentapeptide cannot transmit alpha helicity to multiple attached exocyclic residues, only that it isn't very effective in inducing helicity in a single attached residue. This slight fall off in helical integrity outside the cycle is not too surprising, since the termini of protein/peptide alpha helices are normally quite disordered in solution structures, and certainly more disordered than found for the ends of 8.

The helix stability is dependent upon sequence, according to normal rules of protein-based structure e.g., those residues known to favor alpha helicity in proteins also favor alpha helicity in these cyclic pentapeptides. However unlike proteins, these simple systems are not complicated by effects of side chain packing, folding, intra- or inter-molecular interactions other than with solvent, and thus would appear to offer excellent opportunities to investigate effects of individual natural or unnatural amino acid components on the alpha helix. Since the cycles remained intact under peptide-denaturing conditions, they may be useful as templates in longer peptides for studying unfolding/refolding and for 'seeding' structure in proteins and polypeptides. The stability of the cycles under peptide-degrading conditions (trypsin, human serum) also suggests that they may have useful alpha helix-mimicking properties in biologically relevant environments.

In another context the observations here complete the picture for cyclic peptides as mimetics of the key elements of protein structure. While i→i+4 side chain to side chain cyclization herein has produced a stable alpha turn with a 13-membered hydrogen bonded ring in pentapeptides, i→i+3 side chain to side chain cyclization is known to produce the beta turn with a 10-membered hydrogen bonded ring (multiples of which constitute the $3_{10}$— helix) in tetrapeptides, and i→i+2 side chain to side chain cyclization has produced the gamma turn involving a 7-membered hydrogen bonded ring as well as the beta strand, depending upon the constraints in the cycle, in tripeptides. Clearly cyclization, together with appropriate use of molecular constraints in peptide sequences, can be systematically and effectively used to mimic any of the fundamental structural elements of proteins.

In summary, the high conformational and proteolytic stability of these alpha helical cyclic pentapeptides suggests their use as single turn alpha helical modules, with capacity for decoration by peptidic, cyclic, or non-peptidic appendages, to mimic bioactive peptide or protein alpha helical segments.

Example 10

Stability

Stability Against Denaturants

Figure 5:
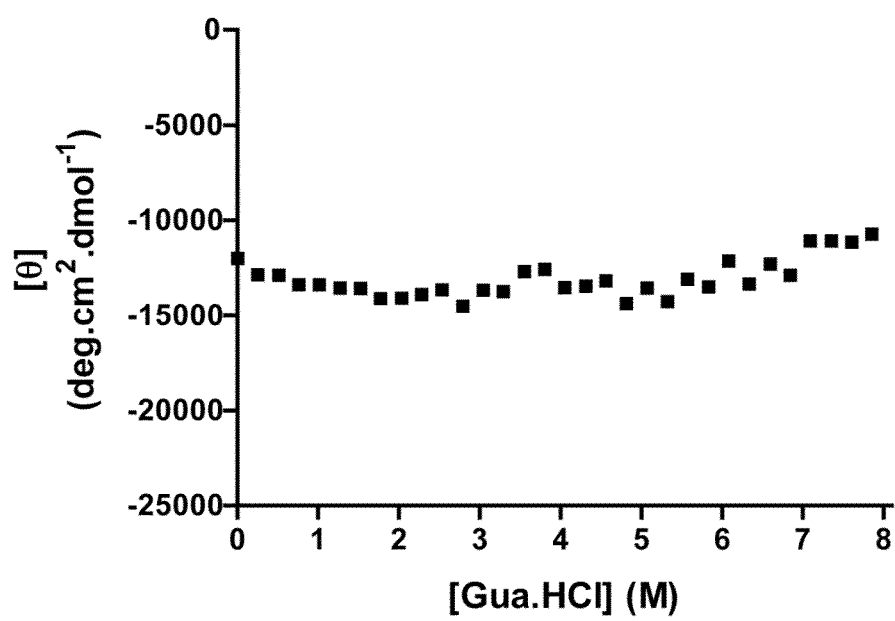
FIG. 5 is a graphical representation showing the variation in molar elipticity of 8 at 215 nm with increasing [guanidine-.HCl] at 25° C.

Using the molar elipticity at 215 nm as an indicator of alpha helicity, FIG. 5 clearly shows that SEQ ID NO: 8 is conformationally stable, the pentapeptide maintains full alpha helicity even in the presence of 8M guanidinium chloride. These conditions readily denature peptides and proteins, but do not affect alpha helicity in 8. Proteolytic stability of the helix. trypsin digestion A standard solution of Ac—KARAD-NH$_2$ and Ac—(cyclo-1,5)-KARAD-NH$_2$ (1 mg/mL) was prepared in 100 mM ammonium carbonate buffer at pH~8.2. To 100 μL of each solution was added 1 mg/mL of trypsin (1 μL). The digest was conducted at room temperature with 5 μL aliquots taken at 1, 4, 8, 28, 48, 55, 110, 155 minutes. Aliquots were diluted with 5 μL of 3% TFA to stop the reaction. and analyzed by LC-MS using 2.1×150 mm Phenomenex 300 Å C18 5 μm column, with a 3% per minute linear gradient of 0-60% acetonitrile over 20 minutes. The amount of starting material left in each sample was quantified by determination of total ion counts for the molecular ion.

Compound of SEQ ID NO 8 and its acyclic version SEQ ID NO: 14 were incubated with trypsin (pH 8.2), aliquots removed at intervals between 1 and 155 minutes, and analyzed by LCMS. The cyclic compound remained intact over this period, whereas the acyclic analogue completely hydrolyzed within a few minutes to fragments Ac—KAR-OH, H-ARAD-NH$_2$, H-AR-OH and H-AD-NH$_2$. Similarly the cyclic compound 8 was not degraded by human serum (1 h, 37° C.). These results prove that the peptide sequence in 8, being held in an alpha helical conformation, is not susceptible to recognition by the proteolytic enzyme. This is consistent with other observations that only an extended or linear peptide conformation is recognized, not only by trypsin, but by all proteolytic enzymes[125] Presumably the cycle is too tightly locked into an alpha helical turn to permit significant unwinding to the extended format needed for recognition by trypsin.

Serum Stability

Standard solutions of Ac—KARAD-NH$_2$ and Ac—(cyclo-1,5)-KARAD-NH$_2$ (1 mg/mL) were prepared in water. 200 µL of each peptide was added to human serum 800 µL and incubated at 37° C. Acetonitrile/water 3:1 (300 µL) was added to aliquots (100 µL) of serum at 5, 15, 30, 45 and 60 minutes to precipitate serum proteins, which were removed by centrifugation. The decanted supernatant was analyzed by LC-MS MS with a 2.1×150 mm Phenomenex 300 Å C18 5 um column, using a 3% per minute linear gradient from 0%-60% acetonitrile over 20 minutes. The amount of starting material left in each sample was quantified by determination of total ion counts for the molecular ion.

Example 11

CD Spectra on Peptides Having One or More Cyclic Pentapeptide Modules

CD was performed on peptides having one [SEQ ID NO: 8] or more than one modular macrocycle [SEQ ID NOs: 46 and 47], as compared with corresponding linear peptides, Ac[KARAD]$_n$—NH$_2$ where n=1 [SEQ ID NO: 14], n=2 [SEQ ID NO: 54] and n=3 [SEQ ID NO: 55]. The molar elipticities at 222 nm, 208 nm and 190 nm, ratios of elipticities at 222 nm/208 nm and percentage helicity are shown in Table 8.

TABLE 8

| Peptide | [θ]$_{222}$ | [θ]$_{208}$ | [θ]$_{192}$ | θ$_{222}$/θ$_{208}$ | % helicity* |
|---|---|---|---|---|---|
| SEQ ID NO: 8 | −15464 | −17039 | 52191 | 0.98 | 79 |
| SEQ ID NO: 46 | −32340 | −24957 | 104187 | 1.29 | 99 |
| SEQ ID NO: 47 | −31987 | −23842 | 100811 | 1.34 | 88 |
| SEQ ID NO: 14 | −732 | −5758 | −14779 | 0.12 | 0.8 |
| SEQ ID NO: 54 | −1836 | −8552 | −12237 | 0.21 | 3 |
| SEQ ID NO: 55 | −3852 | −9788 | −8024 | 0.39 | 7 |

*% = f$_H$ × 100,
[θ$_{∞H}$]$_{222}$ = −44000 degcm$^2$dmol$^{-1}$residue$^{-1}$ [86],
k = 2.6[85].

Figure 6:
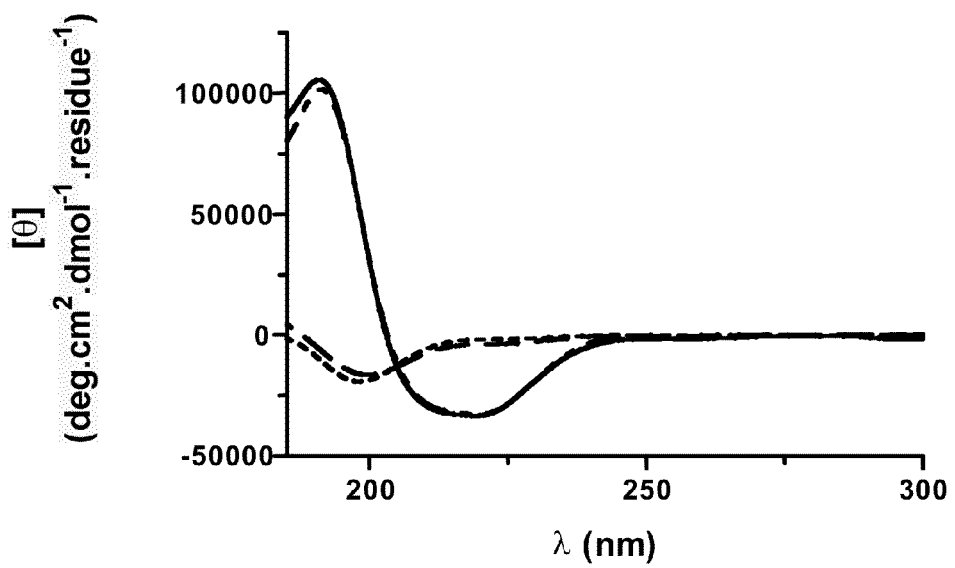
FIG. 6 depicts a CD spectrum comparing the helicity of SEQ ID NOs: 46 and 47 with their acyclic linear analogues SEQ ID NOs: 54 and 55.

A CD Spectrum comparing the helicity of SEQ ID NOs: 46 and 47 with their acyclic linear analogues SEQ ID NOs: 54 and 55 is shown in FIG. 6.

Example 12

Figure 7:
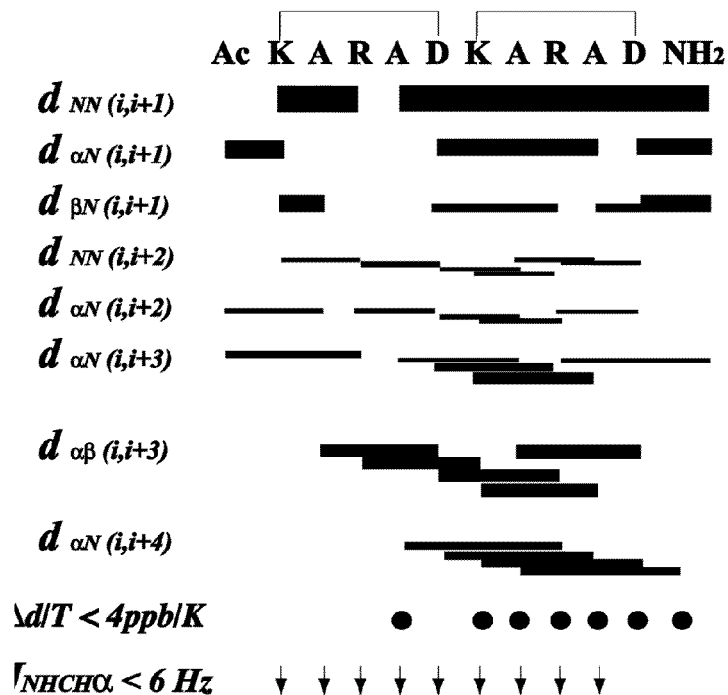
FIG. 7 depicts the sequential and medium ROEs, temperature coefficients, and coupling constants for SEQ ID NO: 46 in 90% H$_2$O: 10% D$_2$O.

To confirm this compelling CD evidence of high alpha helical structure, we have also examined NMR spectra for pentapeptide SEQ ID NO:46 in 90% H$_2$O: 10% D$_2$O. We identified multiple spectral features (FIG. 7) characteristic of alpha helicity including: (i) upfield CHα chemical shifts;[109] (ii) coupling constants $^3J_{NHCH}$≤6 Hz[110] for all amide NHs (2.2-5.2 Hz) except D$_{10}$; (iii) low temperature dependence of chemical shifts (Δ/T≤4 ppb/deg) for 7 amide NHs,[111] consistent with all expected helix-defining H-bonds except for K$_1$→D$_5$; and (iv) non-sequential medium range ROEs d$_{αN}$(i, i+3), d$_{αN}$ (i, i+4) and d$_{αβ}$(i, i+3) in ROESY spectra.[100] In particular the high intensity d$_{αN}$(i, i+4) and very weak d$_{αN}$(i, i+2) ROEs are striking, indicating a lack of substantial contributions from beta or gamma turns to the conformational mix and establishing alpha rather than 3$_{10}$-helicity.

Figure 8:
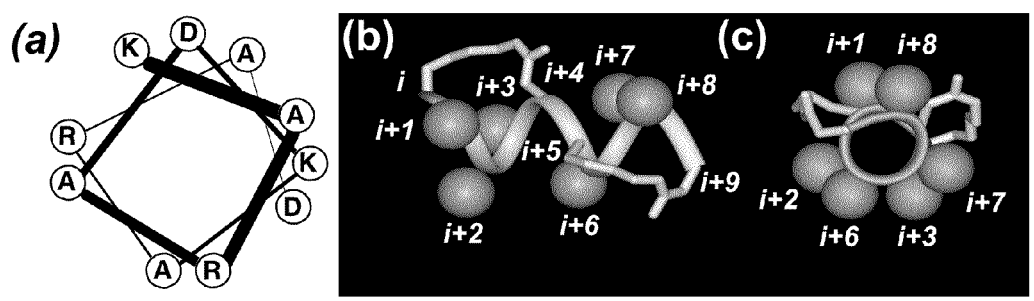

Three dimensional structures were calculated for SEQ ID NO: 46 in water, initially using torsional angle dynamic simulated annealing in DYANA[112], followed by dynamic simulated annealing and energy minimization in Xplor (3.851)[113] from 89 ROE (24 sequential, 38 medium range, 27 intra-residue) distance restraints, 9 phi angle restraints ($^3J_{NHCHα}$, φ−65±30°) and 2 chi1 angle restraints ($^3J_{NHCHα}$, χ$_1$−60±30°). No explicit H-bond restraints were included in calculations. Final structures indicate 3 well-defined alpha helical turns for SEQ ID NO: 46 in water, with lactam bridges in the locations anticipated from FIG. 8.

Figure 9:
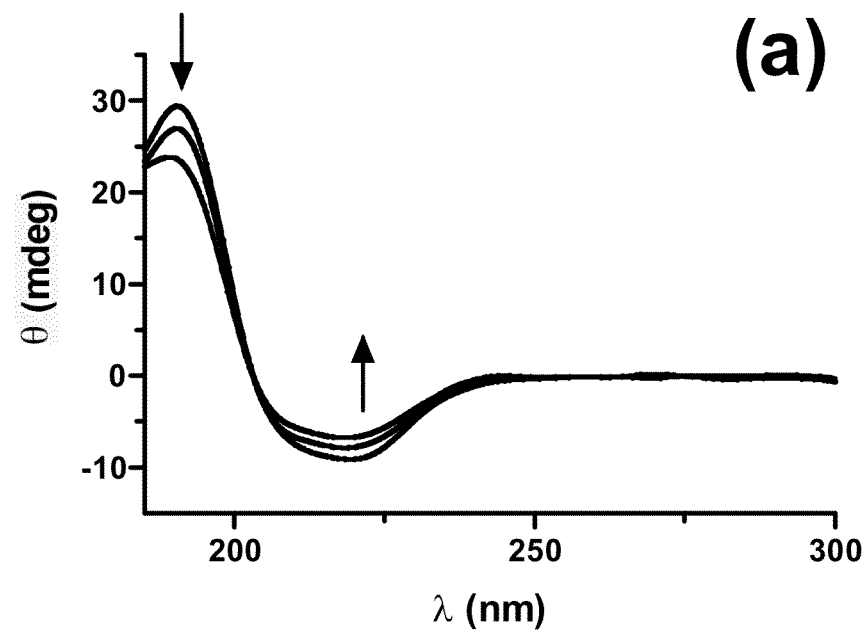
FIG. 9 depicts CD spectra in 10 mM phosphate buffer, pH 7.4, 25° C. for 32-44 mM solutions of (a) SEQ ID NO: 46 (—), SEQ ID NO: 47 (— - —) and acyclic analogues SEQ ID NO: 54 (— —) and SEQ ID NO: 55 (- - -); (b) SEQ ID NO: 46 (—) versus SEQ ID NO: 47 (- - -), SEQ ID NO: 54 (— —) and SEQ ID NO: 55 (— - —) in 50% TFE.
Figure 9:
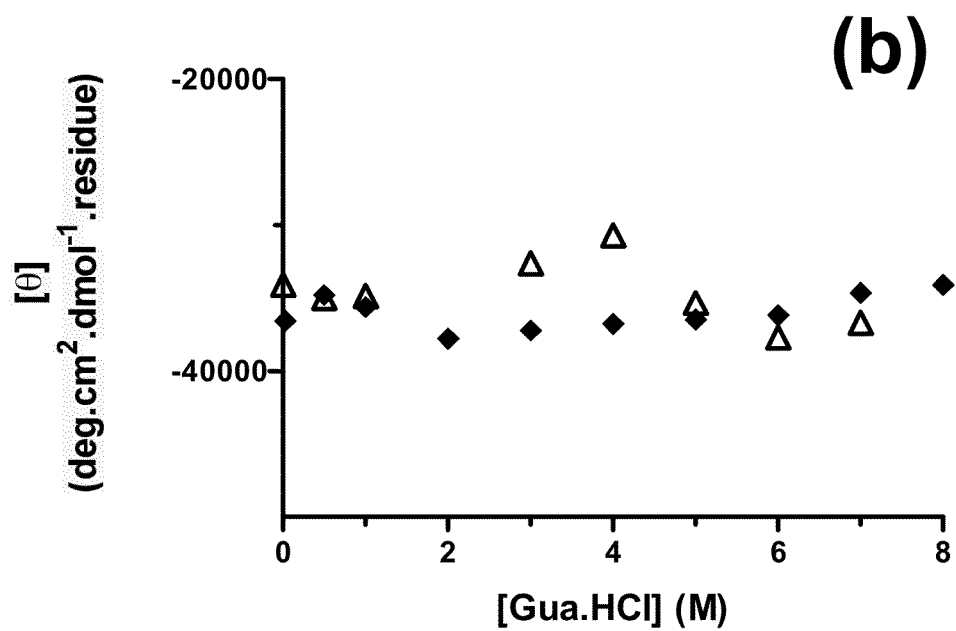

The helical macrocycles were conformationally very stable even under protein-denaturing conditions, as illustrated by the low dependence of their CD spectra on temperature between 5-65° C. (FIG. 9a) and on the concentration of guanidine.HCl (FIG. 9b).

In summary, 10- and 15-residue peptides were engineered to form 3 and 4 consecutive alpha helical turns via 2 and 3 macrocycles shown to maintain high conformational stability in water even under strong protein-denaturing conditions. CD and 2D-NMR spectra provide compelling evidence of alpha helicity that could not be increased by adding TFE. Assembly of consecutive cyclic pentapeptide modules appears to be a suitable strategy for general mimicry of small alpha helical protein segments that bind receptors/ligands on one helical face. Their high conformational and proteolytic stability bring enormous advantages over linear peptides, and suggest potential uses as biological probes and drug leads.

Example 13

Trypsin Digest

Solutions of SEQ ID NO: 46 (25 µM) and linear peptide SEQ ID NO: 54 (26 µM) were incubated with trypsin (1 µg/mL) in 25 mM ammonium carbonate buffer (pH=8) at room temperature. Aliquots were taken at 30 seconds, 1 minute, 5 minutes, 15 minutes, 30 minutes, 1 hour and 2 hours, and diluted with an equivalent volume of 3% trifluoroacetic acid. The resultant solutions were analyzed using a 2×75 mm, 3 µm, Aqua C-18 column (Phenomenex) equilibrated in aqueous formic acid (0.1%). Peptide cleavage products were eluted using a linear gradient of acetonitrile from 0 to 80% in aqueous 0.01% formic acid over 20 minutes at a rate of 300 µL/min. Rate of degradation of either SEQ ID NO: 32 or SEQ ID NO: 43 was quantified by determining extracted ion counts of chromatograms relative to control solutions (containing no enzyme) using a QSTAR PULSAR Electrospray QqTOF Mass Spectrometer and analyzed using Bio-Multiview (SCIEX Software). Retention time of SEQ ID NO: 46=11.64 minutes. Retention time of linear peptide SEQ ID NO: 54=7.43 minutes. SEQ ID NO: 46 was also found to be highly resistant to proteolytic cleavage by trypsin (97% recovered intact after 2 h), whereas the linear peptide Ac—KARADKARAD-NH$_2$ (SEQ ID NO: 54) was completely degraded within 30 seconds.

Example 14

Helix Mimetics as Anticancer Agents

BH3 Domain Mimetics

Background

Figure 10:
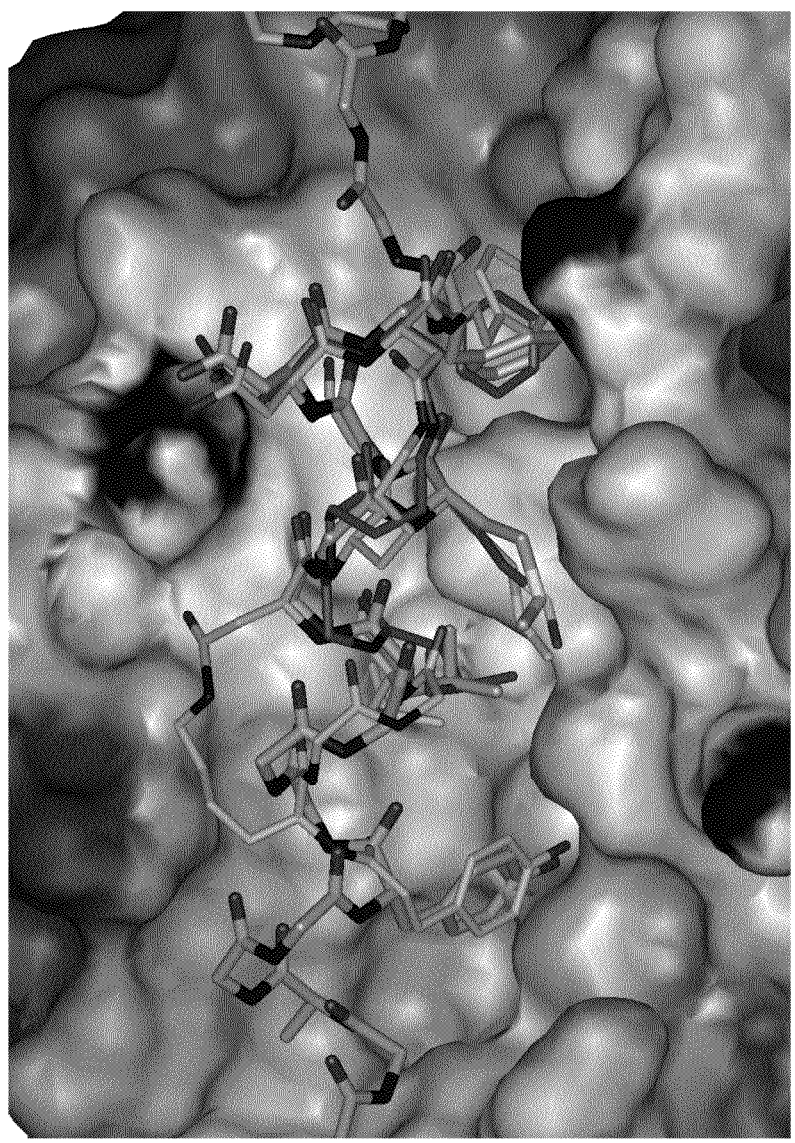
FIG. 10 is a illustration of the crystal structure of Bad (grey) bound to Bcl-X$_L$ protein, NMR structures of monocycle (purple) and bicycle (green) overlay closely with the Bad helix and can display the side chains required for binding in the correct position. (PDBID: 1g5j)
Figure 11:
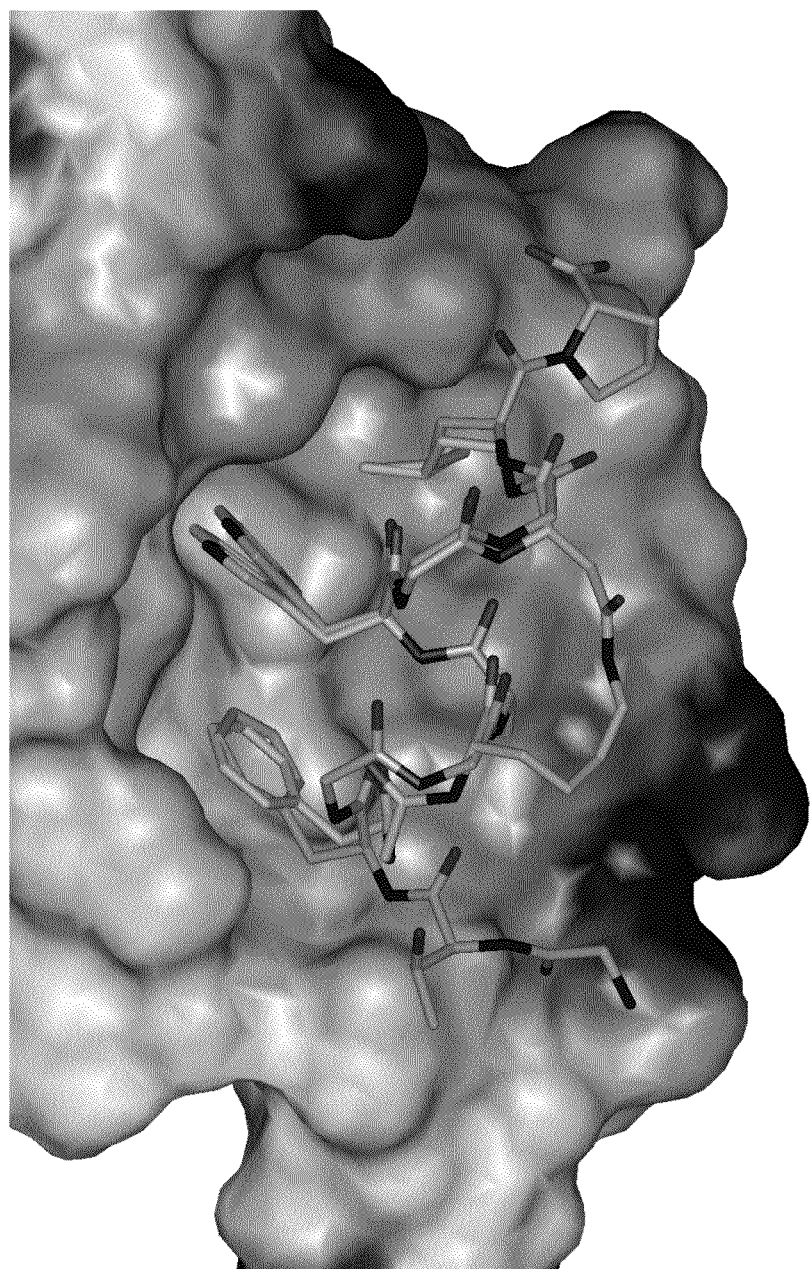
FIG. 11 is an illustration of the crystal structure of p53 (grey) bound to MDM2 oncoprotein (PDBID: 1ycq), with monocycle (Ac—R[KAAAD]—NH$_2$ [SEQ ID NO: 23]) overlayed showing it can position the binding residues in the required position

Apoptosis, the process by which unwanted or damaged cells are removed during development and tissue homeostasis, has been implicated in several malignancies. The Bcl-2 family of proteins contains of several homologues that can display either pro-(Bad, Bak, Bid, Bim, Bax) or anti-(Bcl-2, Bcl-xL, Bcl-W) apoptotic activity. In the case of malignancies, anti apoptotic members of the Bcl-2 family are usually up-regulated resulting in the survival of cancer cells, therefore synthetic inhibitors and anti-apoptotic members are attractive chemotherapeutic agents[126]. The crystal/NMR structures of Bad-Bcl-xL (1g5j)[128], Bak-Bcl-xL (1bx1)[127], and Bim-Bcl-xL (1pq1)[129] demonstrate that pro-apoptotic members interact with Bcl-xL via and alpha helix (as indicated in FIG. 10).

Strategy

The BH3 domains of pro-apoptotic members (Bad, Bak, Bid, Bim) interact with target proteins (Bcl-2, Bcl-X$_L$, Bcl-w) via a short region of alpha helix (indicated in FIG. 10) with the general formula:

[SEQ ID 56]

Baa$_1$-Xaa$_2$-Xaa$_3$-Xaa$_4$-Baa$_5$-Xaa$_6$-Xaa$_7$-Baa$_8$-Xaa$_9$-Zaa$_{10}$-Xaa$_{11}$-Baa$_{12}$

Where subscript number indicates residue position, Xaa is any natural alpha amino acid, Baa is a hydrophobic alpha amino acid, and Zaa is a negatively charged alpha amino acid.

The necessity of alpha helicity for binding allows bicyclic mimetics to be constructed (around the 1-12 region of formula (VI) based on the general formula:

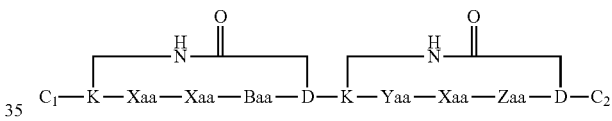

(VI)

Where C$_1$ is a hydrophobic N-terminal capping group, K is a lysine, D is an aspartate, Xaa is any natural or unnatural, Baa is any natural or unnatural hydrophobic alpha amino acid, Zaa is any natural or unnatural negatively charged alpha amino acid, C$_2$ is a hydrophobic C-terminal capping group.

Overlay of the NMR structure of the bicycle Ac-[KARAD][KARAD]—NH$_2$ [SEQ ID NO:46] over the crystal structure of the Bad helix (FIG. 10) shows it can position the side chains required for binding in the appropriate position. Examples of bicyclic molecules that can adopt this structure are given in Table 9.

TABLE 9

| Bicyclic Bad helix mimics | |
|---|---|
| cyclo(2-6, 7-11)-Y[KRELD][KMADD]F | SEQ ID NO: 57 |
| cyclo(2-6, 7-11)-V[KRQLD][KIADD]I | SEQ ID NO: 58 |
| cyclo(2-6, 7-11)-I[KAQED][KVADD]M | SEQ ID NO: 59 |
| cyclo(2-6, 7-11)-I[KAQED][KIADD]F | SEQ ID NO: 60 |
| cyclo(2-6, 7-11)-3-(4-hydroxyphenyl)-propionyl[KRELD][KMADD]-phenethylamide | SEQ ID NO: 61 |
| cyclo(2-6, 7-11)-iso-valeroyl[KRQLD][KIADD]2-methylbutylamide | SEQ ID NO: 62 |
| cyclo(2-6, 7-11)-3-methylpentanoyl-[KAQED][KVADD]-3-methylsulfanyl-propylamide | SEQ ID NO: 63 |

TABLE 9-continued

Bicyclic Bad helix mimics

| | |
|---|---|
| cyclo(2-6, 7-11)-3-methylpentanoyl-[KAQED][KIADD]-phenethylamide | SEQ ID NO: 64 |

Similarly monocyclic mimetics based on the general formula (VII) 5-12 region with appropriate capping groups at either end based on the general formula:

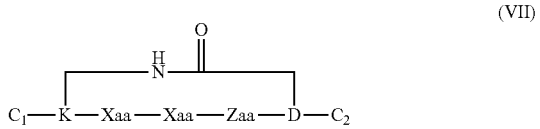

(VII)

Where $C_1$ is an N-terminal capping group, Xaa is any amino acid, Zaa is any negatively charged natural or unnatural alpha amino acid, $C_2$ is a C-terminal capping group. An overlay of the NMR structure of the monocycle Ac-[KARAD]—NH$_2$ [SEQ ID NO 8]onto the crystal structure of the complexed Bad peptide places the required side chains in the appropriate positions (FIG. 6). Examples of monocycles that can adopt the appropriate structure are given in Table 10.

TABLE 10

Monocyclic Bad helix mimics with peptidic and/or non-peptidic flanking regions

| | |
|---|---|
| Cyclo(3,7)-LR[KMADD]F | SEQ ID NO: 65 |
| Cyclo(3,7)-LA[KIADD]I | SEQ ID NO: 66 |
| Cyclo(3,7)-LA[KVADD]I | SEQ ID NO: 67 |
| Cyclo(3,7)-LA[KIADD]F | SEQ ID NO: 68 |
| Cyclo(2,6)-7-methyl octanoyl-[KMADD]-Phenethylamide | SEQ ID NO: 69 |
| Cyclo(2,6)-7-methyl octanoyl-[KIADD]-2-methylbutylamide | SEQ ID NO: 70 |
| Cyclo(2,6)-7-methyl octanoyl-[KVADD]-2-methylbutylamide | SEQ ID NO: 71 |
| Cyclo(2,6)-7-methyl octanoyl-[KMADD]-Phenethylamide | SEQ ID NO: 72 |

Fluorescence Polarization Assay

Binding affinities can be measured relative to the native peptide by competitive fluorescence polarization assay using the fluorescein labeled Bad peptide Flu-βANL-WAAQRYGRELRRMSDKKFVDSFKK-NH$_2$ as a probe. The dissociation constant of this peptide for Bcl-x$_L$ is 0.6 nM[130] and for Bcl-2 is 3 nM[131]. The assay is performed according to Zhang et al.[131] Briefly, a stock solution of 5 nM of the fluorescein labeled Bad peptide, 25 nm of Bcl-2, 1 mM EDTA, and 0.05% PEG-8000 in 20 mM phosphate buffer pH 7.4 is prepared. 120 μL of this solution is placed into 8 wells of a 96 well plate, and 25, 5, 1, 0.5, 0.25, 0.1, 0.05, 0.01 μM compound from a DMSO stock. The total DMSO concentration is adjusted to 5% by the addition of neat DMSO. A negative (5 nm Flu-Bad, 5% DMSO in buffer), and positive control (5 nm Bad peptide, 25 nm Bcl-2, 5% DMSO in buffer) were used to determine the free and bound polarization values for the assay. The plate is incubated for 2 hr at room temperature, and then polarization was measured at room temperature using a BMG FLUOstar fluorescence polarization spectrometer with excitation at 485 nm and emission at 530 nm. IC$_{50}$ values were obtained by non-linear least squares fitting of the data to the equation:

Observed polarization=(bound polarization–free polarization)1+10$^{(Log\,IC50-Concentration)}$ p53 Tumor Suppressor Mimetics

Background

The protein p53 acts as a potent tumor suppressor that prevents the proliferation of malignant cells causing cell cycle arrest or apoptosis, however it is the most frequently inactivated protein in human cancers[132]. p53 is tightly controlled by the protein MDM2, however its up-regulation results in the proliferation of cancer cells. It has been demonstrated that inhibitors of MDM2 can restore the cell cycle arrest of apoptotic mechanism resulting in the destruction of cancer cells[133], indicating that p53 binds to MDM2 via and alpha helical conformation. Furthermore is has been demonstrated that synthetic peptides corresponding to the p53 sequence, that contain helix inducing residues such as Aib (α-amino isobutyric acid) possess a higher affinity for MDM2 than the native peptide[135].

Strategy

The interaction of p53 with MDM2 depends on 3 critical hydrophobic contacts in a 12 residue sequence indicated by the general formula indicated below (FB)

Xaa-Xaa-Xaa-Baa-Xaa-Xaa-Xaa-Baa-Xaa-Xaa-Baa-Xaa (FB)

Where Xaa is any natural amino acid and Baa is any natural hydrophobic α-amino acid.

Modification of this sequence by others incorporating helix inducing amino acid residues has resulted in high affinity ligands for MDM2.

Acetyl-Phe-Met-Aib-Pmp-6C1W-Glu-Ac$_3$c-Leu-NH$_2$IC$_{50}$=5 nm

Where Aib is α-aminoisobutyric acid, Pmp is 4-(Phosphonomethyl)-L-phenylalanine, 6C1W is 6-Chloro-L-Tryptophan, and $Ac_3c$ is 1-aminocyclopropane carboxylic acid.

Application of the monocycle prototype would constrain the p53 sequence into the required conformation for binding to MDM2, resulting in high affinity, metabolically stable anticancer agents of the general formula (VIII).

(VIII)

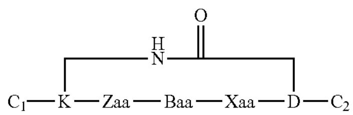

Where $C_1$ is a hydrophobic N-terminal capping group (natural or unnatural α-amino acid or dipeptide, aliphatic or aromatic carboxylic acid), K is a lysine, Zaa is a negatively, natural or unnatural α-amino acid, Baa is a hydrophobic, natural or unnatural α-amino acid—preferably an L-tryptophan derivative with halogen or alkyl substitution in the 5 or 6 position, Xaa is any natural or unnatural α-amino acid, D is aspartate, and $C_2$ is a hydrophobic C-terminal capping group (natural or unnatural α-amino acid or dipeptide, aliphatic or aromatic amine). Examples of molecules of this sort could include:

```
                                        SEQ ID: 73
Cyclo(3,7)-FM[K(Pmp)(6C1W)ED]L SEQ ID: 74
Cyclo(3,7)-3-Phenylpropanoyl-M[K(Pmp)(6C1W)ED]
isopentylamide SEQ ID: 75
Cyclo(2,6)-6-Phenylheptanoyl-[K(Pmp)(6C1W)ED]-
isopentylamide
```

Overlay of the NMR structure of monocycle on the crystal structure of p53 shows that the monocycle places the binding residues in the required positions (FIG. 11).

Fluorescence Polarization Assay

Binding affinities can be measured relative to the native peptide by competitive fluorescence polarization assay using the fluorescein labeled p53 peptide Ac—FR(Dpr-Flu)($Ac_6c$)(6-Br—W)EEL-$NH_2$ as a probe. The dissociation constant of this peptide for MDM2 is 2 nM (5). The assay is performed according to Zhang et. al.[136]. Briefly, a stock solution of 10 nM of the fluorescein labeled p53 peptide, 30 nM of MDM2, 1 mM EDTA, and 0.05% PEG-8000 in 20 mM phosphate buffer pH 7.4 is prepared. 120 μL of this solution is placed into 8 wells of a 96 well plate, and 25, 5, 1, 0.5, 0.25, 0.1, 0.05, 0.01 μM compound from a DMSO stock. The total DMSO concentration is adjusted to 5% by the addition of neat DMSO. A negative (10 nM Flu-p53, 5% DMSO in buffer), and positive control (10 nM Flu-p53 peptide, 30 nM MDM2, 5% DMSO in buffer) were used to determine the free and bound polarization values for the assay. The plate is incubated for 2 hr at room temperature, and then polarization was measured at room temperature using a BMG FLUOstar fluorescence polarization spectrometer with excitation at 485 nm and emission at 530 nm. $IC_{50}$ values were obtained by non-linear least squares fitting of the data to the equation:

$$\text{Observed polarization}=(\text{bound polarization}-\text{free polarization})1+10^{(Log\ IC50-Concentration)}$$

Example 15

GPCR Agonists/Antagonists

Pain/Addiction Therapies: ORL-1 Receptor Agonists Antagonists

Background

The function of the ORL-1 receptor includes pain transmission, stress and anxiety, learning and memory, locomotor activity, food intake, motivational properties of drugs of abuse[137] Agonists of the ORL-1 receptor have likely uses for anti-anxiety therapy, appetite suppressants, alcohol and opiate withdrawal therapies, anti-epilepsy drugs. Antagonists of the ORL-1 receptor have likely uses for analgesia/pain therapy, alleviation of memory disorders[137].

Strategy

The receptor is activated by the endogenous ligand nociceptin which has the sequence:

$F_1$-$G_2$-$G_3$-$F_4$-$T_5$-$G_6$-$A_7$-R-$K_9$-$S_{10}$-$A_{11}$-$R_{12}$-$K_{13}$-$L_{14}$-$A_{15}$

Portions of this sequence serve different roles, the four N-terminal residues (FGGF) serves as a 'message sequence', actually activating the receptor, whilst the remaining sequence serves as an 'address' and is responsible for receptor binding and specificity, SAR data indicated that the dibasic repeat (residues 8,9 and 12,13) is especially important for binding[138]. On the basis of NMR evidence and SAR, it has been proposed that the address sequence binds to the ORL-1 receptor in an α-helical conformation[139]. Further support for this hypothesis has been evidenced in the synthesis of nociceptin analogues containing Aib residues (which are known helix promoters) resulting in 10-fold increases in affinity of these peptides for the ORL-1 receptor. Based on previous data[140] it appears constraining the address sequence into an α-helical conformation would improve activity. Therefore mimetics based on constraining the address sequence could provide highly active and selective agonists for treating anxiety, obesity, epilepsy and drug/alcohol addiction. Replacing the N terminal residue from a Phenylalanine (F) and N-benzylglycine (Nphe) switches the activity from agonism to antagonism, it has also been shown that attaching non-selective, non-peptidic opioid antagonists to the nociceptin address sequence can target the antagonists selectively to the ORL-1 receptor[141] which could be useful therapeutics for chronic pain. Thus the proposed agonists/antagonists would bear the general formula (IX):

(IX)

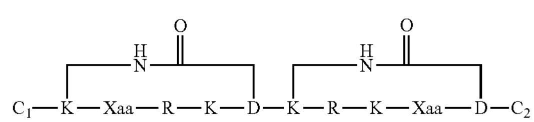

Where $C_1$ is a suitable N-terminal capping group (1-5 natural or unnatural α-amino acids, aliphatic/aromatic carboxylic acid or non-peptidic opioid antagonist), K is lysine, Xaa is any amino acid, D is aspartate, $C_2$ is a suitable C-terminal capping group (primary or an aliphatic/aromatic secondary amide). Compounds of this type could include:

```
Cyclo(6-10, 11-15)-FGGFT[KARKD][KRKLD]-NH₂ (agonist)                                    SEQ ID NO: 76

Cyclo(6-10, 11-15)-NpheGGFT[KARKD][KRKLD]-NH₂ (antagonist)                              SEQ ID NO: 77

Cyclo(2-6, 7-11)-Ac-T[KARKD][KRKLD]-NH₂ (antagonist)                                    SEQ ID NO: 78

SEQ ID NO: 79
Cyclo(2-6, 7-11)-(8-napthalen-1-yl-methyl-4-oxo-1-phenyl-1,3,8-triaza-
spiro[4,5]dec-3-yl)-acetoyl-[KARKD][KRKLD]-NH2 (antagonist)
```

Furthermore the endogenous ligand is known to be cleaved by endopeptidases at the several positions[137] (see below). Given that the monocyclic and bicyclic strategy prevent cleavage by proteases within the cycle, the mimetics described above would be expected to be metabolically stable.

FGGFTGARKSARKLANQ

Membranes from recombinant HEK-293 cells expression hORL-1 are prepared as described in (Zhang et al.)[140]. The above peptides are incubated with 0.1 nM [³H]-nociceptin, 20 μg membrane protein/well in a final volume of 500 μL of binding buffer in 96-well plates for 2 hr at room temperature. Binding reactions are terminated by rapid filtration onto 96 well Unifilter GF/C filter plates pre-soaked in 0.5% polyethylenamine using 96-well tissue harvester, followed by three washes with ice cold binding buffer. Filter plates are dried at 50° C.° for 3 hrs, and then scintillation cocktail is added (50 μg/well) and plates counted in a scintillation counter for 1 min/well. Data is analyzed using the one-site competition curve fitting function in PRISM.

Figure 12:
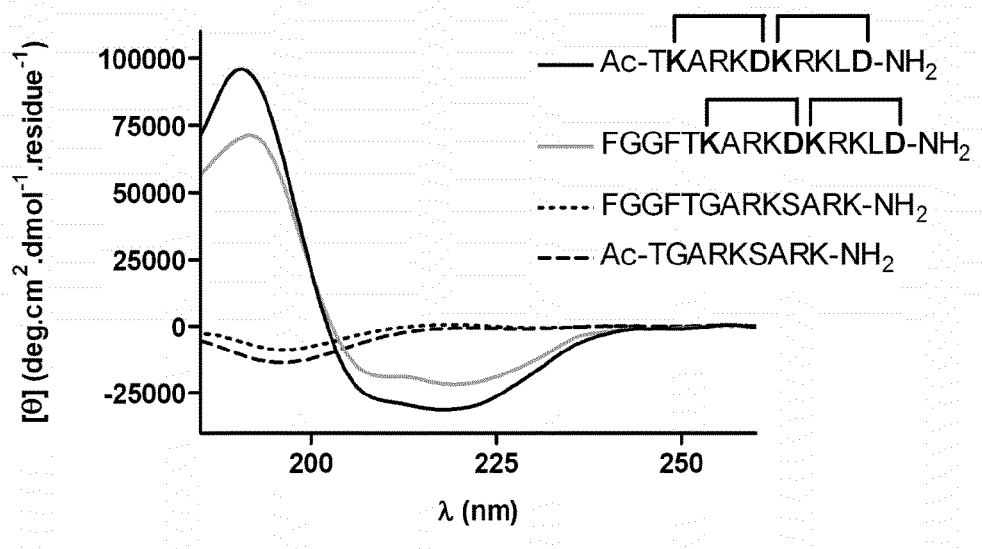
FIG. 12 depicts CD spectra of constrained nociception mimetic SEQ ID NOs: 79 and 77, known as peptidic agonist (FGGFTGARKSARK-NH$_2$; SEQ ID NO: 80, Ki:0.3 nM), and linear address sequence (AcTGARKSARK-NH$_2$, SEQ ID NO: 81).

Incorporation of the bicyclic strategy as indicated above has been shown by CD spectroscopy to increase helicity in 76 and 77 compared to the reported native agonist and antagonist sequences (F/Nphe-GGFTGARKSARK) as indicated in FIG. 12.

Experimental Materials and Methods

General

Fmoc-Asp(OAllyl)-OH and tetrakis(triphenylphosphino) palladium were obtained from Sigma-Aldrich (Sydney, Australia). Boc-Lys(Fmoc)-OH, Rink Amide MBHA resin and other L-amino acids were obtained from Novabiochem (Melbourne, Australia). Benzotriazol-1-yl-1,1,3,3-tetramethyluronium (HBTU) and benzotriazol-1-yloxy-tris(dimethylamino)-phosphonium (BOP) were obtained from Richelieu Biotechnologies (Quebec Canada). All other reagents were of peptide synthesis grade and obtained from Auspep (Melbourne, Australia).

NMR Spectroscopy

Samples for NMR analysis of peptides were prepared by dissolving the peptide 3 mg in 450 ul H₂O and 50 ul D₂O(5 mmol) and adjusting the pH of the solution to 4.5 by adding HCl or NaOH and stirring for 30 min. 1D and 2D ¹H NMR spectra were recorded on both Bruker ARX-500 and Bruker Avance DMX-750 spectrometers at 278K. All spectra were recorded in the phase sensitive mode using time proportional phasing incrementation[96]. 2D experiments included TOCSY using MLEV-17 spin lock sequence with a mixing time of 100 ms, NOESY with a mixing time of 300 ms. Water suppression was achieved using watergate W5 pulse sequences with gradients using double echo[97]. 2D TOCSY and NOESY experiments were recorded over 7936.5 Hz with 4096 complex data points in F2 and 512 increments in F1 with 16 and 48 scans per increment respectively. Spectra were processed using XWINNMR (Bruker, Germany). The t1 dimensions of all 2D spectra were zero filled with 2048 real data points, and 90° phase-shifted sine bell window functions applied in both dimensions followed by fourier transformation and fifth order polynomial baseline correction. Chemical shifts were referenced to TSP an internal standard at 0.00 ppm. Processed spectra were analyzed using the program SparkyNMR[98] and assigned using the sequential assignment technique[99].

Structure Calculations

Cross peaks in NOESY spectra were integrated and calibrated in SparkyNMR[98], and distance constraints derived using the standard CALIBA function in DYANA[100]. Corrections for pseudo atoms were added to distance constraints where needed. Backbone dihedral angle restraints were inferred from $^3J_{NHCH\alpha}$ coupling constants in 1D spectra at 278K and 288K, φ was restrained to—65±30° for $^3J_{NHCH\alpha}$<6 Hz. Peptide bond o3 angles were all set to trans, and structures were calculation without explicit hydrogen bond restraints. Stereospecific assignments of β-methylene protons and χ1 dihedral angles were derived from 1D ¹H spectra $^3J_{\alpha\beta}$ and set to −60±300 for both aspartic acid residues. Initial structures were generated using a torsion angle simulated annealing protocol in DYANA until no violations were obtained. Final structures were calculated using XPLOR3.851. Starting structures with randomized φ and ψ angles and extended side chains were generated using an ab initio simulated annealing protocol[101]. The calculations were performed using the standard forcefield parameter set (PARALLHDG.PRO) and topology file (TOPALLHDG.PRO) in XPLOR with in house modifications to generated lactam bridges between lysing and aspartic acid residues. Refinement of structures was achieved using the conjugate gradient Powell alogrithm with 1000 cycles of energy minimization and a refined forcefield based on the program CHARMm[102]. Structures were visualized with MOLMOL[103] and InsightII[104].

CD Spectroscopy

CD experiments were performed on a Jasco Model J-710 spectropolarimeter which was routinely calibrated with (1S)-(+)-10-camphorsulfonic acid. Temperature control was achieved using a Neslab RTE-111 circulating water bath. Spectra were recorded in a 0.1 cm Jasco cell between 310-185 nm at 50 nm/min with a band width of 1.0 nm, response time of 2 sec, resolution step width of 0.1 nm and sensitivity of 20, 50 or 100 mdeg. Each spectrum represents the average of 5 scans with smoothing to reduce noise. Peptide samples for CD spectroscopy were dissolved in distilled water (~1 mg/mL). Each stock solution was diluted to a final concentration of 50 μM in 10 mM sodium phosphate buffer (pH7.4), with or without additives (2,2,2-trifluoroethanol (TFE) or guanidine.HCl). Guanidine.HCl denaturation experiments were performed according to Creighton[105].

Accurate concentration determination of stock solutions were obtained by 1D $^1$H NMR using the method of Larive et. al.[106] Briefly 475 μL of the initial peptide stock solution was mixed with 50 μL of D$_2$O, and spiked with an internal standard 25 μL of 10.077 mM DSS (the concentration of which had carefully been back-calibrated by NMR from a standard solution of L-tryptophan—the concentration of which was determined by UV $\epsilon_{278}$=5579). 1D $^1$H NMR spectra were then recorded with presaturation and a relaxation delay (d1) of 30 seconds to allow for full relaxation of peptide and DSS$^1$H signals to facilitate accurate integration of proton signals with S/N>250:1. This method provides reproducible concentrations within ±2%.

Circular Dichroism Data Analysis

CD data in ellipticity was converted to mean peptide ellipticity using the equation:

$$[\theta]=\theta/(10 \times C \times N_p \times 1)$$

where $\theta$ is the ellipticity in millidegrees, C is the peptide molar concentration (M), 1 is the cell path length (cm), and $N_p$ is the number of peptide units (ie. pentapeptides $N_p$=6, hexapeptides $N_p$=7, 10 & 11 $N_p$=5, 12 $N_p$=4.)

Relative helicities were employed to allow scaling of compounds by dividing the $[\theta]_{obs215}(8)/[\theta]_{obs215}(x)$ for pentapeptides, and $[\theta]_{obs215}(24)/[\theta]_{obs215}(x)$ for hexapeptides.

The disclosure of every patent, patent application, and publication cited herein is hereby incorporated herein by reference in its entirety.

The citation of any reference herein should not be construed as an admission that such reference is available as "Prior Art" to the instant application.

Throughout the specification the aim has been to describe the preferred embodiments of the invention without limiting the invention to any one embodiment or specific collection of features. Those of skill in the art will therefore appreciate that, in light of the instant disclosure, various modifications and changes can be made in the particular embodiments exemplified without departing from the scope of the present invention. All such modifications and changes are intended to be included within the scope of the appended claims.

BIBLIOGRAPHY (1) Barlow, D. J.; Thornton, J. M. *J. Mol. Biol.* 1988, 201, 601.
(2) Fairlie, D.; West, M.; Wong, A. *Curr. Med. Chem.* 1998, 5, 29.
(3) Andrews, M. J. I.; Tabor, A. B. *Tetrahedron* 1999, 55, 11711.
(4) Kussie, P. H.; Gorina, S.; Marechal, V.; Elenbaas, B.; Moreau, J.; Levine, A. J.; Pavletich, N. P. *Science* 1996, 274, 948-953.
(5) Burley, S. K.; Roeder, R. G. *Ann. Rev. Biochem.* 1996, 65, 769.
(6) Uesugi, M.; Nyaguile, O.; Lu, H.; Levine, A. J.; Verdine, G. L. *Science* 1997, 277, 1310.
(7) Sattler, M.; Liang, H.; Nettesheim, D.; Meadows, R. P.; Harlan, J. E.; Eberstadt, M.; Yoon, H. S.; Shuker, S. B.; Chang, B. S.; Minn, A. J.; Thompson, C. B.; Fesik, S. W. *Science* 1997, 275, 983-986.
(8) Tan, R.; Chen, L.; Buettner, J. A.; Hudson, D.; Frankel, A. D. *Cell* 1993, 73, 1031.
(9) Pabo, C. O.; Peisach, E.; Grant, R. A. *Annual Review of Biochemistry* 2001, 70, 313-340.
(10) Weiss, M. A.; Narayana, N. *Biopolymers* 1998, 48, 167-180.
(11) Botuyan, M. V.; Mer, G.; Yi, G.; Koth, C. M.; Case, D. A.; Edwards, A. M.; Chazin, W. J.; Arrowsmith, C. H. *J. Mol. Biol.* 2001, 312, 177-186.
(12) Uesugi, M.; Nyanguile, O.; Lu, H.; Levine, A. J.; Verdine, G. L. *Science* 1997, 277, 1310-1313.
(13) Jin, L.; Briggs, S. L.; Chandrasekhar, S.; Chirgadze, N. Y.; Clawson, D. K.; Scheivitz, R. W.; Smiley, D. L.; Tashjian, A. H.; Zhang, F. *Journal of Biological Chemistry* 2000, 275, 27238-27244.
(14) Schwyzer, R. *Biochemistry* 1986, 25, 4281-4286.
(15) Bennett, M. A.; Murray, T. F.; Aldrich, J. V. *Journal of Medicinal Chemistry* 2002, 45, 5617-5619.
(16) Zaiou, M. Z.; Arnold, K. S.; Newhouse, Y. M.; Innerarity, T. L.; Weisgraber, K. H.; Segall, M. L.; Phillips, M. C.; Lund-Katz, S. *Journal of LipidReseach* 2000, 41, 1087-1095.
(17) Kirby, D. A.; Koerber, S. C.; Craig, A. G.; Feinstein, R. D.; Delmas, L.; Brown, M. R.; Rivier, J. E. *Journal of Medicinal Chemistry* 1993, 36, 385-393.
(18) Carpenter, K. A.; Schmidt, R.; Yue, S. Y.; Hodzic, L.; Pou, C.; Payza, K.; Godbout, C.; Brown, W.; Roberts, E. *Biochemistry* 1999, 38, 15295-15304.
(19) Miranda, A.; Lahrichi, S. L.; Gulyas, J.; Koerber, S. C.; Craig, A. G.; Corrigan, A.; Rivier, C.; Vale, W.; Rivier, J. *Journal of Medicinal Chemistry* 1997, 40, 3651-3658.
(20) Li, J. Z.; Matsuura, J. E.; Waugh, D. J. J.; Adrian, T. E.; Abel, P. W.; Manning, M. C.; Smith, D. D. *Journal of Medicinal Chemistry* 1997, 40, 3071-3076.
(21) Nicole, P.; Lins, L.; Rouyer-Fessard, C.; Drouot, C.; Fulcrand, P.; Thomas, A.; Couvineau, A.; Martinez, J.; Brasseur, R.; Laburthe, M. *J Biol Chem* 2000, 275, 24003-24012.
(22) McInerney, E. M.; Rose, D. W.; Flynn, S. E.; Westin, S.; Mullen, T. M.; Krones, A.; Inostroza, J.; Torchia, J.; Nolte, R. T.; Assa-Munt, N.; Milburn, M. V.; Glass, C. K.; Rosenfeld, M. G. *Genes Dev* 1998, 12, 3357-3368.
(23) Chang, C.; Norris, J. D.; Gron, H.; Paige, L. A.; Hamilton, P. T.; Kenan, D. J.; Fowlkes, D.; McDonnell, D. P. *Mol Cell Biol* 1999, 19, 8226-8239.
(24) Zimm, B.; Bragg, J. *J. Chem. Phys.* 1959, 31, 526.
(25) Scholtz, A.; Baldwin, R. L. *Annu. Rev. Biophys. Biomol. Struct.* 1992, 21, 95.
(26) Kemp, D.; Curran, T.; Boyd, J.; Allen, T. *J. Org. Chem.* 1991, 56, 6683.
(27) Müller, K.; Obrecht, D.; Knierzinger, A.; Stankovic, C.; Spiegler, C.; Bannwarth, W.; Trzeciak, A.; Englert, G.; Labhardt, A. M.; Schoenholzer, P. *Perspect. Med. Chem.* 1993, 513.
(28) Austin, R.; Maplestone, R. A.; Sefler, A. M.; Liu, K.; Hruzewicz, W. N.; Liu, C.; Cho, H. S.; Wemmer, D. E.; Bartlett, P. A. *J. Am. Chem. Soc.* 1997, 119, 6461.
(29) Aurora, R.; Rose, G. D. *Protein Science* 1998, 7, 21.
(30) Ghadiri, M. R.; Choi, C. *J. Am. Chem. Soc.* 1990, 112, 1630.
(31) Ruan, F.; Chen, Y.; Hopkins, P. B. *J. Am. Chem. Soc.* 1990, 112, 9403.

(32) Ghadiri, M. R.; Fernholz, H. *J. Am. Chem. Soc.* 1990, 112, 9633.
(33) Kohn, W. D.; Kay, C. M.; Sykes, B. D.; Hodges, R. S. *J. Am. Chem. Soc.* 1998, 120, 1124.
(34) Kelso, M. J.; Hoang, H.; Appleton, T. G.; Fairlie, D. P. *J. Am. Chem. Soc.* 2000, 122, 10488.
(35) Kelso, M. J.; Hoang, H. N.; Oliver, W. N.; Sokolenko, N.; March, D. R.; Appleton, T. G.; Fairlie, D. P. *Angew Chem, Int. Edit.* 2003, 42, 421-424.
(36) Rajashankar, K. R.; Ramakumar, S.; Jain, R. M.; Chauhan, V. S. *J. Am. Chem. Soc.* 1995, 117, 10129.
(37) Karle, I. L.; Balaram, P. *Biochem.* 1990, 29, 6747.
(38) Mayne, L.; Englander, S. W.; Qiu, R.; Yang, J.; Gong, Y.; Spek, E. J.; Kallenbach, N. R. *J. Am. Chem. Soc.* 1998, 120, 10643.
(39) Albert, J. S.; Hamilton, A. *Biochem.* 1995, 34, 984.
(40) Pellegrini, M.; Royo, M.; Chorev, M.; Mierke, D. F. *J. Pep. Res.* 1997, 49, 404.
(41) Jackson, D. Y.; King, D. S.; Chmielewski, J.; Singh, S.; Schultz, P. G. *J. Am. Chem. Soc.* 1991, 113, 9391.
(42) Cabezas, E.; Satterthwait, A. C. *J. Am. Chem. Soc.* 1999, 121, 3862.
(43) Taylor, J. W. *Biopolymers* 2002, 66, 49.
(44) Schievano, E.; Mammi, S.; Bisello, A.; Rosenblatt, M.; Chorev, M.; Peggion, E. *J Pept. Sci.* 1999, 5, 330.
(45) Bracken, C.; Gulyas, J.; Taylor, J. W.; Baum, J. *J. Am. Chem. Soc.* 1994, 116, 6431.
(46) Phelan, J. C.; Skelton, N. J.; Braisted, A. C.; McDowell, R. S. *J. Am. Chem. Soc.* 1997, 119, 455. (e) Taylor, J. W.; Yu, C. *Bioorg. Med. Chem.* 1999, 7, 161.
(47) Chen, S.-T.; Chen, H.-J.; Yu, H.-M.; Wang, K.-T. *J. Chem. Res.* (S) 1993, 228;
(48) Osapay, G.; Taylor, J. W. *J. Am. Chem. Soc.* 1992, 114, 6966.
(49) Yu, C.; Taylor, J. W. *Tet Lett.* 1996, 37, 1731.
(50) Geistlinger T. R.; Guy, R. K. *J. Am. Chem. Soc.* 2001, 123, 1525.
(51) Schafineister, C. E.; Po, J.; Verdine, G. L. *J. Am. Chem. Soc.* 2000, 122, 5891.
(52) Blackwell, H. E.; Sadowsky, J. D.; Howard, R. J.; Sampson, J. N.; Chao, J. A.; Steinmetz, W. E.; O'Leary, D. J.; Grubbs, R. H. *J. Org. Chem.* 2001, 66, 5291.
(53) Judice, J. K.; Tom, J. Y. K.; Huang, W.; Wrin, T.; Vennari, J.; Petropoulos, C. J.; McDowell, R. S. *Proc. Natl. Acad. Sci.* 1997, 94, 13426.
(54) Orner, B. P.; Ernst, J. T.; Hamilton, A. D. *J. Am. Chem. Soc.* 2001, 123, 5382.
(55) Kutzki, O.; Park, H. S.; Ernst, J. T.; Orner, B. P.; Yin, H.; Hamilton, A. D. *J. Am. Chem. Soc.* 2002, 124, 11838.
(56) Ernst, J. T.; Becerril, J.; Park, H. S.; Yin, H.; Hamilton, A. D. *Angew Chem. Int. Edit.* 2003, 42, 535.
(57) Kemp, D. S.; Curran, T. P.; Davis, W. M.; Boyd, J. G.; Muendel, C. *Journal of Organic Chemistry* 1991, 56, 6672-6682.
(58) Kemp, D. S.; Rothman, J. H. *Tetrahedron Letters* 1995, 36, 4019-4022.
(59) Kemp, D. S.; Rothman, J. H. *Tetrahedron Letters* 1995, 36, 4023-4026.
(60) Kemp, D. S.; Rothman, J. H.; Curran, T. C.; Blanchard, D. E. *Tetrahedron Letters* 1995, 36, 3809-3812.
(61) Kemp, D. S.; Rothman, J. H. *Tetrahedron Letters* 1995, 36, 3813-3816.
(62) Mueller, K.; Obrecht, D.; Knierzinger, A.; Stankovic, C.; Spiegler, C.; Bannwarth, W.; Trzeciak, A.; Englert, G.; Labhardt, A. M.; Schoenholzer, P. *Perspectives in Medicinal Chemistry* 1993, 513-531.
(63) Kahn, M.; Kim, H.-O.; Urban, J.; Molecumetics Ltd.: United States, 1999; Vol. 5859184.
(64) Cabezas, E.; Satterthwait, A. C. *J. Am. Chem. Soc.* 1999, 121, 3862-3875.
(65) Lyu, P. C.; Sherman, J. C.; Chen, A.; Kallenbach, N. R. *Proc. Natl. Acad. Sci. U.S.A.* 1991, 88, 5317-5320.
(66) Zhang, C.; Miller, W.; Valenzano, K. J.; Kyle, D. *J. Journal of Medicinal Chemistry* 2002, 45, 5280-5286.
(67) Garcia-Echeverria, C.; Chene, P.; Blommers, M. J. J.; Furet, P. *Journal of Medicinal Chemistry* 2000, 43, 3205-3208.
(68) Bryant, S. D.; Guerrini, R.; Salvadori, S.; Bianchi, C.; Tomatis, R.; Attila, M.; Lazarus, L. H. *Journal of Medicinal Chemistry* 1997, 40, 2579-2587.
(69) Leduc, A.; Trent, J. O.; Wittliff, J. L.; Bramlett, K. S.; Briggs, S. L.; Chirgadze, N. Y.; Wang, Y.; Burris, T. P.; Spatola, A. F. *Proc. Natl. Acad. Sci. U.S.A.* 2003, 100, 11273-11278.
(70) Houston, M. E.; Gannon, C. L.; Kay, C. M.; Hodges, R. S. *Journal of Peptide Science* 1995, 1, 274-282.
(71) Tian, Y.; Ramesh, C. V.; Ma, X.; Naqvi, S.; Patel, T.; Cenizal, T.; Tiscione, M.; Diaz, K.; Crea, T.; Arnold, E.; Arnold, G. F.; Taylor, J. W. *Journal of Peptide Research* 2002, 59, 264-276.
(72) Blackwell, H. E.; Grubbs, R. H. *Angewandte Chemie-International Edition* 1998, 37, 3281-3284.
(73) Fairlie D P, Abbenante G, March D R: Macrocyclic peptidomimetics—forcing peptides into bioactive conformations. *Curr. Med. Chem.* (1995) 2:654-686.
(74) Stradley, S.; Rizo, J.; Bruch, M.; Stroup, A.; Gierasch, L. *Biopolymers,* 1990, 29, 263.
(75) Toniolo, C. *Int. J. Peptide Protein Res.* 1990, 35, 287.
(76) Schiller, P. W. in Medicinal Chemistry for the 21st Century, Wermuth, C. G. (ed.) IUPAC/Blackwell, London, 1992, pp. 215-232.
(77) Kemp, D. S. in Medicinal Chemistry for the 21st Century, Wermuth, C. G. (ed.) IUPAC/Blackwell, London, 1992, pp. 259-277.
(78) Kessler, H.; Diefenbach, B.; Finsinger, D.; Geyer, A.; Gurrath, M.; Goodman, S. L.; Hoelzemann, G.; Haubner, R.; Jonczyk, A. *Lett. Pept. Sci.* 1995, 2, 155.
(79) Marraud, M.; Aubry, A. *Biopolymers* 1996, 40, 45.
(80) X.-M. Cheng, S, S, Nikam, Doherty, A. M. *Curr. Med. Chem.* 1994, 1, 271.
(81) Holzemann, G. *Kontakte* (Darmstadt) 1991, 1, 3-12; 2, 55.
(82) Zhang L H, Pesti J A, Costello T D, Sheeran P J, Uyeda R, Ma P, Kauffman G S, Ward R, McMillan J L: An efficient synthesis of cyclic RGD peptides as antithrombotic agents. *J. Org. Chem.* (1996) 61:5180-5185.
(83) Haubner R, Finsinger D, Kessler H: Stereisomeric peptide libraries and peptidomimetics for designing selective inhibitors of the V 3 integrin for a new cancer therapy. *Angew. Chem., Int. Ed. Engl.* (1997) 36:1374-1389.
(84) White H D: Unmet therapeutic needs in the management of acute ischemia. *Am. J. Cardiology* (1997) 80:B2-B10.
(85) Finch, A. M.; Wong, A. K.; Wadi, S. K.; Paczkowski, N. J.; Fairlie, D. P.; Taylor, S. M. Low Molecular Weight Peptidic and Cyclic Antagonists of the Receptor for the Complement Factor C5a, *J. Med. Chem.* 1999, 42, 1965-1974.
(86) McDonnel P A, Caldwell G W, Leo G C, Podlogar B L, Maryanoff B E: NMR three dimensional solution structure of the serine protease inhibitor cyclotheonamide A. *Biopolymers* (1997) 41: 349-358.

(87) Gani, D.; Lewis, A.; Rutherford, T.; Wilkie, J.; Stirling, I.; Jenn, T.; Ryan, M. D. *Tetrahedron* 1998, 54, 15793-15819.

(88) Lewis, A.; Ryan, M. D.; Gani, D. *Journal of the Chemical Society-Perkin Transactions* 1 1998, 3767-3775.

(89) Lewis, A.; Wilkie, J.; Rutherford, T. J.; Gani, D. *Journal of the Chemical Society-Perkin Transactions* 1 1998, 3777-3793.

(90) Lewis, A.; Rutherford, T. J.; Wilkie, J.; Jenn, T.; Gani, D. *Journal of the Chemical Society-Perkin Transactions* 1 1998, 3795-3806.

(91) Roberge et. al. Science, 269, 202-204, 1995

(92) Fields, C G, Lloyd D H. Macdonald R L. Otteson K M. Noble R L; Peptide Research 4(2), 95-101, 1991.

(93) Sambrook et. al. Molecular Cloning: A Laboratory Manual, $2^{nd}$ Edition, Cold Spring Harbor Laboratory Press Plainview, N.Y., 1989.

(94) Green T W and Wutz P, Protective groups in Organic Synthesis, John Wiley & Son, $3^{rd}$ Edition, 1999.

(95) John Jones, Amino Acid and Peptide Synthesis, Oxford University Press, 1992. New York

(96) Marion, D.; Wüthrich, K. *Biochem. Biophys. Res. Commun.* 113: 967 (1983).

(97) Liu, M.; Mao, X.; He, C.; Huang, H.; Nicholson, J. K.; Lindon, J. C. *J. Magn. Reson.* 132: 125 (1998)

(98) T. D. Goddard and D. G. Kneller, SPARKY 3, University of California, San Francisco.

(99) Wüthrich, K. *NMR of Proteins and Nucleic Acids*. Wiley-Interscience. New York. (1986).

(100) Güntert, P., Mumenthaler, C. & Wüthrich, K. *J. Mol. Biol.* 273: 283-298 (1997).

(101) Nilges, M.; Gronenborn, A. M.; Brünger, A. T.; Clore, G. M. *Prot. Eng.* 2: 27 (1988).

(102) Brooks, B. R.; Bruccoleri, R. E.; Olafson, B. D.; States, D. J.; Swaminathan, S.; Karplus, M. *J. Comput. Chem.* 4: 187 (1983).

(103) Koradi, R., Billeter, M., and Wëthrich, K. *J Mol Graphics* 14, 51-55 (1996)

(104) Insight II, Version 2000, Molecular Simulations Inc. San Diego Calif.

(105) Creighton, T. E. Protein Structure: *A Practical Approach.* $2^{nd}$ Ed. Oxford University Press, New York. pp$^{299}$-$3^{21}$. (1997).

(106) Larive, C. K.; Jayawickrama, D.; Orfi, L. *Appl. Spec.* 51: 1531 (1997).

(107) Engelbretsen, D. R.; Garnham, B. G.; Bergman, D. A.; Alewood, P. F. *Tetrahedron Lett.* 36: 8871 (1995).

(108) Sarin, V.; Kent, S. B. H.; Tan, J. P.; Merrifield, R. B. *Anal. Biochem.* 117: 147 (1981).

(109) Wishart, D. S.; Sykes, B. D.; Richards, F. M. *Biochem.* 1992, 31, 1647.

(110) Dyson, H. J.; Wright, P. E. *Ann. Rev. Biophys. Chem.* 1991, 20, 519.

(111) Waltho, J. P.; Feher, V. A.; Merutka, G.; Dyson, H. J.; Wright, P. E. *Biochemistry* 1993, 32, 6337.

(112) Güntert, P.; Mumenthaler, C.; Wüthrich, K. *J. Mol. Biol.* 1997, 273, 283.

(113) Brünger, A. T. X-PLOR *Manual Version* 3.1, 1992, Yale University, New Haven, Conn.

(114) Osapay, G., Taylor, J. W., J. Am. Chem. Soc., 1990, 112, 6046-6051.

(115) Condon, S. M. et. al., J. Am. Chem. Soc., 2000, 112, 3007-3014.

(116) Chin, D. H.; Woody, R. W.; Rohl, C. A.; Baldwin, R. L., Proc. Natl. Acad. Sci. U.S.A. 2002, 99, 15416-15421

(117) Tinoco Jr., I.; Woody, R. W.; Bradley, D. F., J. Chem. Phys. 1963, 38, 1317-1325

(118) Woody, R. W.; Tinoco Jr., I., J. Chem. Phys. 1967, 42, 4927-4944

(119) Woody, R. W.; Koslowski, A., Biophys. Chem. 2002, 101, 535-551

(120) Manning, M. C.; Woody, R. W., Biopolymers 1991, 31, 569-586

(121) Wallimann, P.; Kennedy, R. J.; Miller, J. S.; Shalongo, W.; Kemp, D. S., J. Am. Chem. Soc. 2003, 125, 1203-1220

(122) Luo, P. Z.; Baldwin, R. L., *Biochemistry* 1997, 36, 8413-8421

(123) Rohl, C. A.; Baldwin, R. L., *Methods Enzymol.* 1998, 295, 1-26

(124) Tian, Y.; Ramesh, C. V.; Ma, X.; Naqvi, S.; Patel, T.; Cenizal, T.; Tiscione, M.; Diaz, K.; Crea, T.; Arnold, E.; Arnold, G. F.; Taylor, J. W., *J. Pept. Res.* 2002, 59, 264-276

(125) Tyndall, J. D. A.; Fairlie, D. P., *J. Mol. Recognit.* 1999, 12, 363-370; (b) Fairlie, D. P.; Tyndall, J. D. A.; Reid, R. C.; Wong, A. K.; Abbenante, G.; Scanlon, M. J.; March, D. R.; Bergman, D. A.; Chai, C. L. L.; Burkett, B. A., *J. Med. Chem.* 2000, 43, 1271-1281

(126) Cory, S.; Huang, D. C. S.; Adams, J. M., *Oncogene.,* 2003, 22: 8590-8607; Wang, S.; Yang, D.; Lippman, M. E., *Seminars in Oncology.,* 2003, 30(5):133-142.). The crystal/NMR structures of Bad-Bcl-xL (1g5j) (Petros, A. M.; Nettesheim, D. G.; Wang, Y.; Olejniczak, E. T.; Meadows, R. P.; Mack, J.; Swift, K.; Matayoshi, E. D.; Zhang, H.; Thompson, C. B.; Fesik, S. W. *Protein Science.* 2000, 9:2528-2534

(127) Sattler, M.; Liang, H.; Nettesheim, D.; Meadows, R. P.; Harlan, J. E.; Eberstadt, M.; Yoon, H. S.; Shuker, S. B.; Chang, B. S.; Minn, A. J.; Thompson, C. B.; Fesik, S. W. Science. 1997. 275:983-986

(128) Petros, A. M.; Nettesheim, D. G.; Wang, Y.; Olejniczak, E. T.; Meadows, R. P.; Mack, J.; Swift, K.; Matayoshi, E. D.; Zhang, H.; Thompson, C. B.; Fesik, S. W. *Protein Science.* 2000, 9:2528-2534

(129) Liu, X.; Dai, S.; Zhu, Y.; Marrack, P.; Kappler, J. W. *Immunity.* 2003. 19:341-352

(130) Joseph, M. K.; Solomon, L. R.; Petros, A. M.; Cai, J.; Simmer, R. L.; Zhang, H.; Rosenberg, S.; Ng, S. *Oncogene.* 2004, 23:835-38

(131) Zhang, H.; Niummer, P.; Rosenberg, S. H.; Ng, S.; Joseph, M., *Anal. Biochem.* 2002, 307: 70-75

(132) Hollstein, M.; Sidransky, D.; Vogelstein, C.; Harris, C. *Science.* 1991, 253: 49

(133) Vassilev, L. T.; Vu, B. T.; Graves, B.; Carvajal, D.; Podlaski, F.; Filipovic, Z.; Kong, N.; Kammlott, U.; Lukacs, C.; Klein, C.; Fotouhi, N.; Liu, E. A. *Science.* 2004, 303:844-848

(134) Kussie, P. H.; Gorina, S.; Marechal, V.; Elenbaas, B.; Moreau, J.; Levine, A. J.; Pavletich, N. P., *Science.* 1996, 274: 948-953

(135) Garcia-Echeverria, C.; Chene, P.; Blommers, M. J. J.; Furet, P., *J. Med. Chem.* 2000, 43: 3205-3208

(136) Zhang, R.; Mayhood, T.; Lipari, P.; Wang, Y.; Durkin, J.; Syto, R.; Gesell, J.; McNemar, C.; Windsor, W., *Anal. Biochem.* 2004, 331:138-146

(137) Calo, G.; Guerrini, R.; Salvadori, S.; Regoli, D. *Brit. J. Pharmacol.* 2000, 129:1261-83

(138) Reinscheid, R. K.; Ardati, A.; Monsma Jr, F. J.; Civelli, O. *J. Biol. Chem.* 1996, 24(14): 14163-68

(139) Salvadori, S.; Picone, D.; Tancredi, T.; Guerrini, R.; Spadaccini, R.; Lazarus, L. H.; Regoli, D.; Temussi, P. A. *Biochem. Biophys. Res. Comm.* 1997, 233:640-643

(140) Zhang, C.; Miller, W.; Valenzano, K. J.; Kyle, D. J., *J. Med. Chem.* 2002, 45:5280-5286

(141) Guerrini, R.; Carra, G.; Calo, G.; et al. *J. Pept. Res.* 2004, 63:477-484

What is claimed is:

1. A compound having the formula (I):

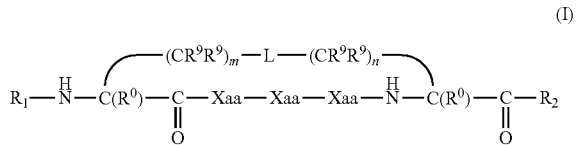

wherein each Xaa is independently selected from any L-alpha amino acid residues, 2 or 3 of which are favorable to alpha helix formation; or
wherein each Xaa is independently selected from any D-alpha amino acid residues, 2 or 3 of which are favorable to alpha helix formation;
wherein the amino acid residues that are favorable to alpha helix formation are selected from alanine, arginine, lysine, methionine, leucine, glutamic acid, glutamine, cysteine, isoleucine, phenylalanine, tryptophan, histidine and aspartic acid;
wherein the compound has at least three (1,5) intramolecular hydrogen bonds;
$R_1$ is selected from
an N-terminal capping group;
a non-peptidic group;
a group that mimics an amino acid side chain; and
an amino acid residue optionally capped by an N-terminal capping group, a non-peptidic group, or a group that mimics an amino acid side chain;
$R_2$ is selected from
a C-terminal capping group;
a group that mimics an amino acid side chain;
a group that activates the terminal carboxylic acid carbonyl group to nucleophilic substitution; and
a peptide of 1, 2, 3, 4 or 5 amino acid residues optionally capped by a C-terminal capping group; a group that mimics an amino acid side chain; or a group which activates the terminal carboxylic acid carbonyl group to nucleophilic substitution;
each $R^9$ and $R^0$ are independently selected from H, $C_1$-$C_{10}$alkyl, $C_2$-$C_{10}$alkenyl, $C_2$-$C_{10}$alkynyl, $C_3$-$C_{10}$cylcoalkyl, $C_5$-$C_{10}$cycloalkenyl, —OH, —O$C_1$-$C_{10}$alkyl, —NH$_2$, —NH($C_1$-$C_{10}$alkyl), —N($C_1$-$C_{10}$alkyl)$_2$, $C_6$-$C_{12}$aryl, $C_3$-$C_{10}$heterocyclyl, $C_5$-$C_{10}$heteroaryl and halo;
L is selected from —NH—C(O)—, —C(O)—NH—, —S—S—, —CH(OH)CH$_2$—, —CH$_2$CH(OH)—, —CH=CH—, —CH$_2$—CH$_2$—, —NH—CH$_2$—, —C(O)—CH$_2$—, —CH$_2$—C(O)—, —S(O)$_t$—NH—, —NH—S(O)$_t$—, CH$_2$—P(=O)(OH)— and —P(=O)(OH)—CH$_2$—;
m is 4;
n is 1; and
t is 0, 1 or 2.

2. A compound according to claim 1, wherein $R_1$ is an N-terminal capping group that stabilizes the terminus of a helix.

3. A compound according to claim 2, wherein the N-terminal capping group is selected from acyl and N-succinate.

4. A compound according to claim 1, wherein in $R_1$, the group that mimics an amino acid side chain is selected from any natural or unnatural amino acid side chain that is attached to the N-terminal amino group of the peptide through a carbonyl group derived from a carboxylic acid by formation of an amide bond.

5. A compound according to claim 1, wherein in $R_1$, the group that mimics an amino acid side chain is selected from: CH$_3$CH$_2$C(O)(CH$_2$)$_u$C(O)—, NH$_2$(NH=)CNHC(O)(CH$_2$)$_u$C(O)—, H$_2$NC(O)(CH$_2$)$_2$C(O)(CH$_2$)$_u$C(O)—, HOC(O)(CH$_2$)$_2$C(O)(CH$_2$)$_u$C(O)—, HS(CH$_2$)$_2$C(O)(CH$_2$)$_u$C(O)—, H$_2$NC(O)(CH$_2$)$_3$C(O)(CH$_2$)$_u$C(O)—, HOC(O)(CH$_2$)$_2$C(O)(CH$_2$)$_u$C(O)—, (4-imidazolyl)(CH$_2$)$_2$C(O)(CH$_2$)$_u$C(O)—, CH$_3$CH$_2$CH(CH$_3$)CH$_2$C(O)(CH$_2$)$_u$C(O)—, (CH$_3$)$_2$CH(CH$_2$)$_2$C(O)(CH$_2$)$_u$C(O)—, H$_2$N(CH$_2$)$_5$C(O)(CH$_2$)$_u$C(O)—, CH$_3$S(CH$_2$)$_3$C(O)(CH$_2$)$_u$C(O)—, Ph(CH$_2$)$_2$C(O)(CH$_2$)$_u$C(O)—, Ph(CH$_2$)$_4$C(O)(CH$_2$)$_u$C(O)—, HO(CH$_2$)$_2$C(O)(CH$_2$)$_u$C(O)—, HOCH(CH$_3$)CH$_2$C(O)(CH$_2$)$_u$C(O)—, (3-indolyl)(CH$_2$)$_2$(CH$_2$)$_u$C(O)—, (4-hydroxyphenyl)(CH$_2$)$_2$C(O)(CH$_2$)$_u$C(O)—, (4-hydroxyphenyl)(CH$_2$)$_3$C(O)(CH$_2$)$_u$C(O)—, (CH$_3$)$_2$CHCH$_2$C(O)(CH$_2$)$_u$C(O)—, CH$_3$CH$_2$CH$_2$C(O)(CH$_2$)$_u$C(O)—, C$_6$H$_{10}$CH$_2$C(O)(CH$_2$)$_u$C(O)—, C$_5$H$_8$CH$_2$C(O)(CH$_2$)$_u$C(O)—, CH$_3$C(O)(CH$_2$)$_u$C(O)—, CH$_3$(CH$_2$)$_4$C(O)(CH$_2$)$_u$C(O)—, CH$_3$(CH$_2$)$_5$C(O)(CH$_2$)$_u$C(O)—, HOC(O)CH$_2$C(O)(CH$_2$)$_u$C(O)—, HS(CH$_2$)C(O)(CH$_2$)$_u$C(O)—, H$_2$N(CH$_2$)$_4$C(O)(CH$_2$)$_u$C(O)— and HOCH$_2$C(O)(CH$_2$)$_u$C(O)— wherein u is 0 or an integer from 1 to 10.

6. A compound according to claim 1, wherein the non-peptidic group enhances the stability, bioavailability or activity of the compound.

7. A compound according to claim 1, wherein the non-peptidic group is selected from: hydrophobic groups; groups which stabilize or mimic alpha-helices, groups which mimic the secondary structure of peptides; groups which improve bioavailability; and groups which are recognized by transport receptors to allow or improve transport of the peptides to the site of activity.

8. A compound according to claim 1, wherein $R_2$ comprises a C-terminal capping group that stabilizes the terminus of an alpha helix.

9. A compound according to claim 8, wherein the C-terminal capping group is NH$_2$.

10. A compound according to claim 1, wherein in $R_2$, the group that mimics an amino acid side chain is any common or unnatural amino acid side chain that is attached to the C-terminal carbonyl group of the peptide through an amine group by formation of an amide bond.

11. A compound according to claim 1, wherein in $R_2$, the group that mimics an amino acid side chain is selected from: —NH(CH$_2$)$_u$NHCH$_2$CH$_3$, —NH(CH$_2$)$_u$NH(CH$_2$)$_4$NHC(=NH)NH$_2$, —NH(CH$_2$)$_u$NH(CH$_2$)$_2$C(O)NH$_2$, —NH(CH$_2$)$_u$NH(CH$_2$)$_2$CO$_2$H, —NH(CH$_2$)$_u$NH(CH$_2$)$_2$SH, —NH(CH$_2$)$_u$NH(CH$_2$)$_3$C(O)NH$_2$, —NH(CH$_2$)$_u$NH(CH$_2$)$_3$CO$_2$H, —NH(CH$_2$)$_u$NH(CH$_2$)$_2$(4-imidazolyl), —NH(CH$_2$)$_u$NHCH$_2$CH(CH$_3$)CH$_2$CH$_3$, —NH(CH$_2$)$_u$NH(CH$_2$)$_2$CH(CH$_3$)$_2$, —NH(CH$_2$)$_u$NH(CH$_2$)$_5$NH$_2$, —NH(CH$_2$)$_u$NH(CH$_3$)$_3$SCH$_3$, —NH(CH$_2$)$_u$NH(CH$_2$)$_2$(3-indolyl), —NH(CH$_2$)$_u$NH(CH$_2$)$_2$(4-hydroxyphenyl), —NH(CH$_2$)$_u$NH(CH$_2$)$_3$(4-hydroxyphenyl), —NH(CH$_2$)$_u$NH—CH$_2$CH(CH$_3$)$_2$, —NH(CH$_2$)$_u$NHCH$_2$CH$_2$CH$_3$, —NH(CH$_2$)$_u$NHCH$_2$C$_8$H$_{10}$, —NH(CH$_2$)$_u$NHCH$_2$C$_5$H$_8$, —NH(CH$_2$)$_u$N-HCH$_3$, —NH(CH$_2$)$_u$NH(CH$_2$)$_4$—CH$_3$, —NH(CH$_2$)$_u$NH(CH$_2$)$_5$CH$_3$, —NH(CH$_2$)$_u$NHCH$_2$CO$_2$H, —NH(CH$_2$)$_u$NHCH$_2$SH, —NH(CH$_2$)$_u$NH(CH$_2$)$_2$OH, —NH(CH$_2$)$_u$NH(CH$_2$)$_5$NH$_2$ and —NH(CH$_2$)$_u$NHCH$_2$OH; wherein u is 0 or an integer from 1 to 10.

12. A compound according to claim 1, wherein the group that activates the terminal carboxylic carbonyl group to nucleophilic substitution converts the terminal carboxylic acid to a group selected from an acid chloride, an acid anhydride, an acyl azide, an O-acylisourea, a phosphonium compound or an activated ester.

13. A compound according to claim 1, wherein the non-peptidic group enhances the stability and circulating time, or decreases immunogenicity, or increases solubility, bioavailability or activity of the compound.

14. A compound according to claim 1, wherein each $R^9$ is selected from H, $CH_3$, $CH_2CH_3$, vinyl, OH, $OCH_3$, $NH_2$, $NH(CH_3)$, $N(CH_3)_2$, phenyl, F or Cl.

15. A compound according to claim 1, wherein each $R^0$ is selected from H, $CH_3$, $CH_2CH_3$ or vinyl.

16. A compound according to claim 1, wherein each Xaa is selected to mimic amino acid residues in a known alpha helical peptide of interest.

17. A compound according to claim 1, wherein an individual Xaa is the same or different as another Xaa.

18. A compound according to claim 1, wherein the amino acid residues that are favorable to alpha helix formation are selected from alanine, arginine, lysine, methionine, leucine, glutamic acid and glutamine.

19. A compound according to claim 1, wherein L is —NH—C(O)— or —C(O)—NH—.

20. A compound according to claim 1, wherein the amino-terminal and carboxy-terminal residues of the compound are Lys and Asp, respectively.

21. A composition comprising a compound according to claim 1 and a pharmaceutically acceptable carrier, diluent or adjuvant.

22. A compound according to claim 1, which is cyclo(3,7)-LR[KMADD]F (SEQ ID NO:65).

* * * * *

UNITED STATES PATENT AND TRADEMARK OFFICE
CERTIFICATE OF CORRECTION

PATENT NO. : 8,629,241 B2
APPLICATION NO. : 13/483926
DATED : January 14, 2014
INVENTOR(S) : David P. Fairlie et al.

It is certified that error appears in the above-identified patent and that said Letters Patent is hereby corrected as shown below:

In the Claims

Column 101, lines 48-53 should read:

L is selected from –NH-C(O)-, –C(O)-NH-, -S-S-, -CH(OH)CH$_2$-, CH$_2$CH(OH)-, -CH=CH-, -CH$_2$-CH$_2$-, -NH-CH$_2$- -CH$_2$-NH-, -CH$_2$-S-, -S-CH$_2$-, -C(O)-CH$_2$-, -CH$_2$-C(O)-, -S(O)$_t$-NH-, -NH-S(O)$_t$-, CH$_2$-P(=O)(OH)- and -P(=O)(OH)-CH$_2$-;

Column 102, lines 56 and 57 should read:

NHCH$_2$C$_6$H$_{10}$, -NH(CH$_2$)$_u$NHCH$_2$C$_5$H$_8$, -NH(CH$_2$)$_u$N-HCH$_3$, -NH(CH$_2$)$_u$NH(CH$_2$)$_4$CH$_3$, -NH(CH$_2$)$_u$NH

Signed and Sealed this
First Day of April, 2014

Michelle K. Lee
*Deputy Director of the United States Patent and Trademark Office*